(12) United States Patent
Tsai et al.

(10) Patent No.: US 10,000,517 B2
(45) Date of Patent: *Jun. 19, 2018

(54) ORGANIC ELECTROLUMINESCENT MATERIALS AND DEVICES

(71) Applicant: Universal Display Corporation, Ewing, NJ (US)

(72) Inventors: Jui-Yi Tsai, Newtown, PA (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/590,218

(22) Filed: May 9, 2017

(65) Prior Publication Data
US 2017/0240580 A1    Aug. 24, 2017

Related U.S. Application Data

(62) Division of application No. 15/251,212, filed on Aug. 30, 2016, now Pat. No. 9,680,113, which is a division of application No. 14/573,722, filed on Dec. 17, 2014, now Pat. No. 9,450,195.

(51) Int. Cl.
| | | |
|---|---|---|
| *C07F 15/00* | (2006.01) | |
| *C07F 19/00* | (2006.01) | |
| *H01L 51/00* | (2006.01) | |
| *C09K 11/06* | (2006.01) | |
| *C07F 17/02* | (2006.01) | |
| *C09K 11/02* | (2006.01) | |
| *H01L 51/50* | (2006.01) | |

(52) U.S. Cl.
CPC ...... *C07F 15/0033* (2013.01); *C07F 15/0086* (2013.01); *C07F 17/02* (2013.01); *C07F 19/00* (2013.01); *C09K 11/025* (2013.01); *C09K 11/06* (2013.01); *H01L 51/009* (2013.01); *H01L 51/0054* (2013.01); *H01L 51/0058* (2013.01); *H01L 51/0067* (2013.01); *H01L 51/0072* (2013.01); *H01L 51/0074* (2013.01); *H01L 51/0085* (2013.01); *H01L 51/0086* (2013.01); *H01L 51/0087* (2013.01); *H01L 51/0088* (2013.01); *H01L 51/0094* (2013.01); *C09K 2211/1007* (2013.01); *C09K 2211/1022* (2013.01); *C09K 2211/1029* (2013.01); *C09K 2211/1033* (2013.01); *C09K 2211/1044* (2013.01); *C09K 2211/1088* (2013.01); *C09K 2211/185* (2013.01); *H01L 51/5004* (2013.01); *H01L 51/5016* (2013.01); *H01L 2251/552* (2013.01)

(58) Field of Classification Search
CPC .......... C07F 15/00; C07F 19/00; H01L 51/00; H01L 51/50
USPC .............. 546/2; 548/101; 313/504
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 7,858,724 | B2 | 12/2010 | Kanitz et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Díez, Álvaro et al., "Heteropolynuclear cycloplatinated complexes: Structural and photophysical properties," Coordination Chemistry Reviews 255 (2011) 2426-2447
Fery-Forgues, Suzanne et al., "Ferrocene and ferrocenyl derivatives in luminescent systems," Journal of Photochemistry and Photobiology A: Chemistry 132 (2000) 137-159.
Shu, Qinghai et al., "A Bis(ferrocenyl)phenanthroline Iridium(III) Complex as a Lab-on-a-Molecule for Cyanide and Fluoride in Aqueous Solution," Inorg. Chem. 2012, 51, 13123-13127.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).

(Continued)

*Primary Examiner* — Charanjit Aulakh
(74) *Attorney, Agent, or Firm* — Duane Morris LLP

(57) ABSTRACT

Phosphorescent metal complexes comprising a pendant redox-active metallocene are disclosed. These complexes are useful as emitters for phosphorescent OLEDs.

18 Claims, 3 Drawing Sheets

(56) References Cited

U.S. PATENT DOCUMENTS

| | | | |
|---|---|---|---|
| 8,815,415 B2 | 8/2014 | Tsai et al. | |
| 9,450,195 B2* | 9/2016 | Tsai | C07F 17/02 |
| 9,680,113 B2* | 6/2017 | Tsai | H01L 51/009 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0136286 A1 | 6/2005 | Royster, Jr. et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |

FOREIGN PATENT DOCUMENTS

| | | |
|---|---|---|
| EP | 2034538 | 3/2009 |
| JP | 2004103584 | 4/2004 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107251 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005098988 | 10/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

(56) References Cited

OTHER PUBLICATIONS

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

FORMULA I

FORMULA II

FORMULA III

ORGANIC ELECTROLUMINESCENT MATERIALS AND DEVICES

CROSS-REFERENCE TO RELATED APPLICATIONS

This application is a divisional of the U.S. patent application Ser. No. 15/251,212, filed on Aug. 30, 2016, which is a divisional of U.S. patent application Ser. No. 14/573,722, filed on Dec. 17, 2014, now U.S. Pat. No. 9,450,195 B2.

FIELD OF THE INVENTION

The present invention relates to compounds for use as phosphorescent emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

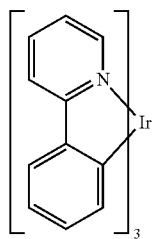

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound comprising a first ligand $L^1$ having the formula:

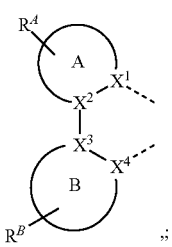

Formula I wherein ring A and ring B are each independently a 5-membered or 6-membered carbocyclic or heterocyclic ring;

wherein $X^1$, $X^2$, $X^3$, and $X^4$ are independently C or N;

wherein $R^A$ and $R^B$ each independently represent mono, di, tri, or tetra substitution, or no substitution;

wherein at least one of $R^A$ and $R^B$ has the following formula:

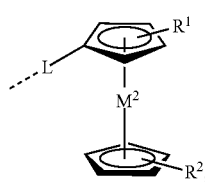

Formula II wherein L is a direct bond or a linker selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein $R^1$ represents mono, di, tri, or tetra substitution, or no substitution;

wherein $R^2$ represents mono, di, tri, tetra, or penta substitution, or no substitution;

wherein $M^2$ is selected from the group consisting of Os, Ru, and Re;

wherein $R^1$ and $R^2$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein when $R^A$ and $R^B$ is not Formula II, $R^A$ and $R^B$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any two adjacent substituents are optionally joined to form a ring, which can be further substituted;

wherein the ligand $L^1$ is coordinated to a metal M, wherein M is selected from the group consisting of Ir, Rh, Re, Ru, Os, Pt, Au, and Cu;

wherein the metal M can be coordinated to other ligands; and wherein the ligand $L^1$ is optionally linked with other ligands to comprise a tridentate, tetradentate, pentadentate or hexadentate ligand.

According to another embodiment, a device comprising one or more organic light emitting devices is also provided. At least one of the one or more organic light emitting devices can include an anode, a cathode, and an organic layer, disposed between the anode and the cathode, wherein the organic layer includes the compound comprising a first ligand $L^1$ having the formula:

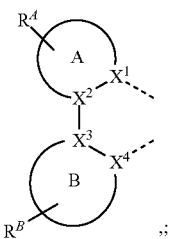

Formula I where the variables A, B, $R^A$, $R^B$, $X^1$, $X^2$, $X^3$, and $X^4$ are as defined herein, including all of the variations. The device can be a consumer product, an electronic component module, an organic light-emitting device, and/or a lighting panel.

According to yet another embodiment, a formulation comprising the compound comprising a first ligand $L^1$ having the formula:

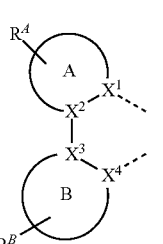

Formula I where the variables A, B, $R^A$, $R^B$, $X^1$, $X^2$, $X^3$, and $X^4$ are as defined herein, including all of the variations, is provided.

The present disclosure provides a phosphorescent metal complex comprising a pendant redox-active metallocene. This metal complex system allows the optical band gap of the luminescent system to be preserved, while taking advantage of the electroactive properties of metallocene. These metal complexes are useful as emitters for phosphorescent OLEDs (PHOLEDs), especially for blue phosphorescent emitters.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
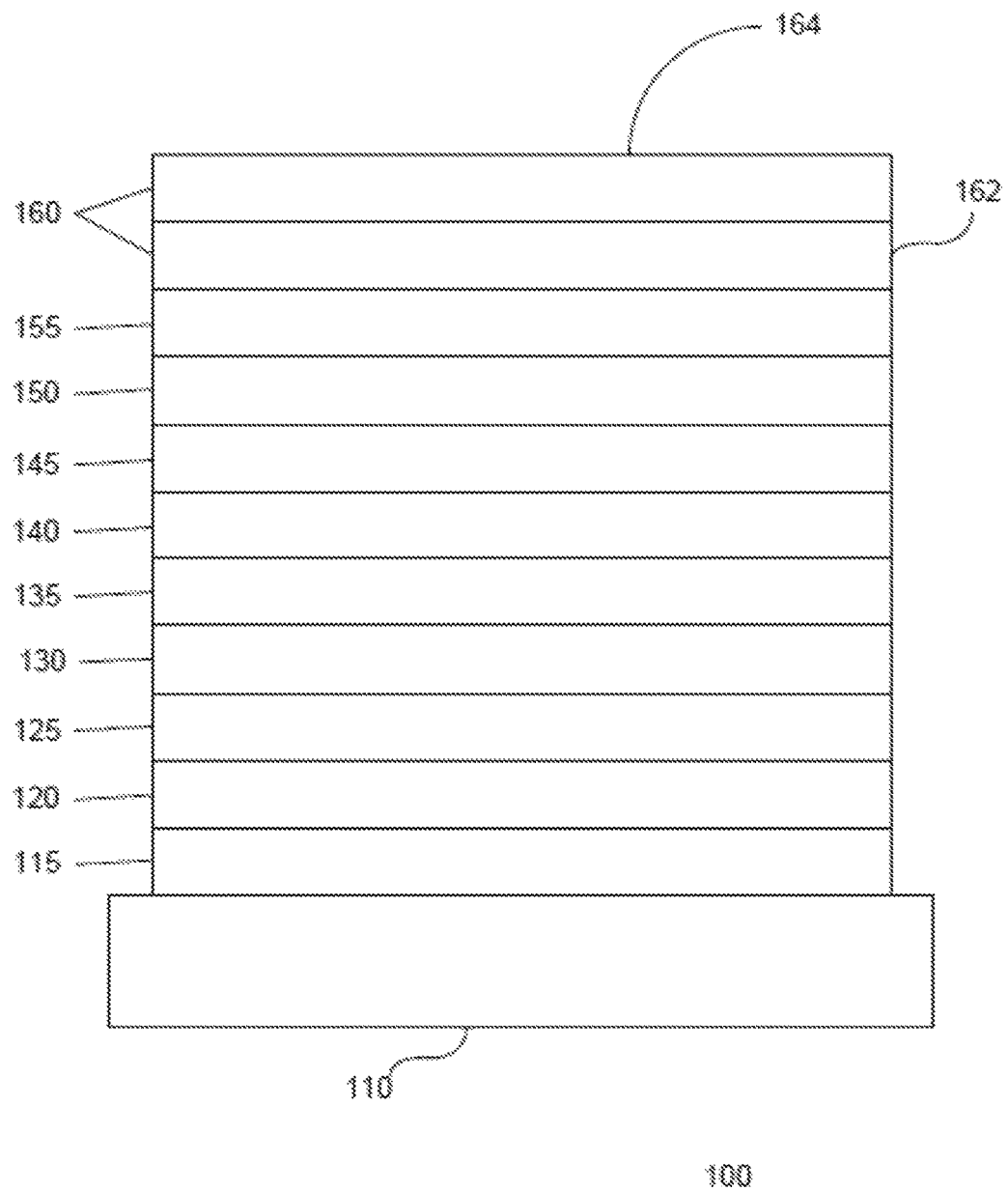
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
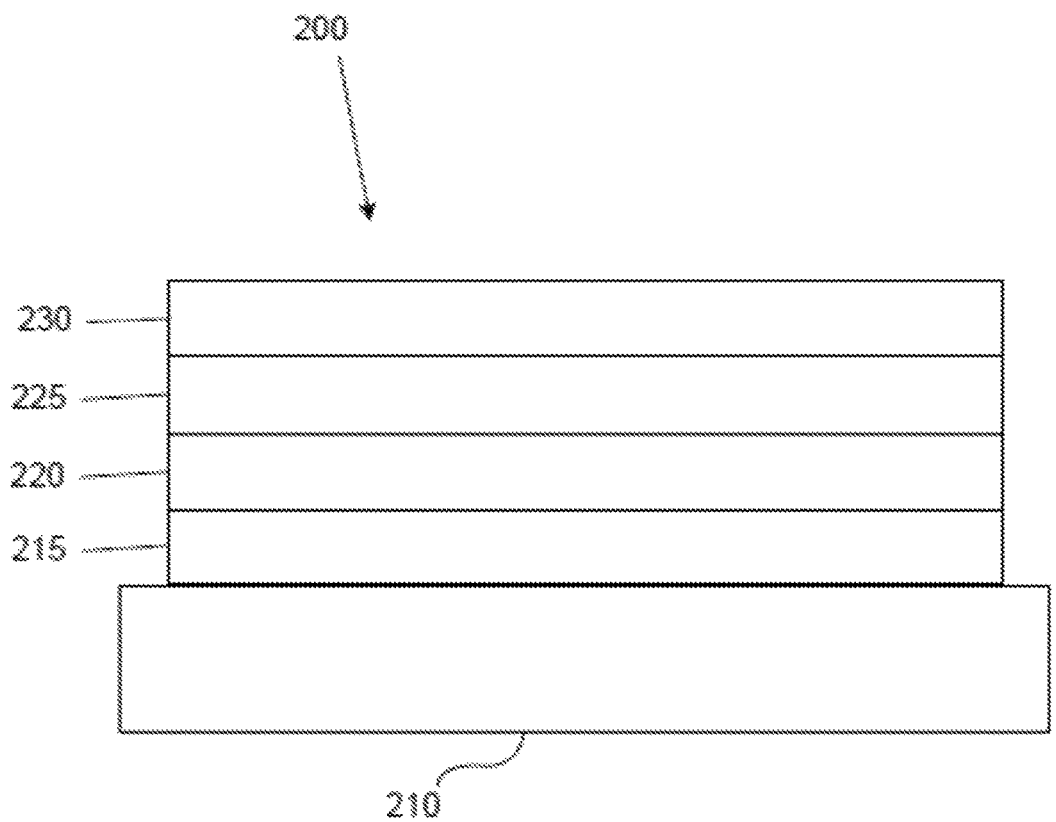
FIG. 2 shows an inverted organic light emitting device that does not have a separate electron transport layer.
Figure 3:
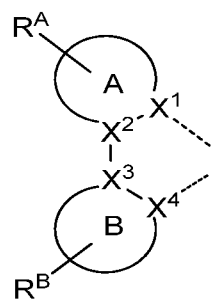
FIG. 3 shows Formula I for the disclosed novel compound.
Figure 4:
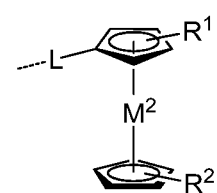
FIG. 4 shows Formula II for the substituents in Formula I.
Figure 5:
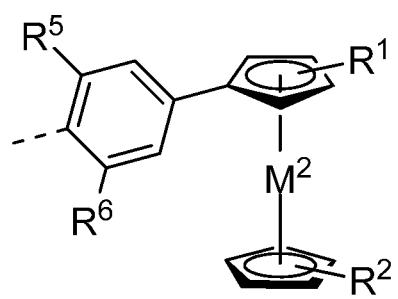
FIG. 5 shows Formula III for the substituents in Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The present disclosure provides a novel phosphorescent dopant system with the general structure represented by Formula I described below. Inventors believe that the disclosed phosphorescent dopants have beneficially small band gap while maintaining the triplet energy.

The present disclosure provides a novel compound comprising a first ligand $L^1$ having the Formula:

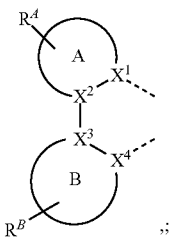

Formula I wherein ring A and ring B are each independently a 5-membered or 6-membered carbocyclic or heterocyclic ring;

wherein $X^1$, $X^2$, $X^3$, and $X^4$ are independently C or N;

wherein $R^A$ and $R^B$ each independently represent mono, di, tri, or tetra substitution, or no substitution;

wherein at least one of $R^A$ and $R^B$ has a structure according to the following formula:

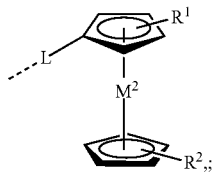

Formula II wherein L is a direct bond or a linker selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein $R^1$ represents mono, di, tri, or tetra substitution, or no substitution;

wherein $R^2$ represents mono, di, tri, tetra, or penta substitution, or no substitution;

wherein $M^2$ is selected from the group consisting of Os, Ru, and Re;

wherein $R^1$ and $R^2$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein when $R^A$ and $R^B$ is not Formula II, $R^A$ and $R^B$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any two adjacent substituents are optionally joined to form a ring, which can be further substituted;

wherein the ligand $L^1$ is coordinated to a metal M;

wherein the metal M can be coordinated to other ligands; and wherein the ligand $L^1$ is optionally linked with other ligands to comprise a tridentate, tetradentate, pentadentate or hexadentate ligand.

In one embodiment of the compound, M is selected from the group consisting of Ir, Rh, Re, Ru, Os, Pt, Au, and Cu. In some embodiments of the compound, M is Ir or Pt.

In the compound, ring A and ring B are each independently a 5-membered or 6-membered aromatic or heteroaromatic ring.

In another embodiment of the compound, at least one of $R^A$ and $R^B$ has a structure according to the following formula:

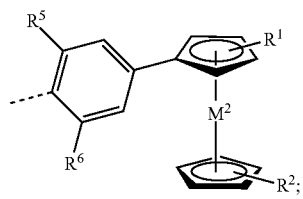

Formula III and wherein $R^5$ and $R^6$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In one embodiment of the compound, the ligand $L^1$ is selected from the group consisting of:

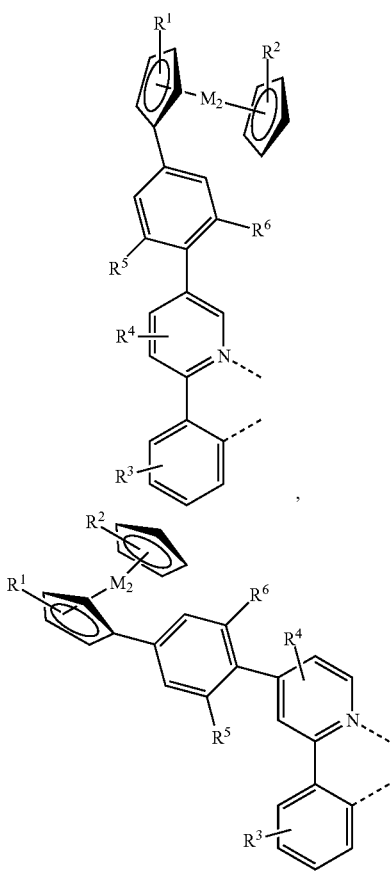

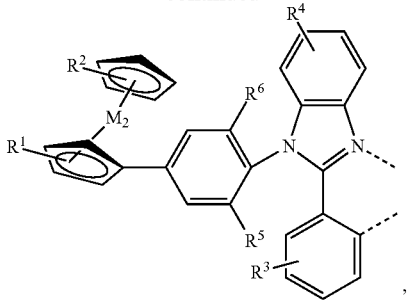

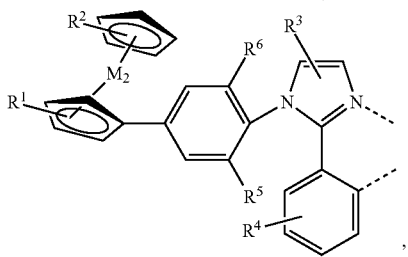

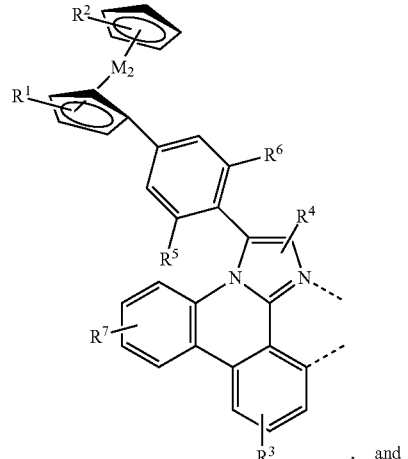

, and

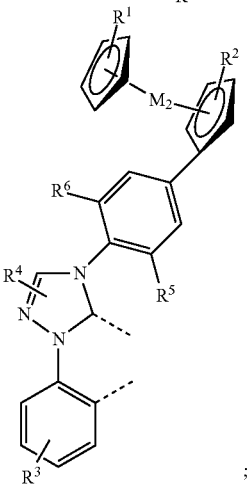

;

wherein $R^1$, $R^2$, $R^5$, and $R^6$ are as defined above;

wherein $R^3$ and $R^4$ each independently represent mono, di, tri, or tetra substitution, or no substitution;

wherein $R^7$ represents mono, di or tri substitution, or no substitution; and wherein $R^3$, $R^4$, $R^5$, $R^6$, and $R^7$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

The compound can be homoleptic or heteroleptic. In other embodiments, the compound is neutral.

In some embodiments of the compound, the ligand $L^1$ is selected from the group consisting of:

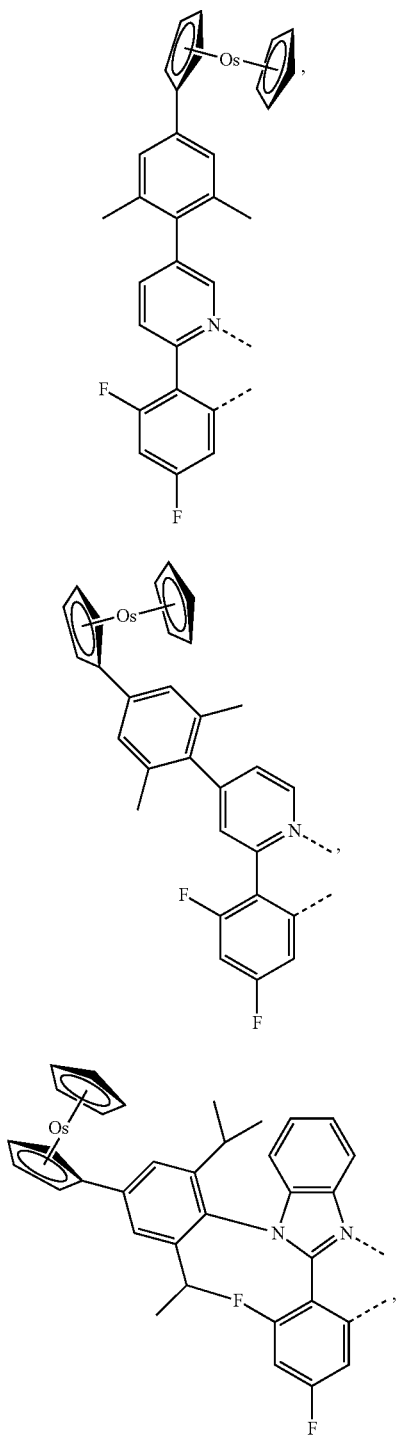

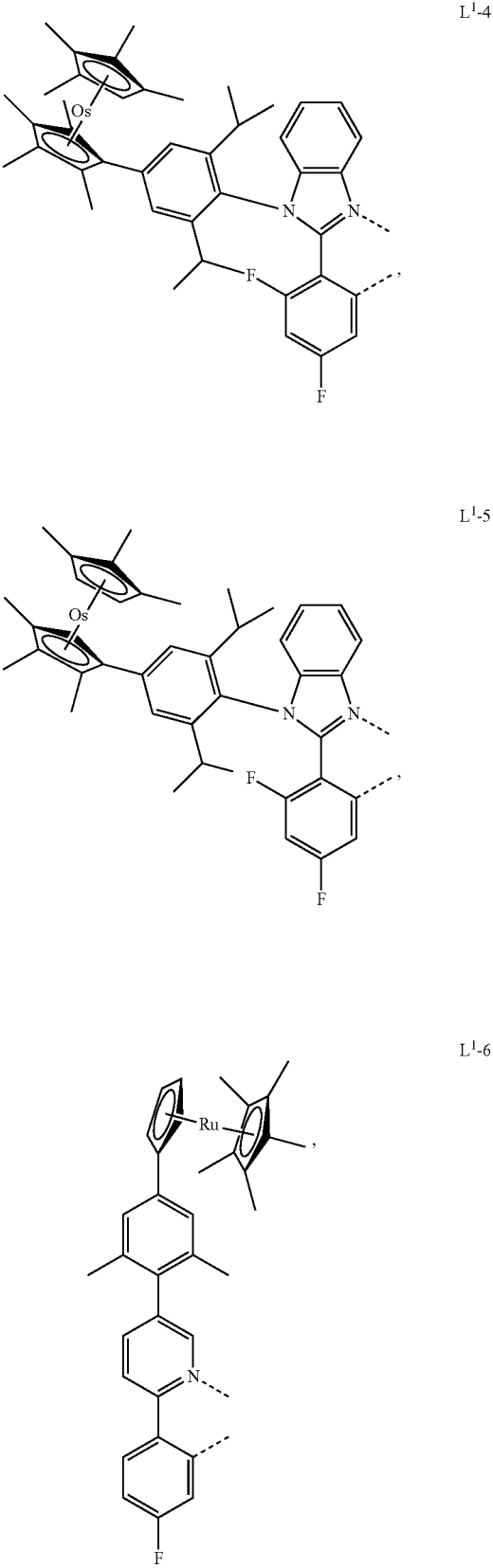

L¹-7
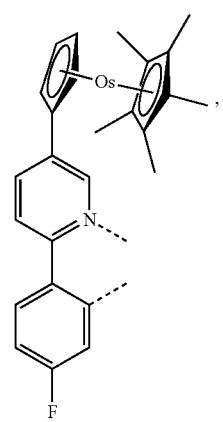
L¹-8
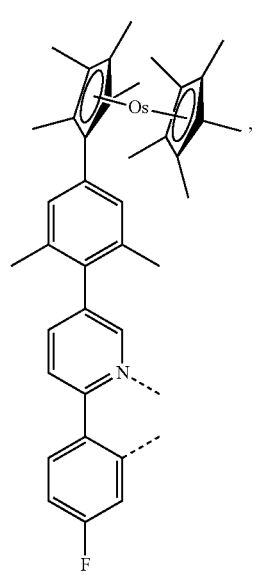
L¹-9
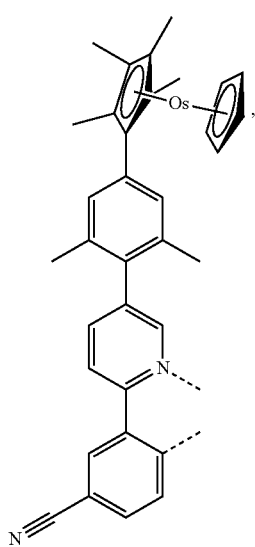
L¹-10
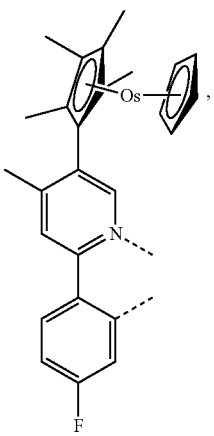
L¹-11
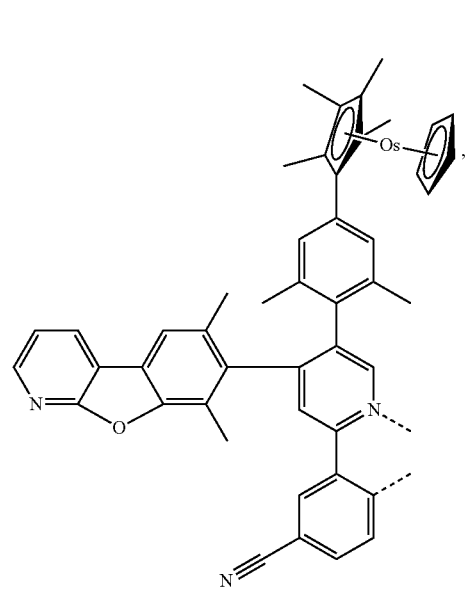
L¹-12
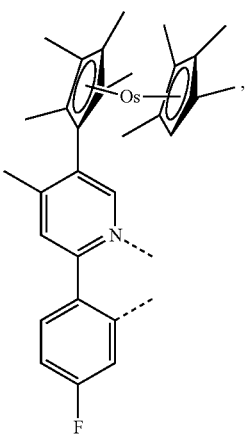

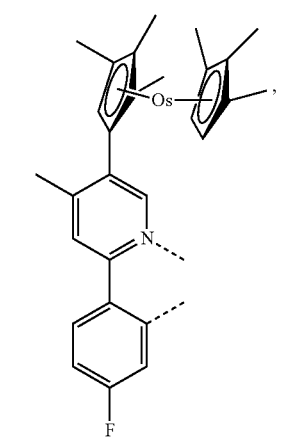 L¹-13
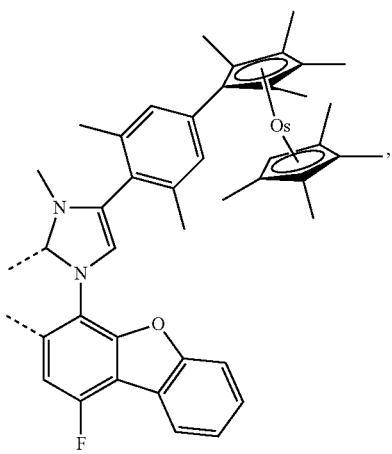 L¹-16
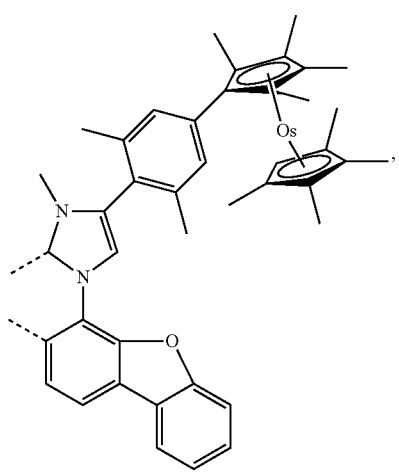 L¹-14
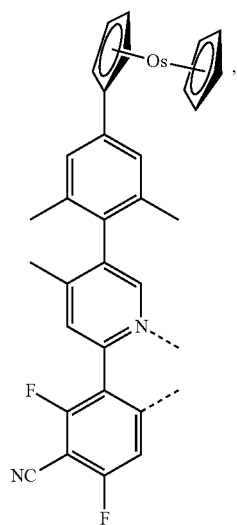 L¹-17
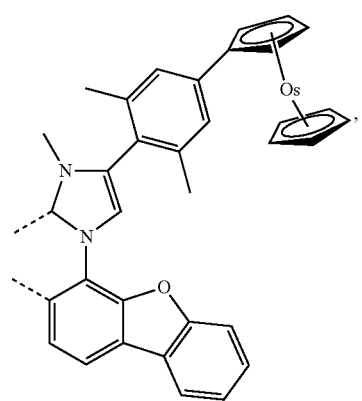 L¹-15
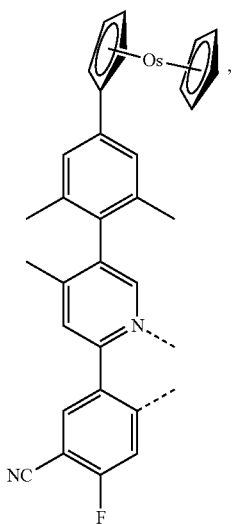 L¹-18

L¹-19
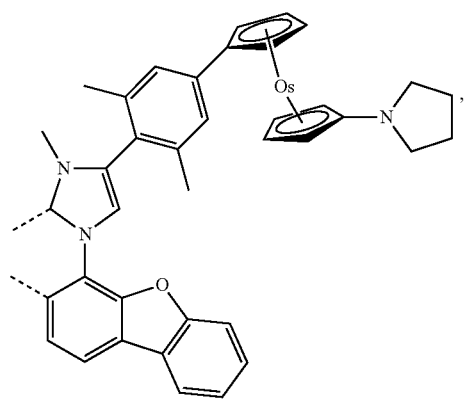
L¹-20
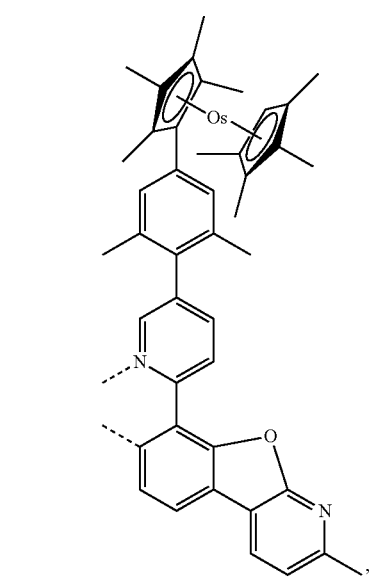
L¹-21
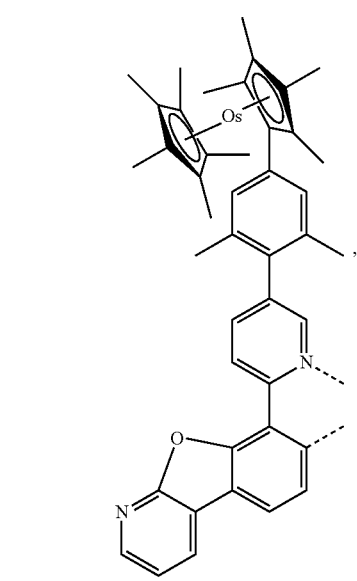
L¹-22
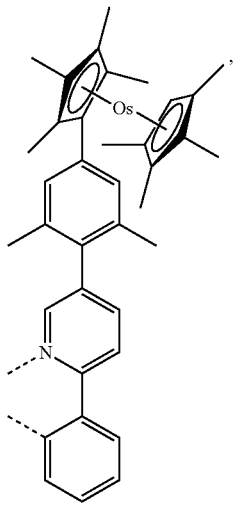
L¹-23
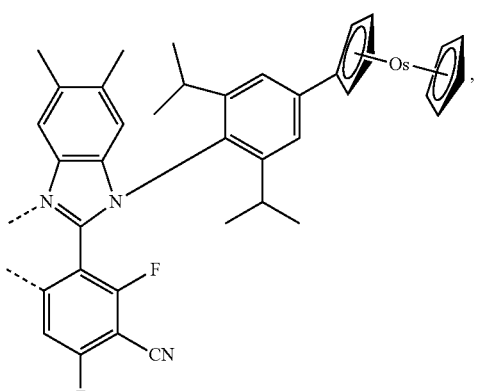
L¹-24
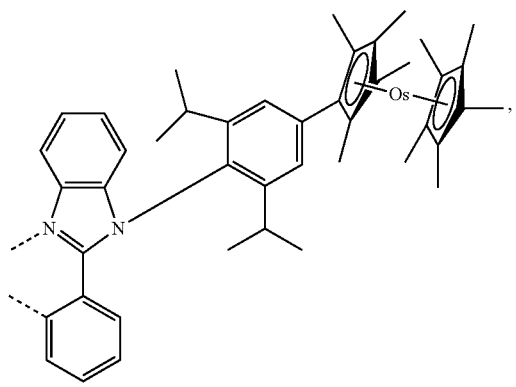

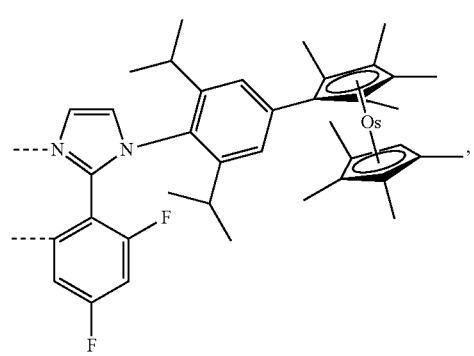
L¹-25
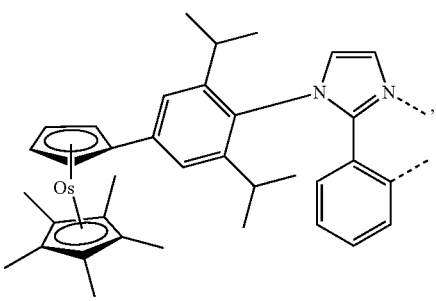
L¹-29
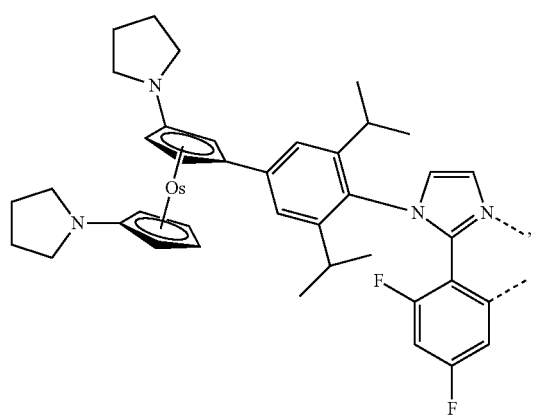
L¹-26
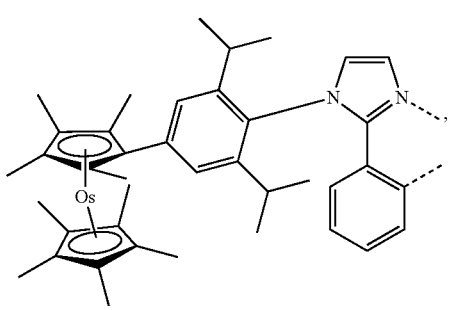
L¹-30
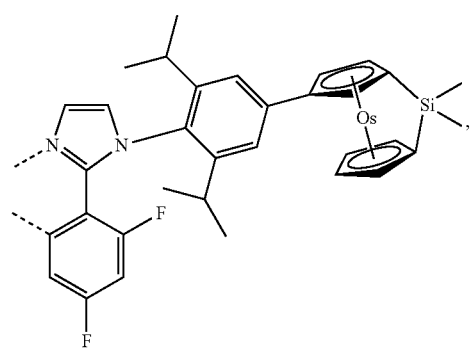
L¹-27
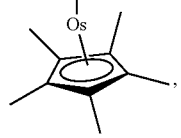
L¹-31
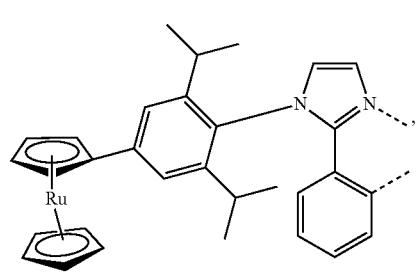
L¹-28
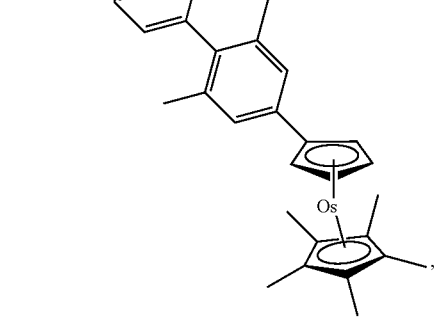
L¹-32

-continued

L¹-33

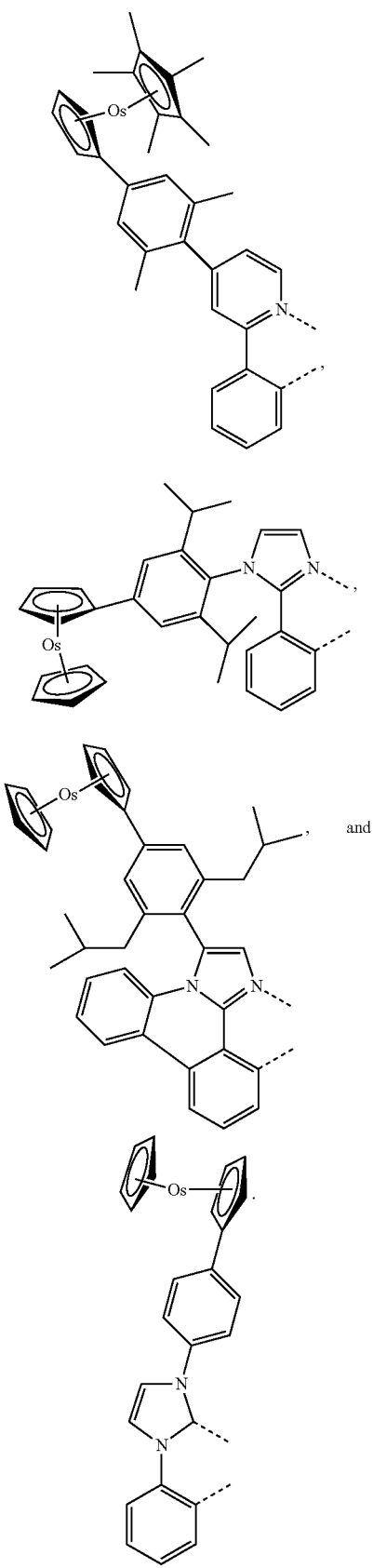

and

In another embodiment of the compound, the compound has the formula of $M(L^1)_x(L^2)_y(L^3)_z$;

wherein $L^2$ is a second ligand, and $L^3$ is a third ligand, and $L^2$ and $L^3$ can be the same or different;

wherein x is 1, 2, or 3;

wherein y is 0, 1, or 2;

wherein z is 0, 1, or 2;

wherein x+y+z is the oxidation state of the metal M;

wherein the second ligand $L^2$ and the third ligand $L^3$ are independently selected from the group consisting of:

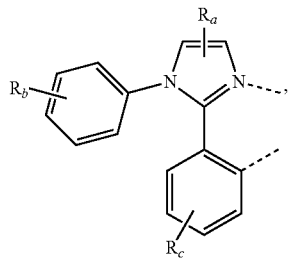

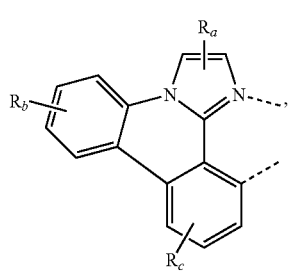

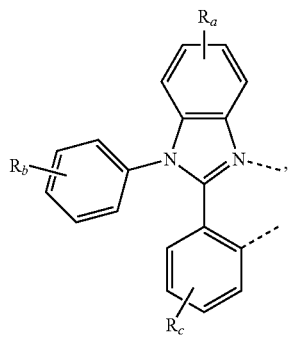

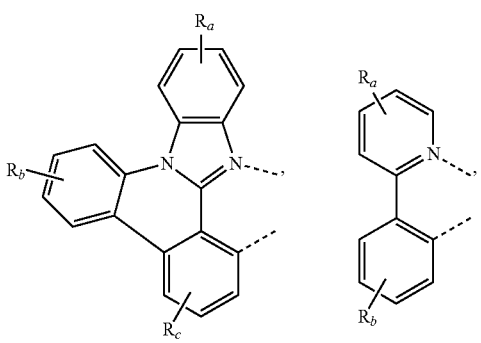

-continued
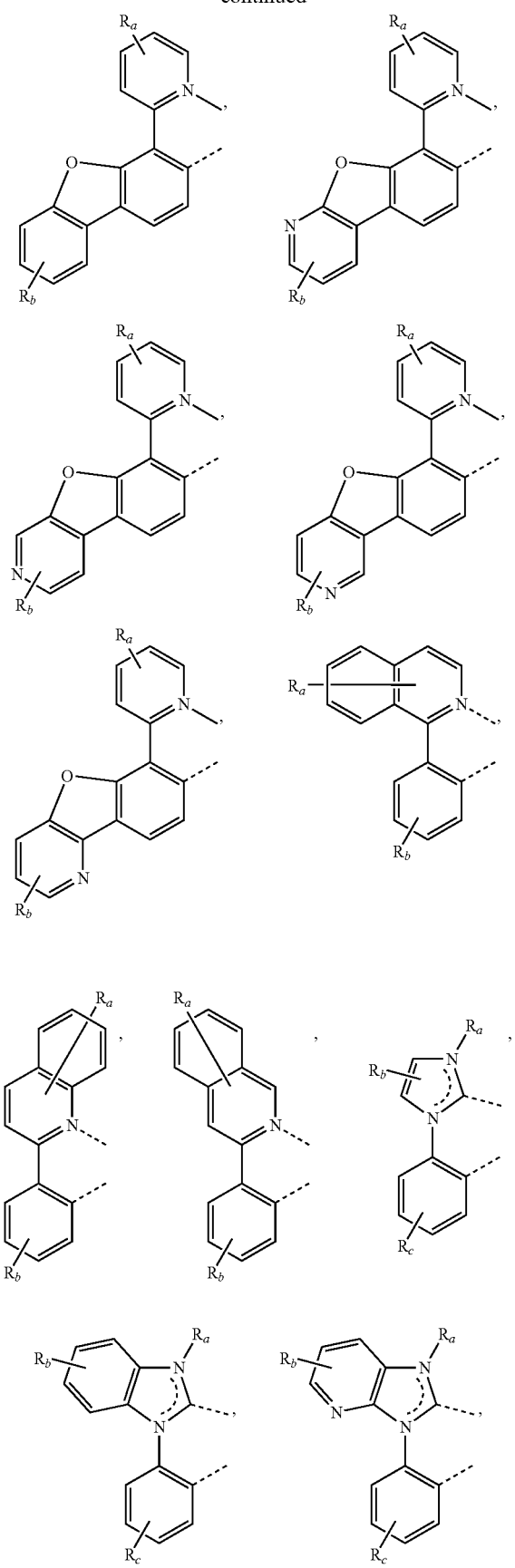
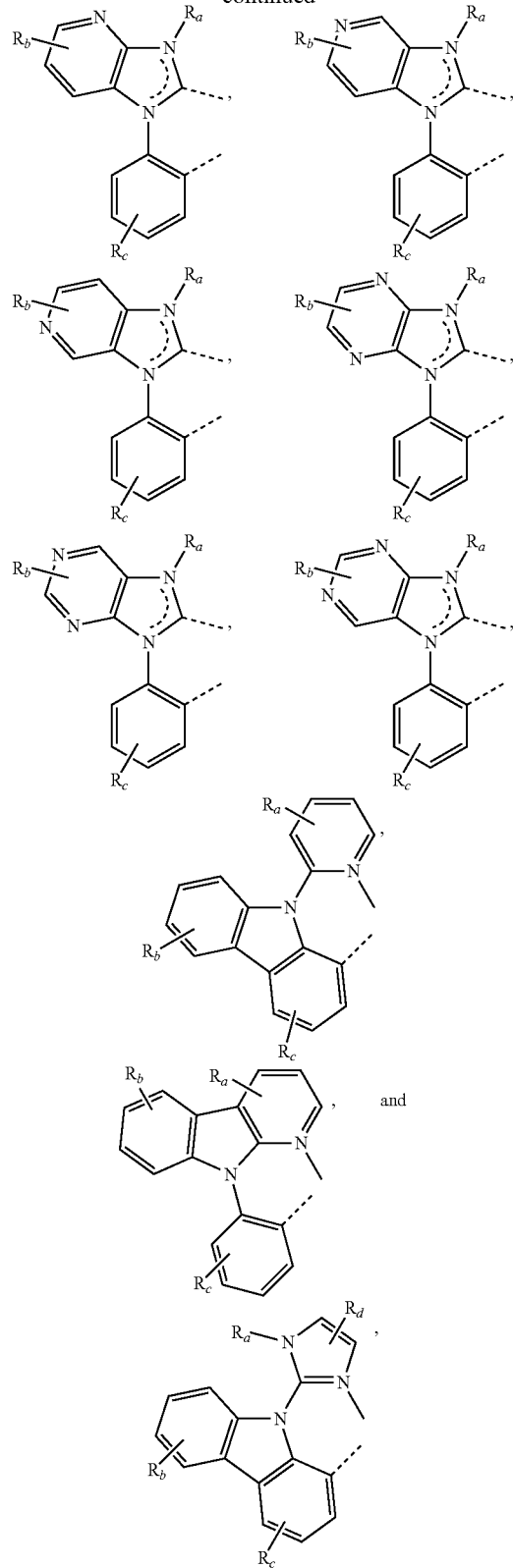
wherein $R_a$, $R_b$, $R_c$, and $R_d$ may represent mono, di, tri, or tetra substitution, or no substitution;
wherein $R_a$, $R_b$, $R_c$, and $R_d$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment of the compound having the formula of $M(L^1)_x(L^2)_y(L^3)_z$, the compound has the formula of $Ir(L^1)(L^2)_2$.

In another embodiment of the compound having the formula of $M(L^1)_x(L^2)_y(L^3)_z$, the compound has the formula of $Pt(L^1)_2$ or $Pt(L^1)(L^2)$. In some embodiments, $L^1$ can be connected to the other $L^1$ or $L^2$ to form a tetradentate ligand.

In another embodiment of the compound comprising a first ligand $L^1$ having a structure according to Formula I:

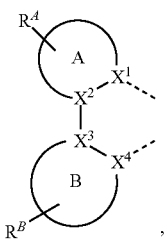

described above, the compound is selected from the group consisting of:

Compound 1

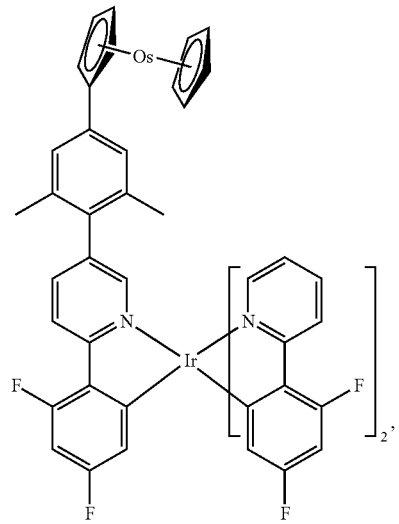

Compound 2

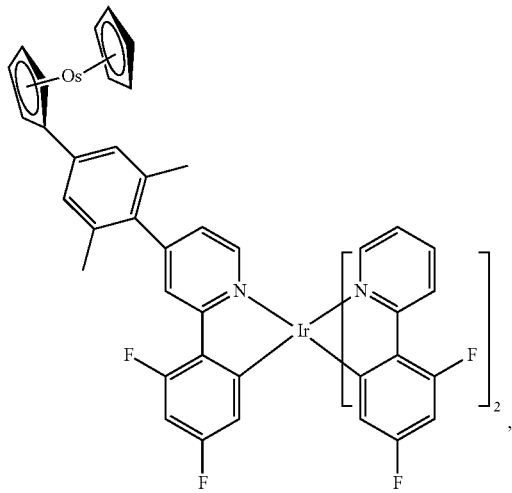

Compound 3

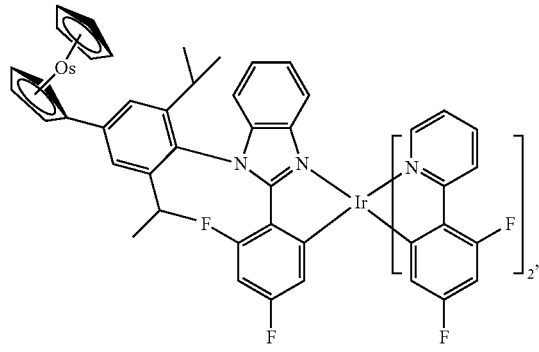

Compound 4

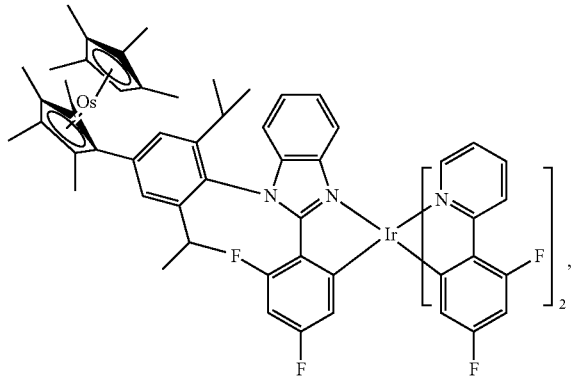

-continued
Compound 5
Compound 6
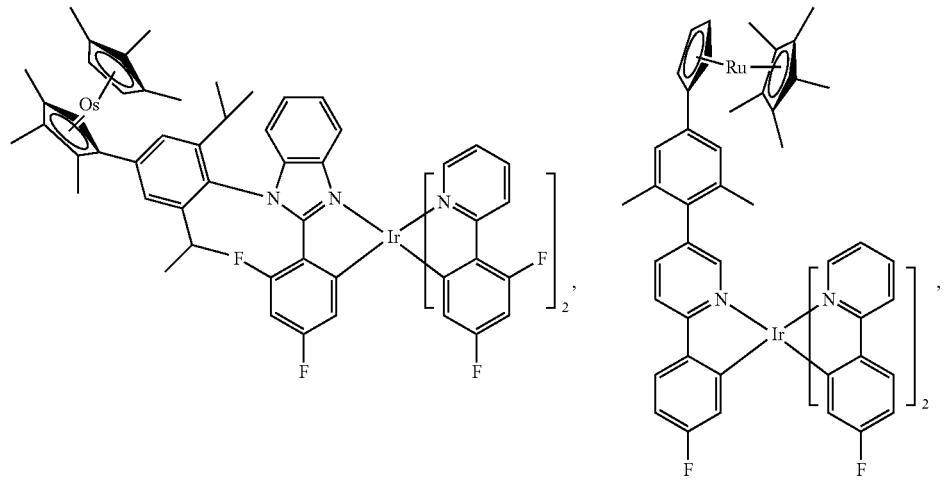
Compound 7
Compound 8
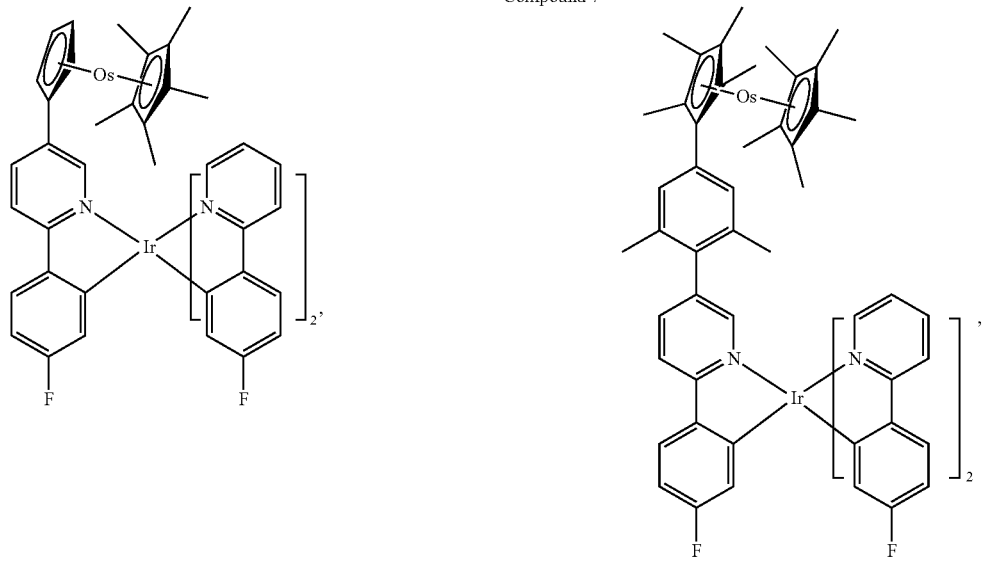
Compound 9
Compound 10
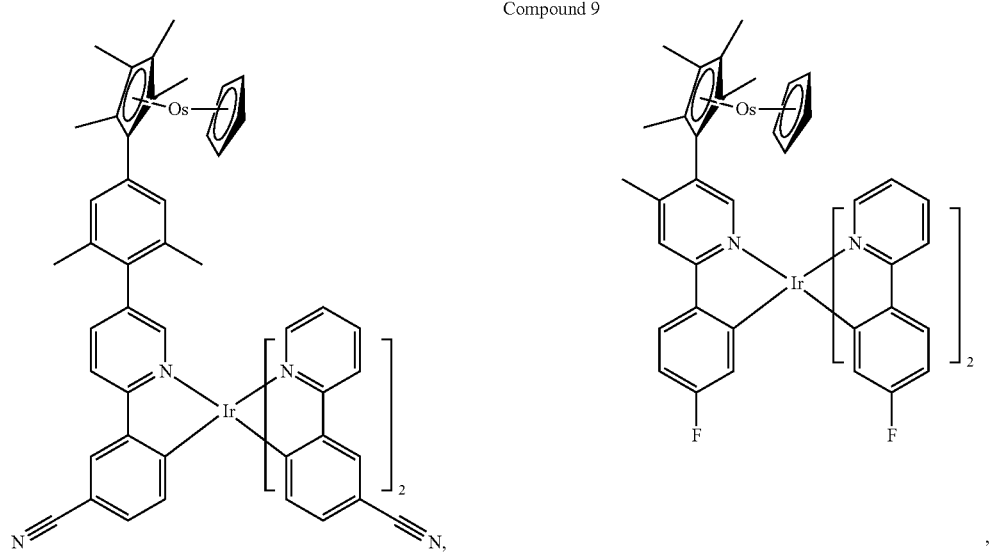

-continued
Compound 11
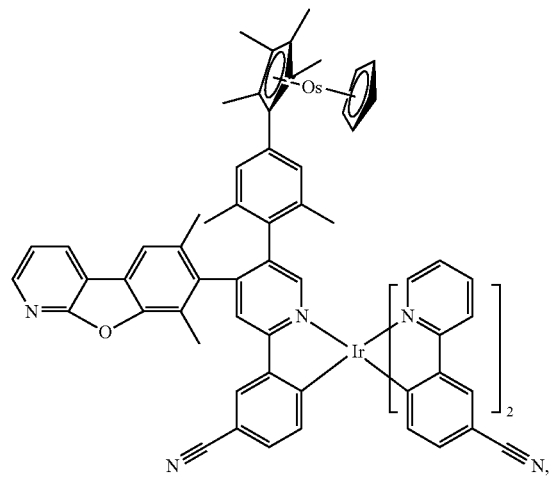
Compound 12
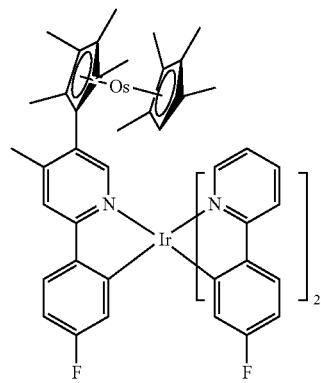
Compound 13
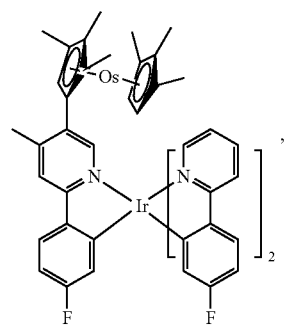
Compound 14
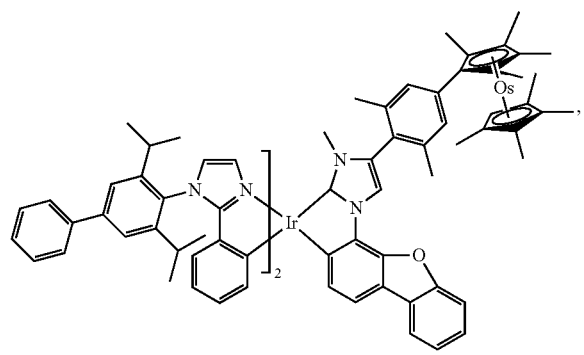
Compound 15
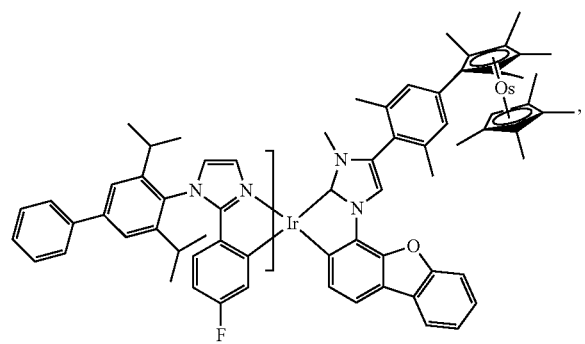
Compound 16
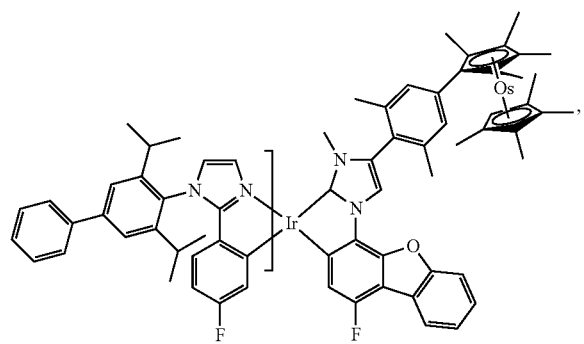

-continued
Compound 17
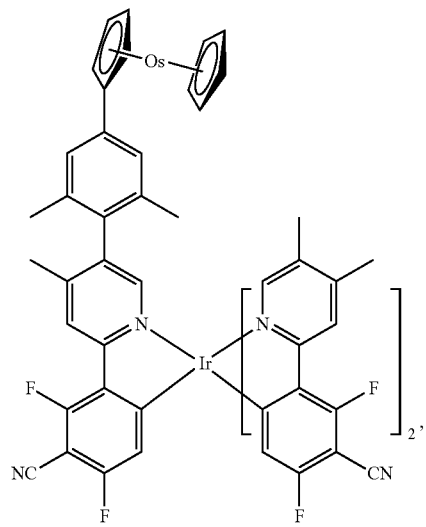
Compound 18
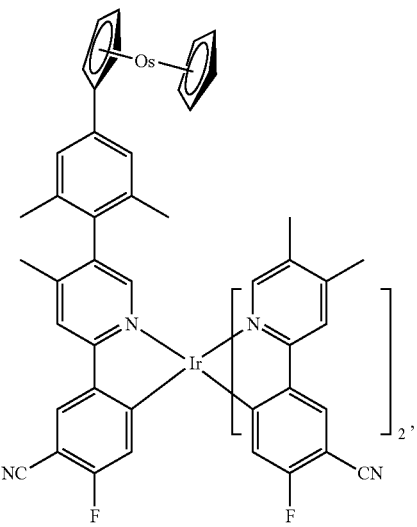
Compound 19
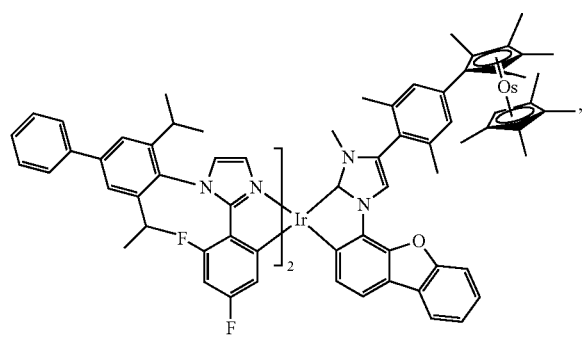
Compound 20
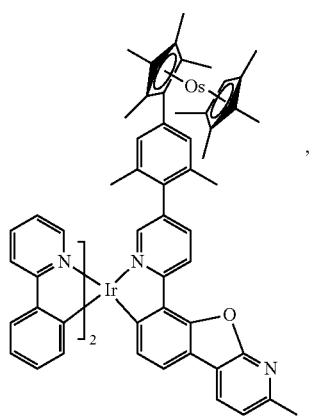
Compound 21
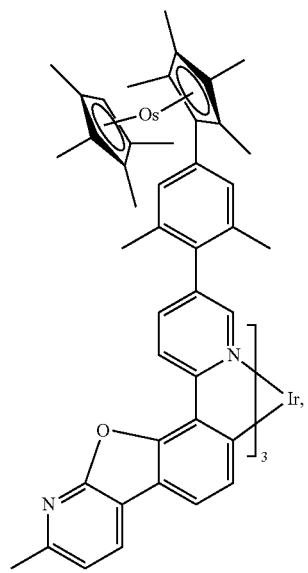
Compound 22
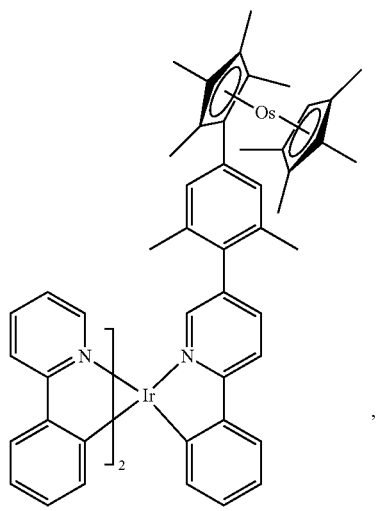

-continued
Compound 23
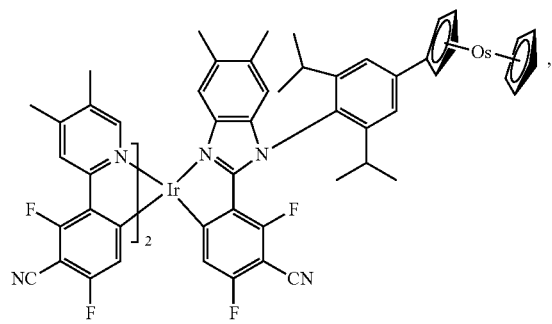
Compound 24
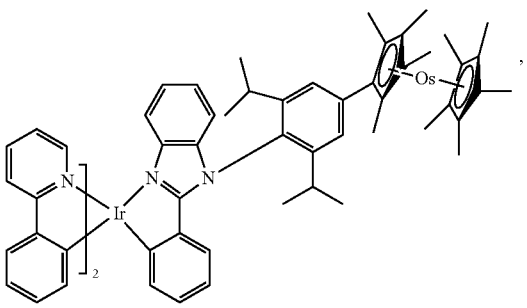
Compound 25
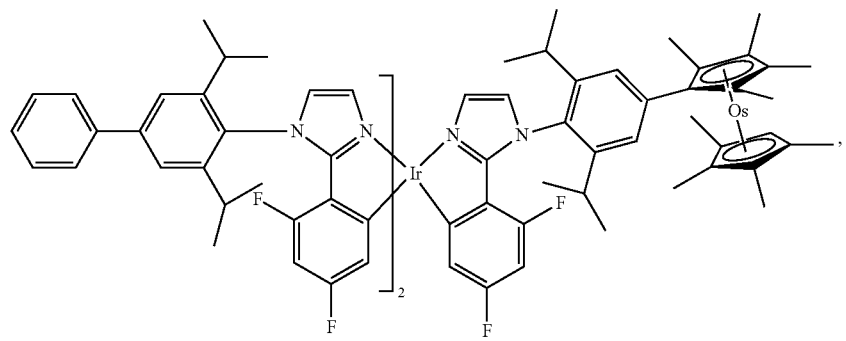
Compound 26
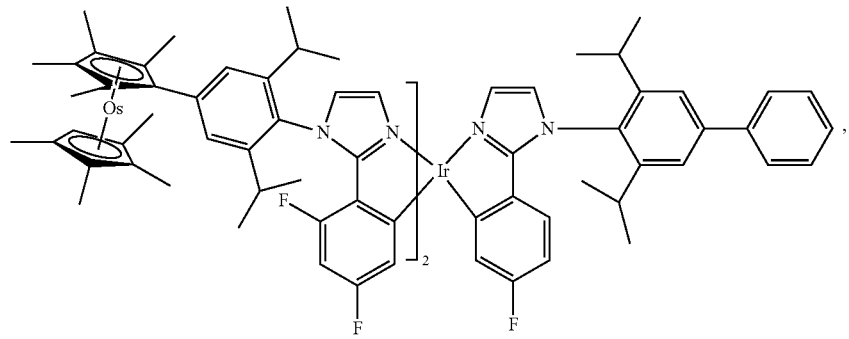
Compound 27
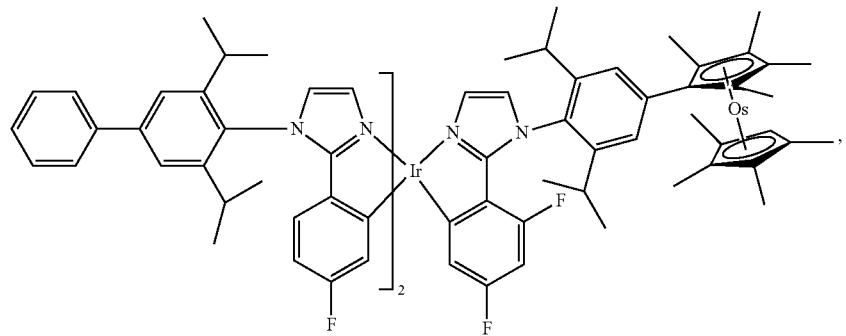
Compound 28
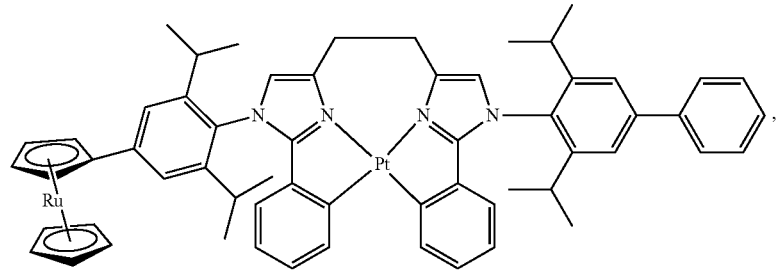

-continued
Compound 29
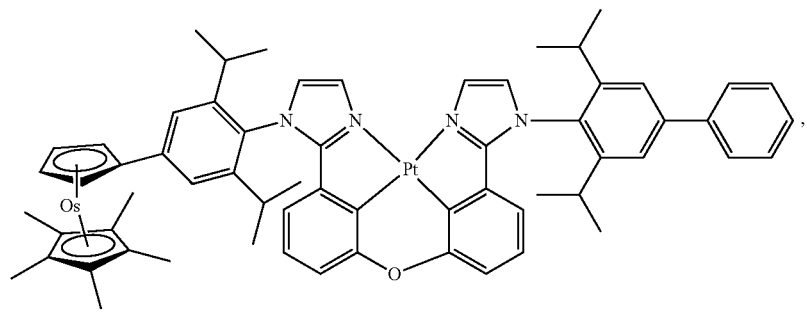
Compound 30
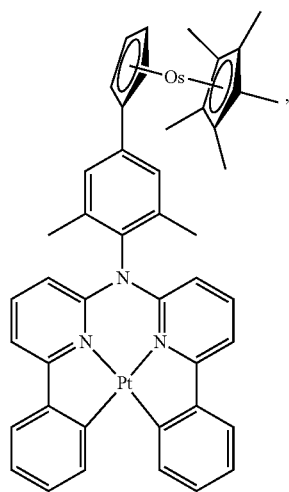
Compound 31
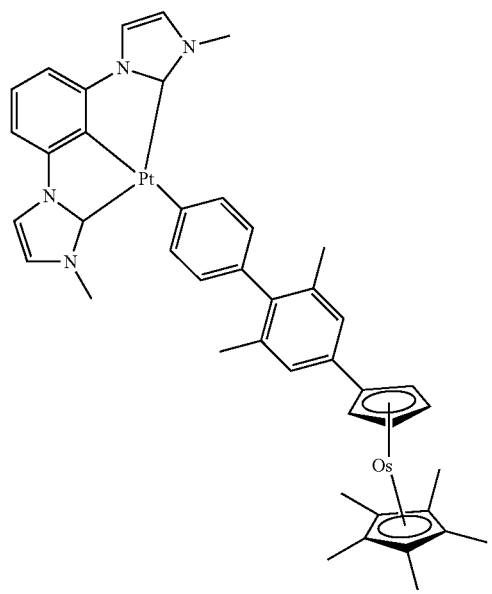
Compound 32
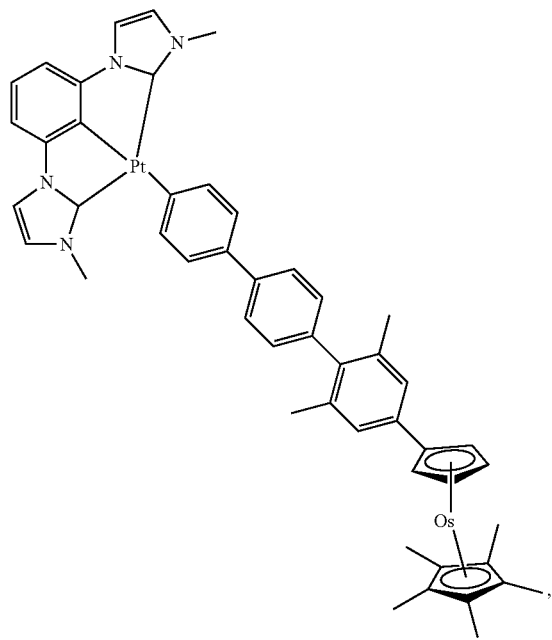
Compound 33
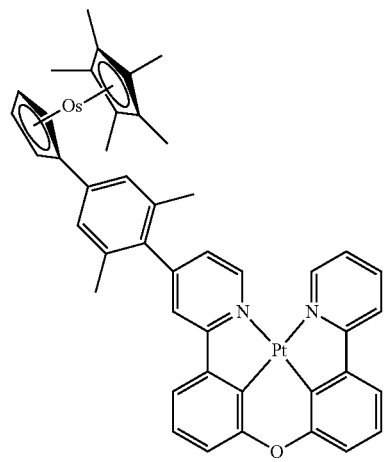

-continued
| | Compound 34 | | Compound 35 |
|---|---|---|---|
| 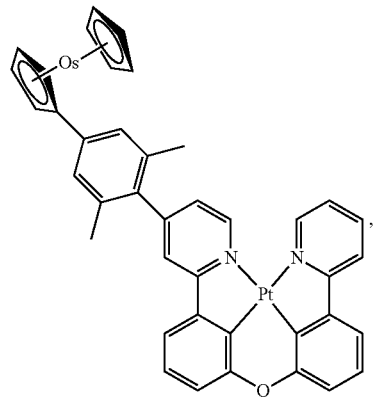 | | 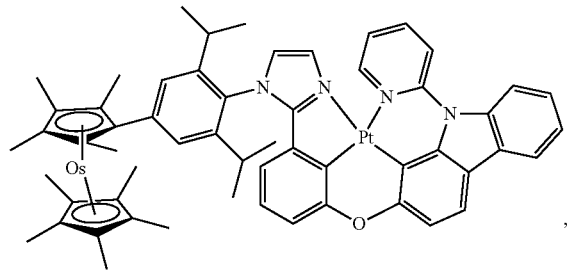 | |
| Compound 36 | | Compound 37 | |
|---|---|---|---|
| 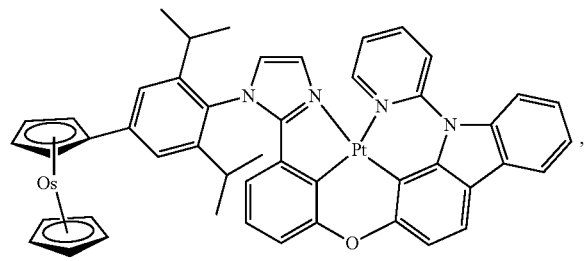, | | 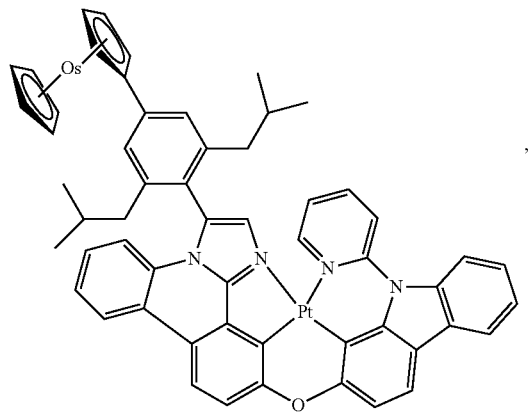, | |
| Compound 38 | | Compound 39 | |
|---|---|---|---|
| 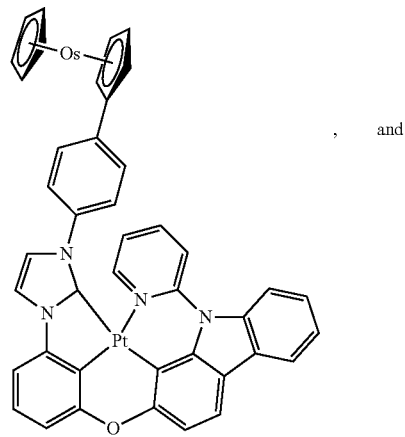, and | | 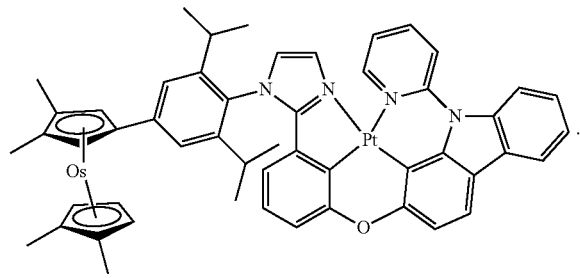. | |

According to another aspect of the present disclosure, a device comprising one or more organic light emitting devices is disclosed. At least one of the one or more organic light emitting devices comprise: an anode; a cathode; and an organic layer, disposed between the anode and the cathode, the organic layer comprising a compound comprising a first ligand $L^1$ of Formula I:

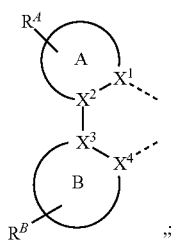

Formula I wherein ring A and ring B are each independently a 5-membered or 6-membered carbocyclic or heterocyclic ring;

wherein $X^1$, $X^2$, $X^3$, and $X^4$ are independently C or N;

wherein $R^A$ and $R^B$ each independently represent mono, di, tri, or tetra substitution, or no substitution;

wherein at least one of $R^A$ and $R^B$ has a structure according to the following formula:

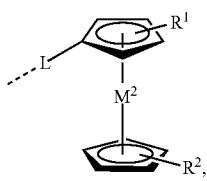

Formula II wherein L is a direct bond or a linker selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein $R^1$ represents mono, di, tri, or tetra substitution, or no substitution;

wherein $R^2$ represents mono, di, tri, tetra, or penta substitution, or no substitution;

wherein $M^2$ is selected from the group consisting of Os, Ru, and Re;

wherein $R^1$ and $R^2$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein when $R^A$ and $R^B$ is not Formula II, $R^A$ and $R^B$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any two adjacent substituents are optionally joined to form a ring, which can be further substituted;

wherein the ligand $L^1$ is coordinated to a metal M;

wherein the metal M can be coordinated to other ligands; and wherein the ligand $L^1$ is optionally linked with other ligands to comprise a tridentate, tetradentate, pentadentate or hexadentate ligand.

The device can be one or more of a consumer product, an electronic component module, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

In another embodiment, the host can be a compound comprising at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene. In some embodiments of the device, the host can include a metal complex.

In yet another embodiment, the host can be a specific compound selected from the group consisting of:

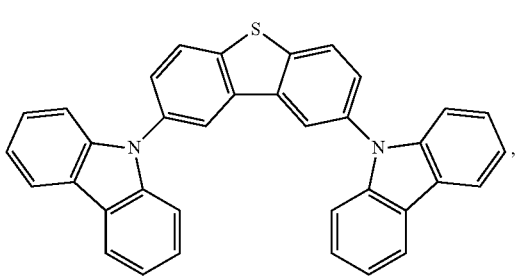

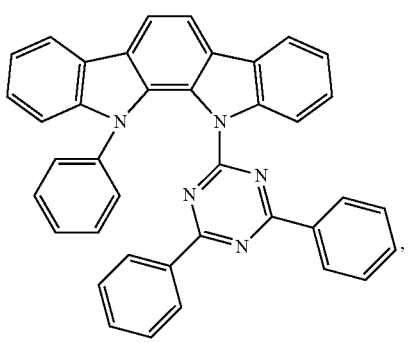

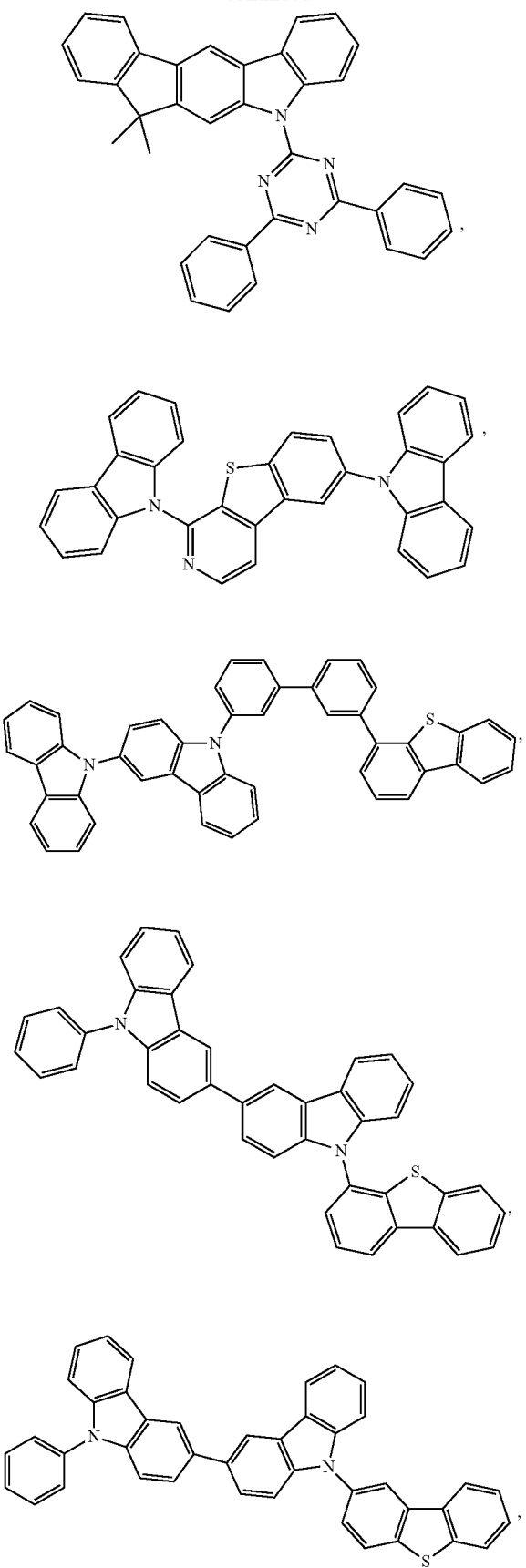
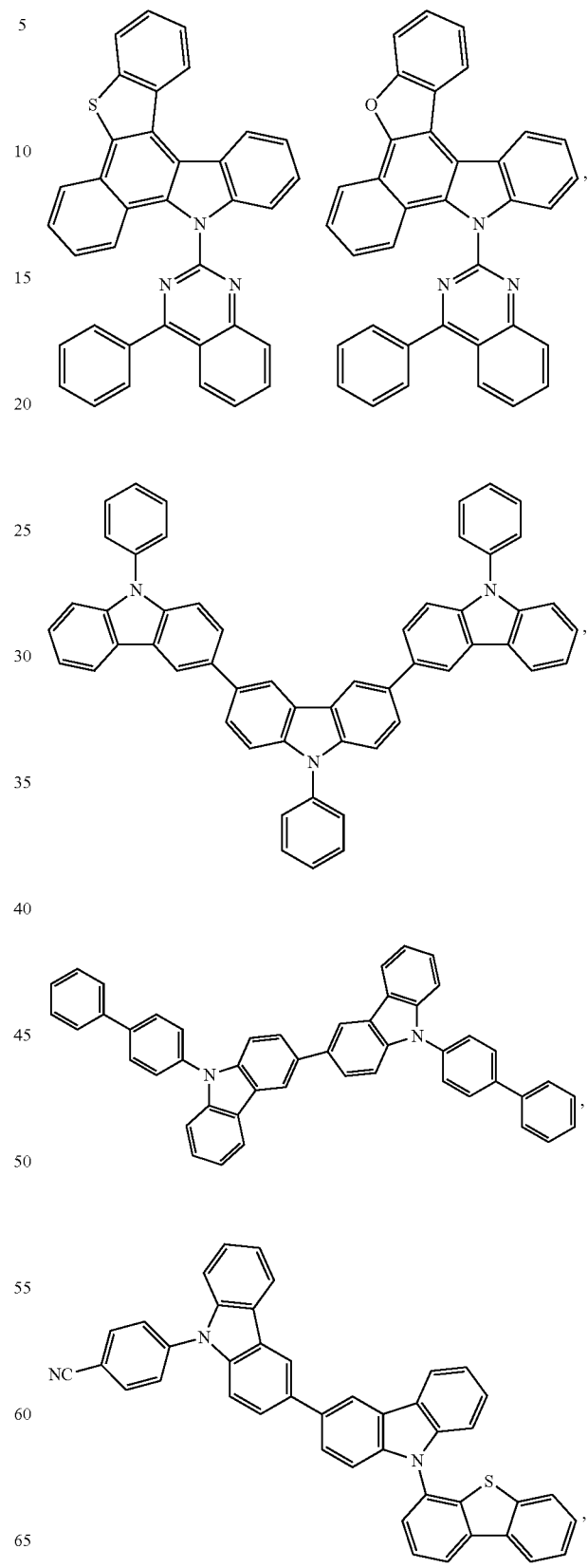

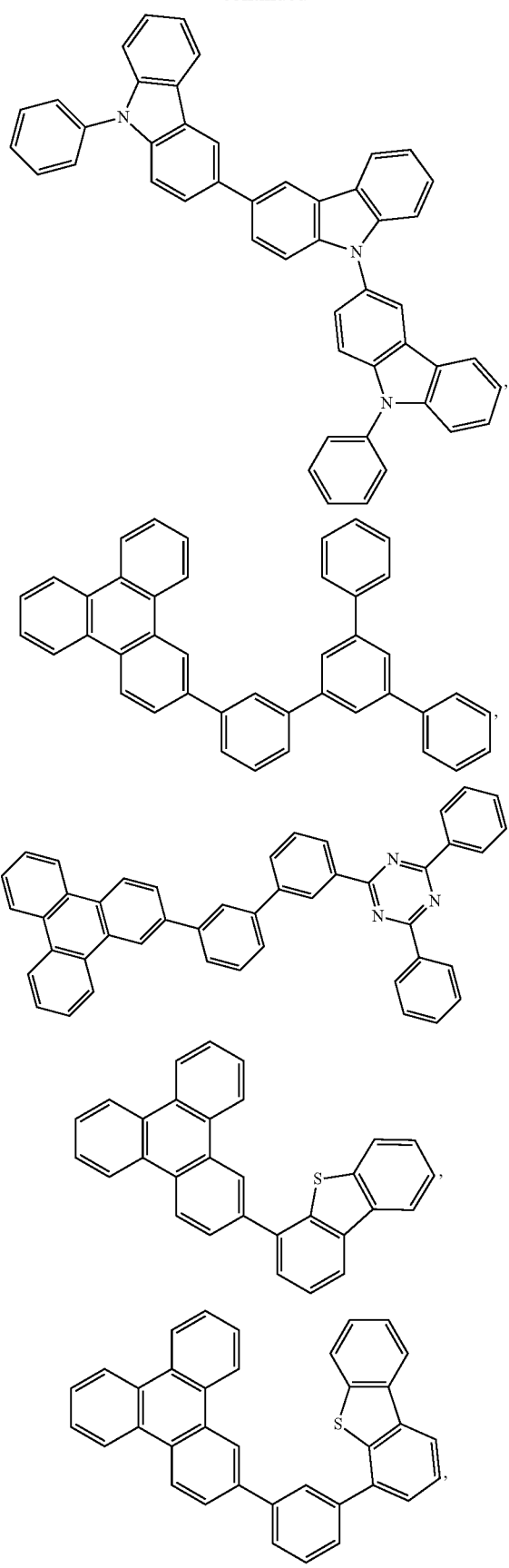
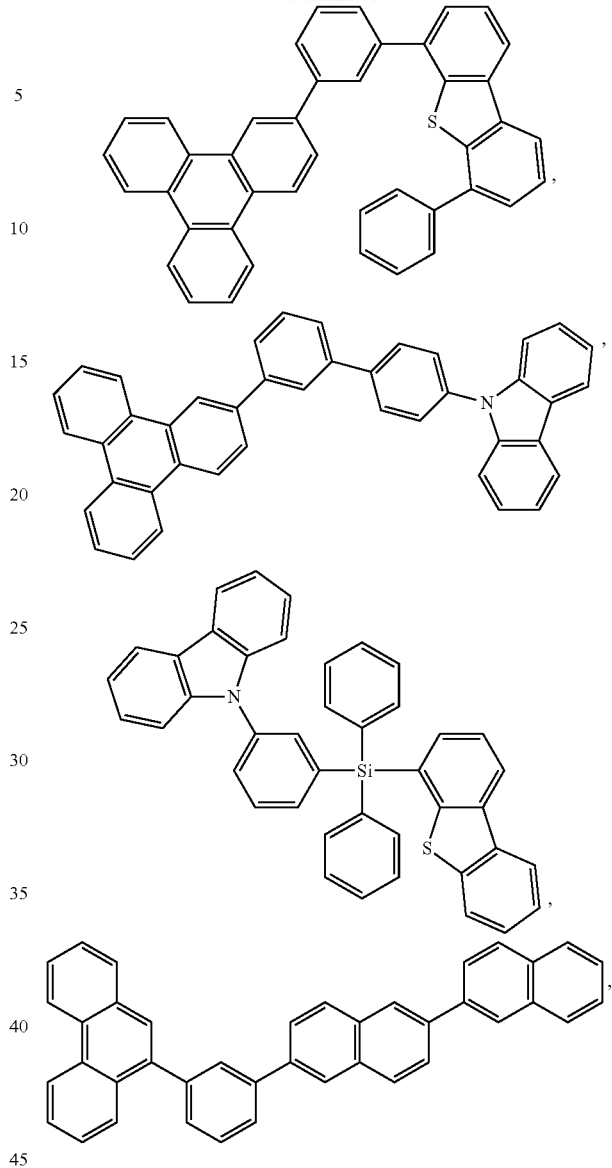
and combinations thereof.
According to another aspect of the present disclosure, a formulation comprising the compound compound comprising a first ligand L¹ of Formula I:
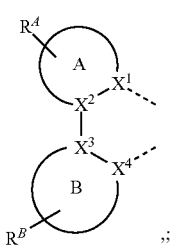
Formula I
wherein ring A and ring B are each independently a 5-membered or 6-membered carbocyclic or heterocyclic ring;

wherein $X^1$, $X^2$, $X^3$, and $X^4$ are independently C or N;

wherein $R^A$ and $R^B$ each independently represent mono, di, tri, or tetra substitution, or no substitution;

wherein at least one of $R^A$ and $R^B$ has a structure according to the following formula:

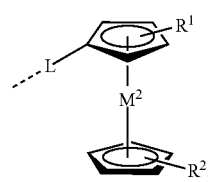

Formula II wherein L is a direct bond or a linker selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein $R^1$ represents mono, di, tri, or tetra substitution, or no substitution;

wherein $R^2$ represents mono, di, tri, tetra, or penta substitution, or no substitution;

wherein $M^2$ is selected from the group consisting of Os, Ru, and Re;

wherein $R^1$ and $R^2$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein when $R^A$ and $R^B$ is not Formula II, $R^A$ and $R^B$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any two adjacent substituents are optionally joined to form a ring, which can be further substituted;

wherein the ligand $L^1$ is coordinated to a metal M;

wherein the metal M can be coordinated to other ligands; and wherein the ligand $L^1$ is optionally linked with other ligands to comprise a tridentate, tetradentate, pentadentate or hexadentate ligand is disclosed. The formulation can include one or more components selected from the group consisting of a solvent, a host, a hole injection material, hole transport material, and an electron transport layer material, disclosed herein.

In some embodiments, the compound can be an emissive dopant in an OLED. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

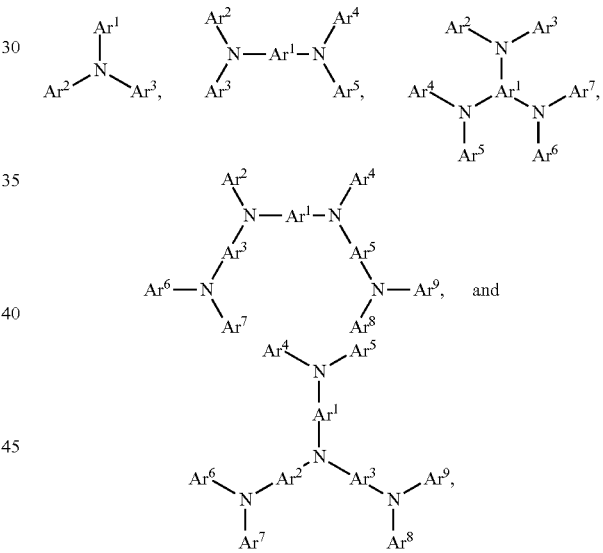

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

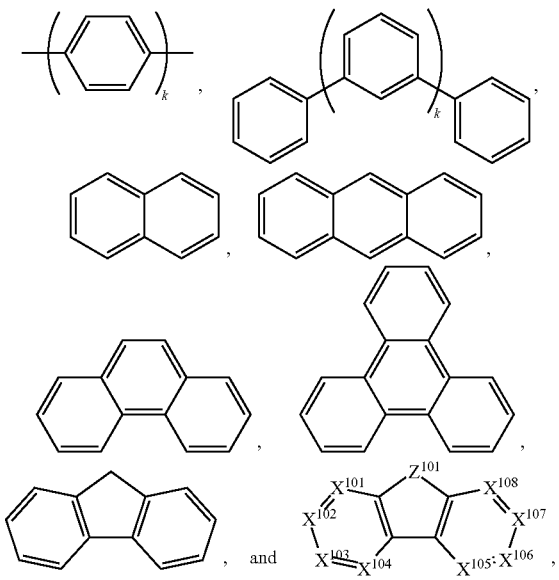

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

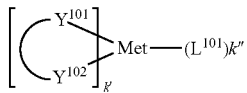

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

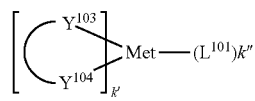

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

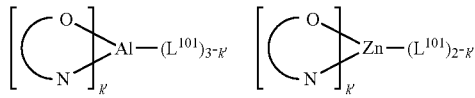

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

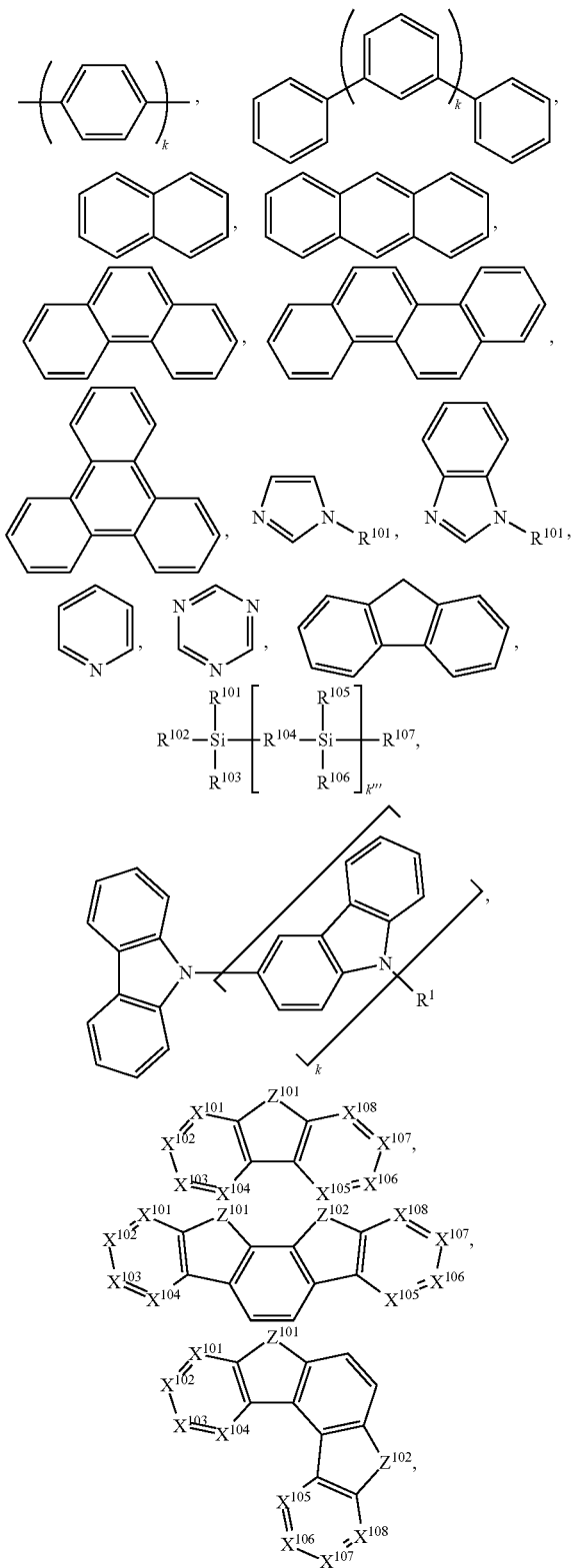

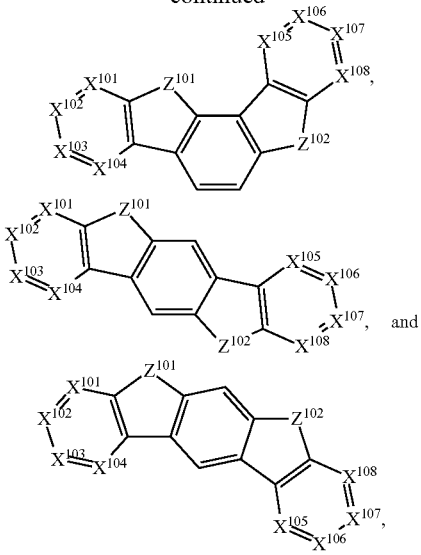

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

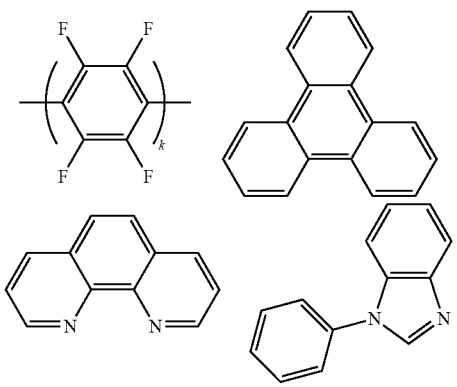

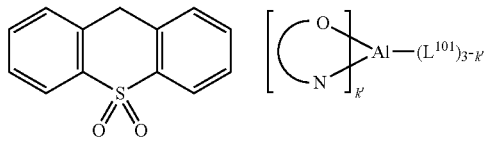

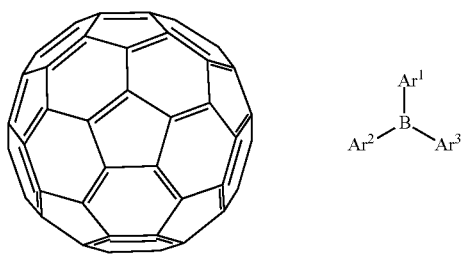

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

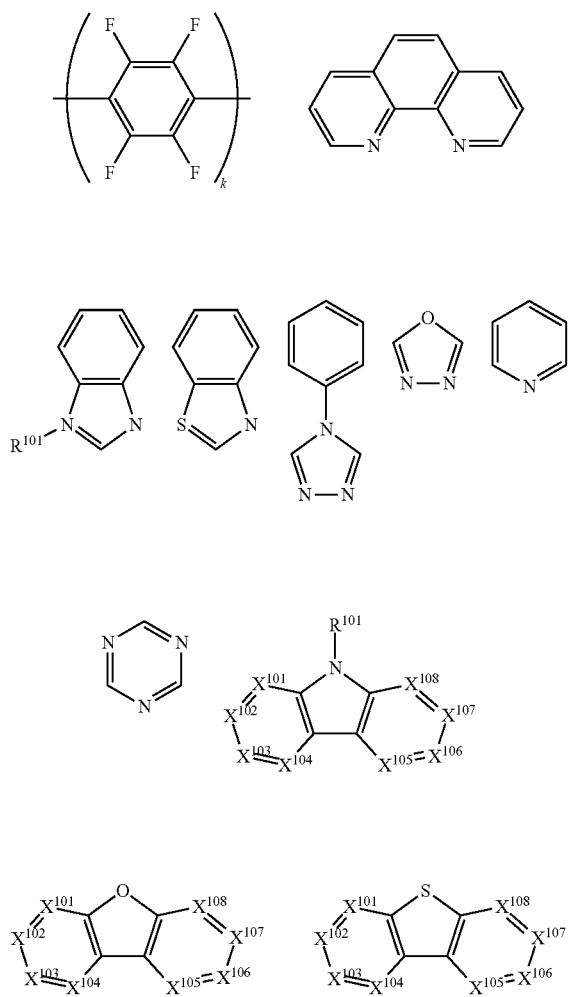

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
| --- | --- | --- |
| Hole injection materials | | |
| Phthalocyanine and porphyrin compounds | | Appl. Phys. Lett. 69, 2160 (1996) |
| Starburst triarylamines | | J. Lumin. 72-74, 985 (1997) |
| CF$_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997)<br>WO2007002683 |
| Phosphonic acid and silane SAMs | | US20030162053 |
| Triarylamine or polythiophene polymers with conductivity dopants | | EP1725079A1 |

TABLE A-continued
| MATERIAL | EXAMPLES OF MATERIAL | PUBLICATIONS |
|---|---|---|
and
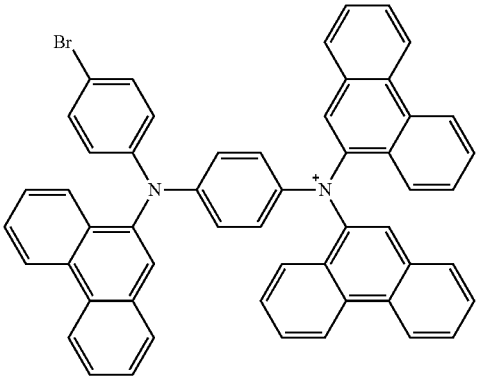 [SMILES: Brc1ccc(N(c2ccc([NH+](c3cc4ccccc4c4ccccc34)c3cc4ccccc4c4ccccc34)cc2)c2cc3ccccc3c3ccccc23)cc1]
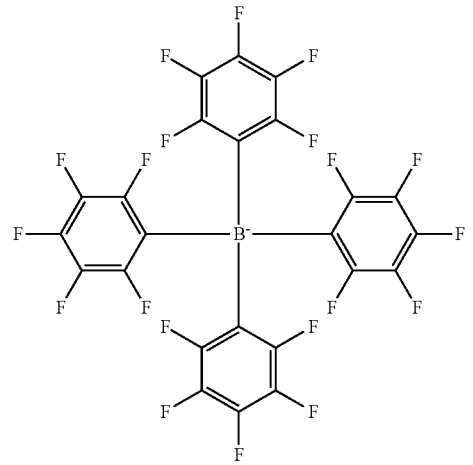 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]
| | | |
|---|---|---|
| Organic compounds with conductive inorganic compounds, such as molybdenum and tungsten oxides | 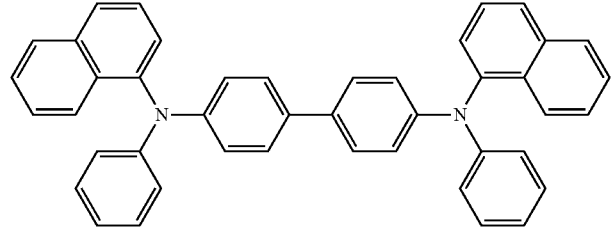 + $M^0O_x$ | US20050123751<br>SID Sumposium Digest, 37, 923 (2006)<br>WO2009018009 |
| n-type semiconducting organic complexes | 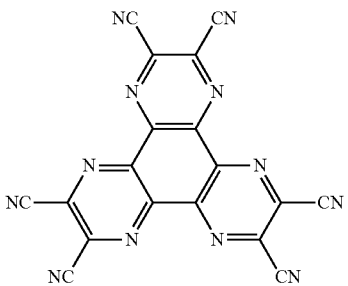 [SMILES: N#Cc1nc2c3nc(C#N)c(C#N)nc3c3nc(C#N)c(C#N)nc3c2nc1C#N] | US20020158242 |

TABLE A-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| | | |
| --- | --- | --- |
| Triarylamines<br>(e.g., TPD, α-NPD) | | Appl. Phys. Lett. 51,<br>913 (1987) |

TABLE A-continued
| MATERIAL | EXAMPLES OF MATERIAL | PUBLICATIONS |
|---|---|---|
| | | U.S. Pat. No. 5,061,569 |
| | 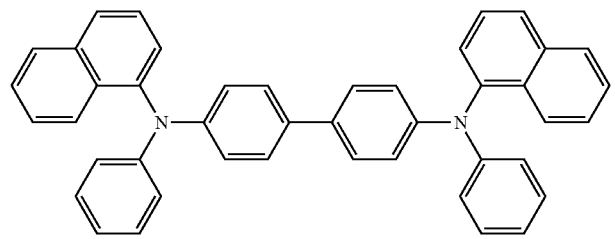 [SMILES: c1ccc(N(c2ccc(-c3ccc(N(c4ccccc4)c4cccc5ccccc45)cc3)cc2)c2cccc3ccccc23)cc1] | EP650955 |
| | 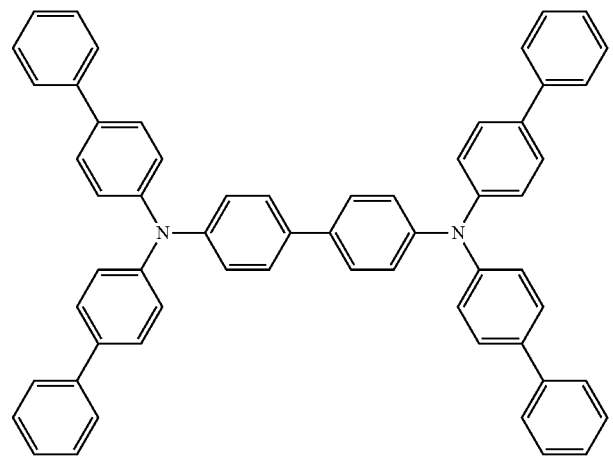 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | J. Mater. Chem. 3, 319 (1993) |
| | 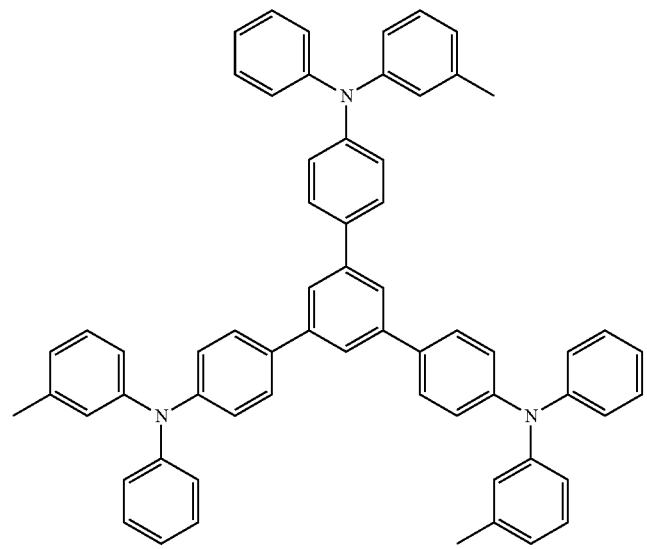 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | |

TABLE A-continued

| MATERIAL | EXAMPLES OF MATERIAL | PUBLICATIONS |
|---|---|---|
|  |  | Appl. Phys. Lett. 90, 183503 (2007) |
|  |  | Appl. Phys. Lett. 90, 183503 (2007) |
| Triarylamine on spirofluorene core |  | Synth. Met. 91, 209 (1997) |
| Arylamine carbazole compounds |  | Adv. Mater. 6, 677 (1994), US20080124572 |

TABLE A-continued
| MATERIAL | EXAMPLES OF MATERIAL | PUBLICATIONS |
|---|---|---|
| Triarylamine with (di)benzothiophene/ (di)benzofuran | 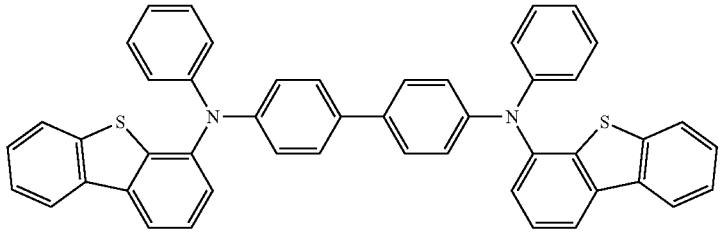 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190, US20110163302 |
| Indolocarbazoles | 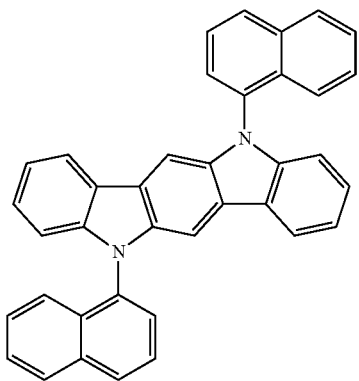 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 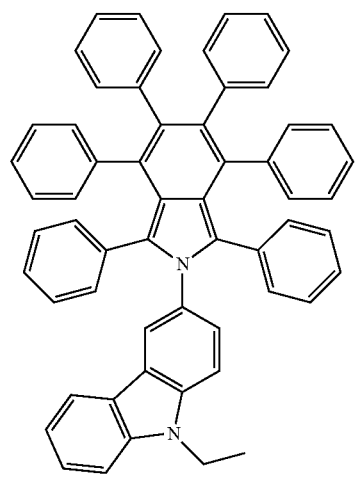 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 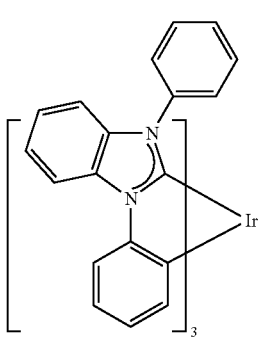 | US20080018221 |

TABLE A-continued

| MATERIAL | EXAMPLES OF MATERIAL | PUBLICATIONS |
| --- | --- | --- |
| Phosphorescent OLED host materials | | |
| Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE A-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |

TABLE A-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

| MATERIAL | EXAMPLES OF MATERIAL | PUBLICATIONS |
|---|---|---|
| | 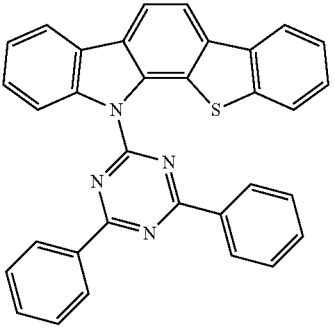 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 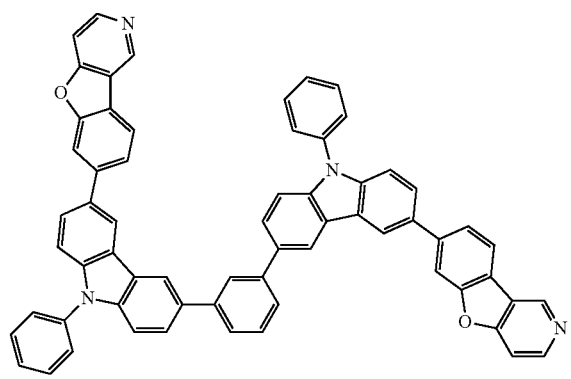 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 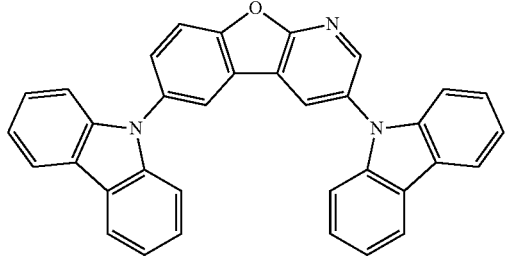 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 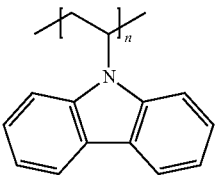 | Appl. Phys. Lett. 77, 2280 (2000) |
| Spirofluorene compounds | 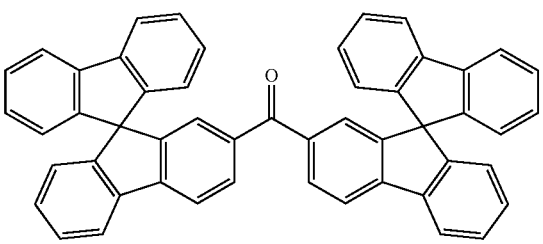 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE A-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued
| MATERIAL | EXAMPLES OF MATERIAL | PUBLICATIONS |
|---|---|---|
| Indolocarbazoles | 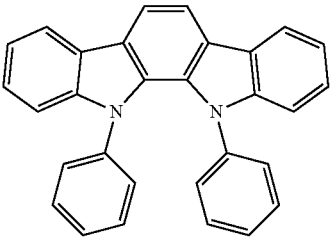 [SMILES: c1ccc(-n2c3ccccc3c3ccc4c5ccccc5n(-c5ccccc5)c4c32)cc1] | WO2007063796 |
| | 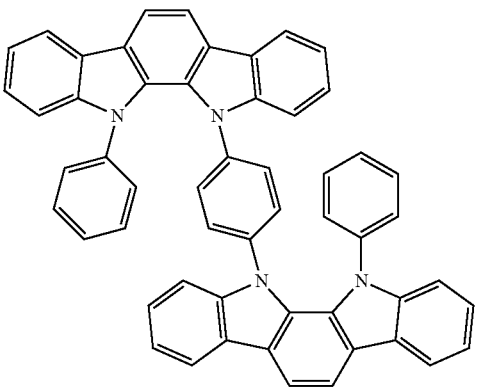 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 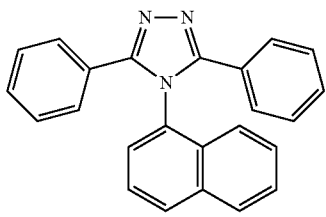 [SMILES: c1ccc(-c2nnc(-c3ccccc3)n2-c2cccc3ccccc23)cc1] | J. Appl. Phys. 90, 5048 (2001) |
| | 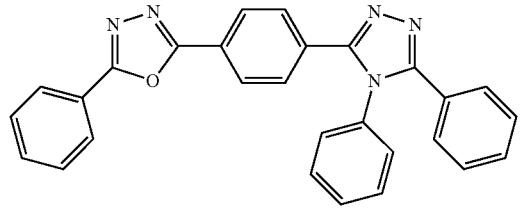 [SMILES: c1ccc(-c2nnc(-c3ccc(-c4nnc(-c5ccccc5)n4-c4ccccc4)cc3)o2)cc1] | WO2004107822 |
| Tetraphenylene complexes | 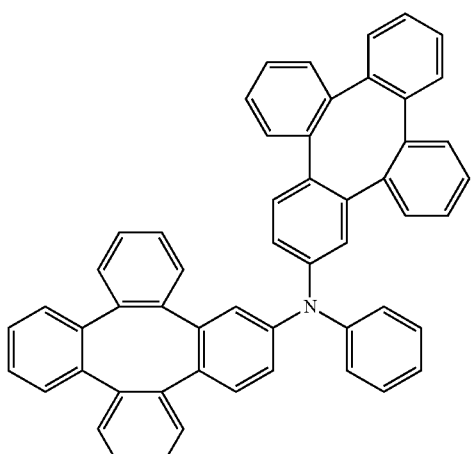 | US20050112407 |

TABLE A-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE A-continued
| MATERIAL | EXAMPLES OF MATERIAL | PUBLICATIONS |
|---|---|---|
| | 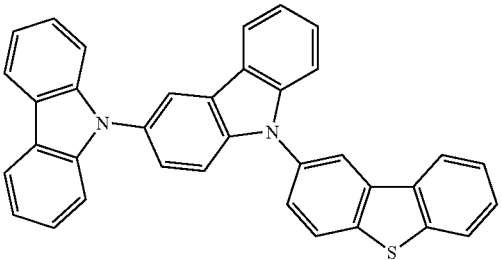 [SMILES: c1ccc2c(c1)sc1ccc(-n3c4ccccc4c4cc(-n5c6ccccc6c6ccccc65)ccc43)cc12] | WO2009086028 |
| | 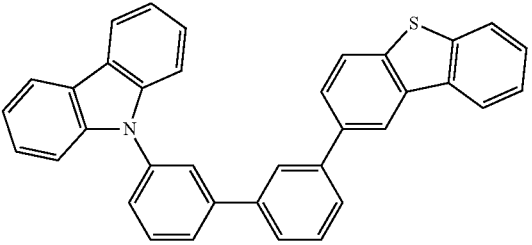 [SMILES: c1cc(-c2cccc(-n3c4ccccc4c4ccccc43)c2)cc(-c2ccc3sc4ccccc4c3c2)c1] | US20090030202, US20090017330 |
| | 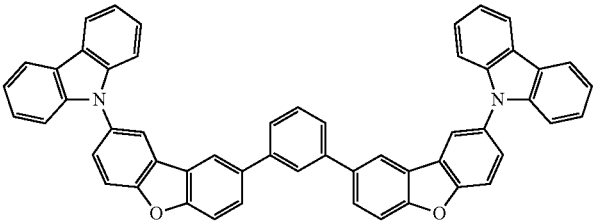 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 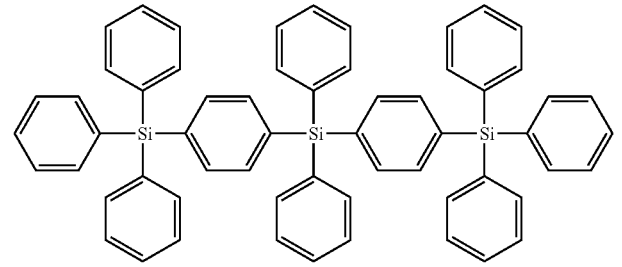 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 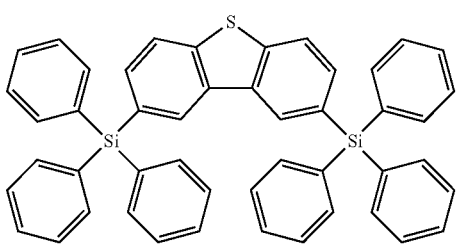 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 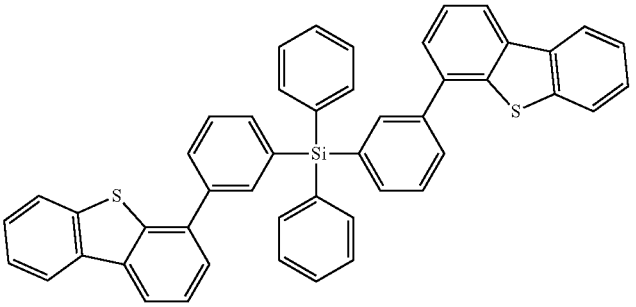 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |

TABLE A-continued

| MATERIAL | EXAMPLES OF MATERIAL | PUBLICATIONS |
| --- | --- | --- |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S Pat. No. 7,154,114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

TABLE A-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE A-continued
| MATERIAL | EXAMPLES OF MATERIAL | PUBLICATIONS |
|---|---|---|
| | 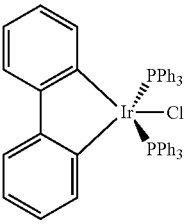 | U.S. Pat. No. 7,232,618 |
| Platinum(II) organometallic complexes | 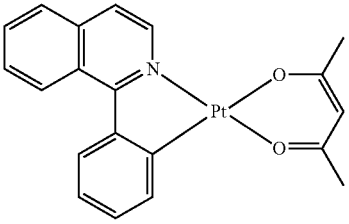 | WO2003040257 |
| | 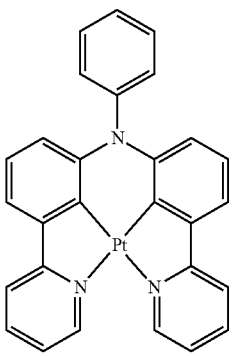 | US20070103060 |
| Osmium(III) complexes | 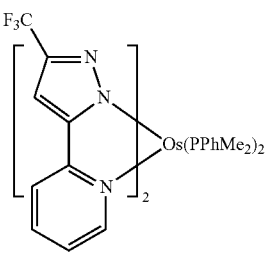 | Chem. Mater. 17, 3532 (2005) |
| Ruthenium(II) complexes | 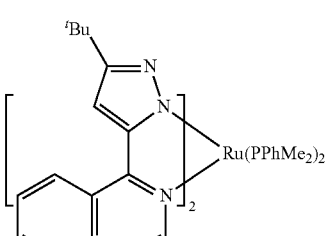 | Adv. Mater. 17, 1059 (2005) |
| Rhenium (I), (II), and (III) complexes | 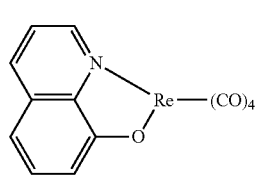 | US20050244673 |

TABLE A-continued
| MATERIAL | EXAMPLES OF MATERIAL | PUBLICATIONS |
|---|---|---|
| | Green dopants | |
| Iridium(III) organometallic complexes | 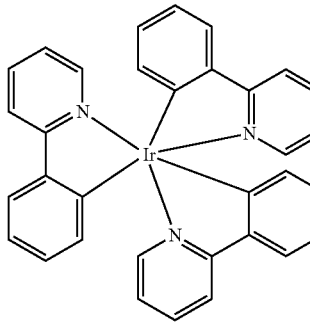<br>and its derivatives | Inorg. Chem. 40, 1704 (2001) |
| | 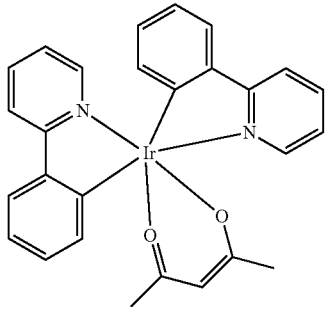 | US20020034656 |
| | 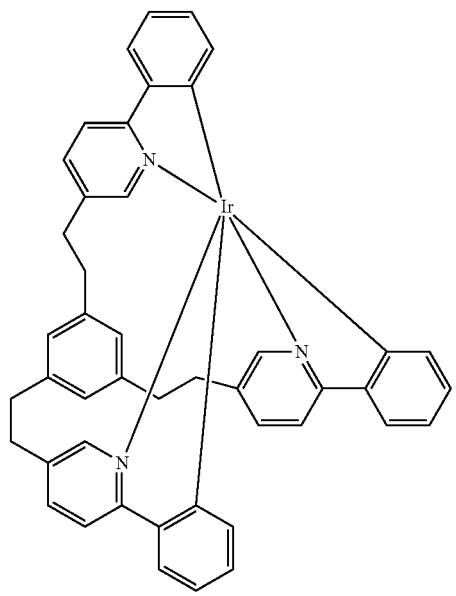 | U.S. Pat. No. 7,332,232 |

TABLE A-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE A-continued

| MATERIAL | EXAMPLES OF MATERIAL | PUBLICATIONS |
| --- | --- | --- |
| | | U.S. Pat. No. 6,921,915 |
| | | US20100244004 |
| | | U.S. Pat. No. 6,687,266 |
| | | Chem. Mater. 16, 2480 (2004) |
| | | US20070190359 |

TABLE A-continued

| MATERIAL | EXAMPLES OF MATERIAL | PUBLICATIONS |
|---|---|---|
| | | US 20060008670<br>JP2007123392 |
| | | WO2010086089,<br>WO2011144988 |
| | | Adv. Mater. 16, 2003<br>(2004) |
| | | Angew. Chem.<br>Int. Ed.<br>2006, 45, 7800 |
| | | WO2009050290 |
| | | US20090165846 |

TABLE A-continued
| MATERIAL | EXAMPLES OF MATERIAL | PUBLICATIONS |
|---|---|---|
| | 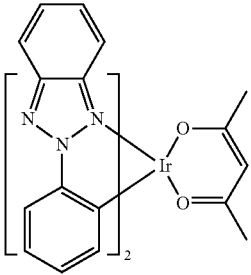 | US20080015355 |
| | 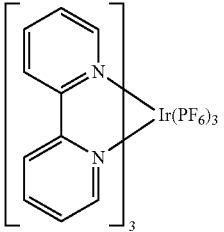 | US20010015432 |
| | 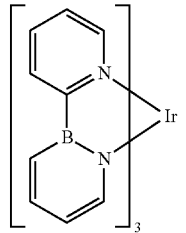 | US20100295032 |
| Monomer for polymeric metal organometallic compounds | 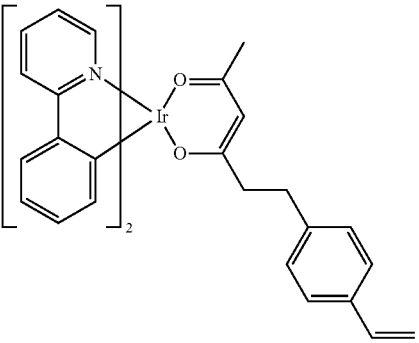 | U.S. Pat. No. 7,250,226, U.S. Pat. No. 7,396,598 |
| Pt(II) organometallic complexes, including polydentate ligands | 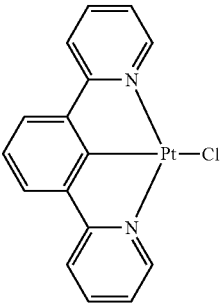 | Appl. Phys. Lett. 86, 153505 (2005) |

TABLE A-continued
| MATERIAL | EXAMPLES OF MATERIAL | PUBLICATIONS |
|---|---|---|
| | 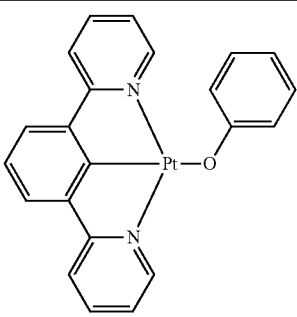 | Appl. Phys. Lett. 86, 153505 (2005) |
| | 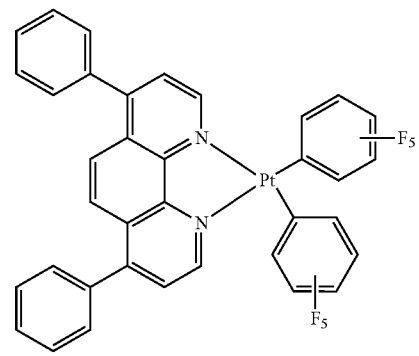 | Chem. Lett. 34, 592 (2005) |
| | 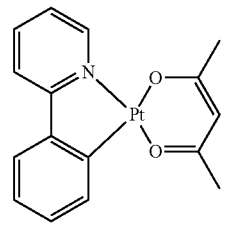 | WO2002015645 |
| | 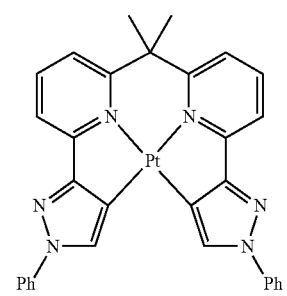 | US20060263635 |
| | 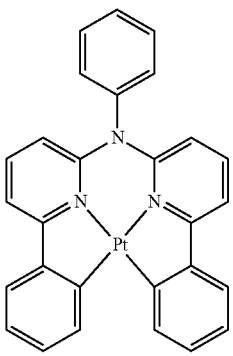 | US20060182992<br>US20070103060 |

TABLE A-continued
| MATERIAL | EXAMPLES OF MATERIAL | PUBLICATIONS |
|---|---|---|
| Cu complexes | 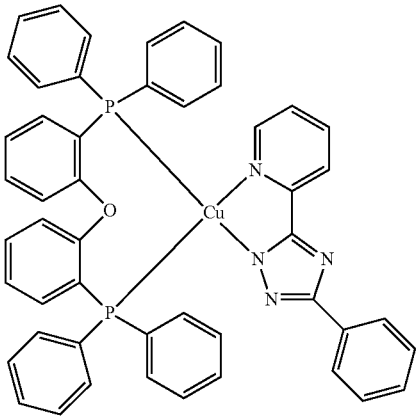 | WO2009000673 |
| | 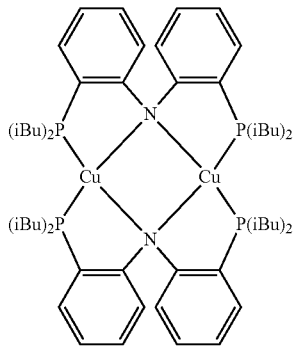 | US20070111026 |
| Gold complexes | 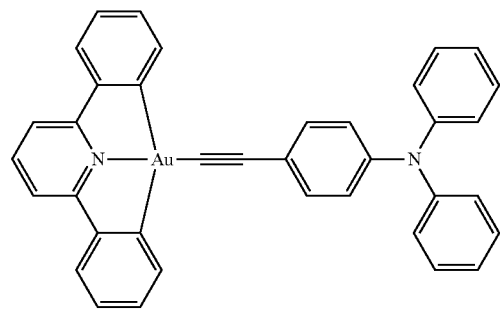 | Chem. Commun. 2906 (2005) |
| Rhenium(III) complexes | 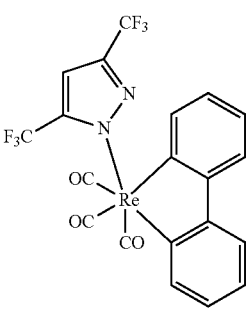 | Inorg. Chem. 42, 1248 (2003) |

TABLE A-continued

| MATERIAL | EXAMPLES OF MATERIAL | PUBLICATIONS |
|---|---|---|
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE A-continued
| MATERIAL | EXAMPLES OF MATERIAL | PUBLICATIONS |
| --- | --- | --- |
| Blue dopants | | |
| Iridium(III) organometallic complexes | 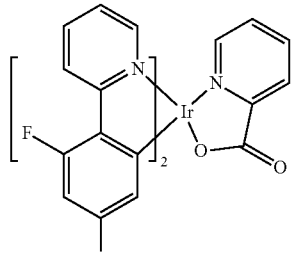 | WO2002002714 |
| | 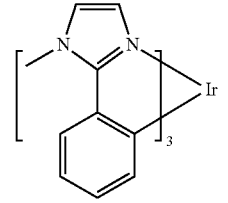 | WO2006009024 |
| | 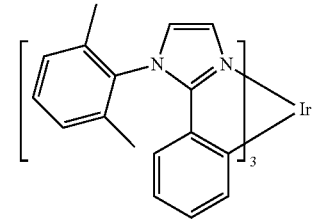 | US20060251923<br>US20110057559<br>US20110204333 |
| | 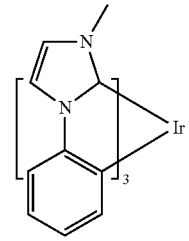 | U.S. Pat. No. 7,393,599,<br>WO2006056418,<br>US20050260441,<br>WO2005019373 |
| | 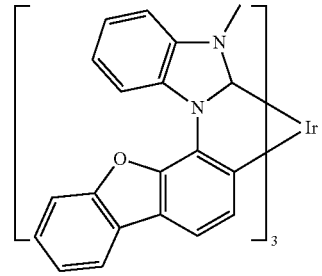 | U.S. Pat. No. 7,534,505 |
| | 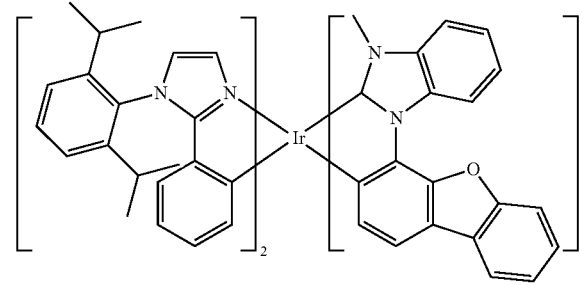 | WO2011051404 |

TABLE A-continued

| MATERIAL | EXAMPLES OF MATERIAL | PUBLICATIONS |
|---|---|---|
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 4542 (2008) |

TABLE A-continued
| MATERIAL | EXAMPLES OF MATERIAL | PUBLICATIONS |
|---|---|---|
| | 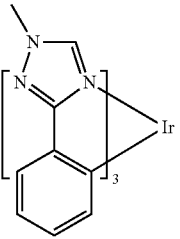 | Chem. Mater. 18, 5119 (2006) |
| | 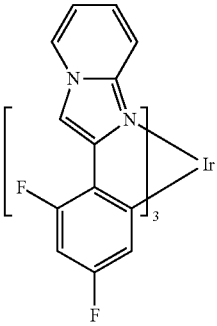 | Inorg. Chem. 46, 4308 (2007) |
| | 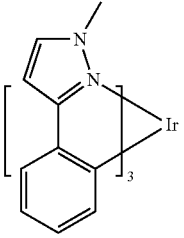 | WO2005123873 |
| | 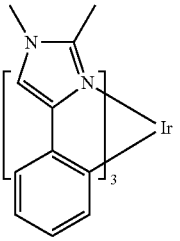 | WO2005123873 |
| | 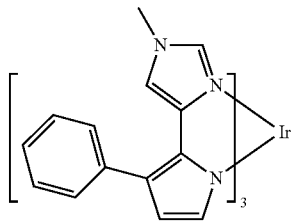 | WO2007004380 |

TABLE A-continued
| MATERIAL | EXAMPLES OF MATERIAL | PUBLICATIONS |
| --- | --- | --- |
| | 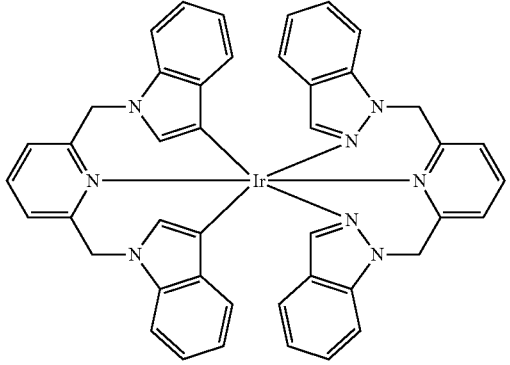 | WO2006082742 |
| Osmium(II) complexes | 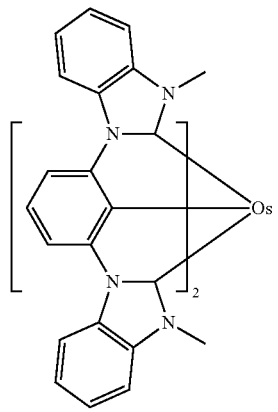 | U.S. Pat. No. 7,279,704 |
| | 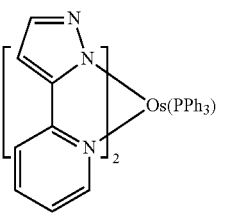 | Organometallics 23, 3745 (2004) |
| Gold complexes | 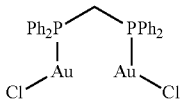 | Appl. Phys. Lett. 74, 1361 (1999) |
| Platinum(II) complexes | 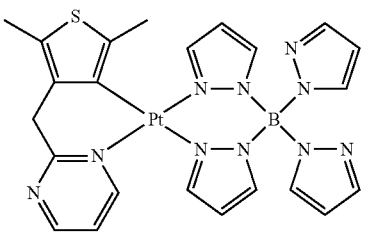 | WO2006098120, WO2006103874 |

TABLE A-continued

| MATERIAL | EXAMPLES OF MATERIAL | PUBLICATIONS |
|---|---|---|
| Pt tetradentate complexes with at least one metal-carbene bond | 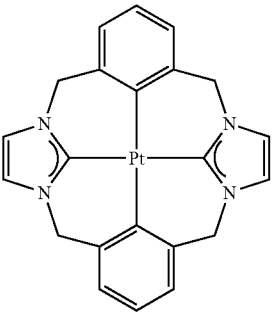 | U.S. Pat. No. 7,655,323 |
| Exciton/hole blocking layer materials | | |
| Bathocuproine compounds (e.g., BCP, BPhen) | 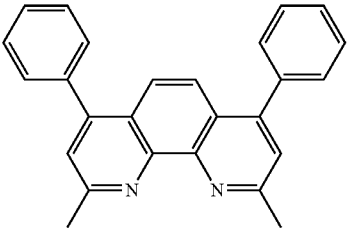 [SMILES: Cc1cc(-c2ccccc2)c2ccc3c(-c4ccccc4)cc(C)nc3c2n1] | Appl. Phys. Lett. 75, 4 (1999) |
| | 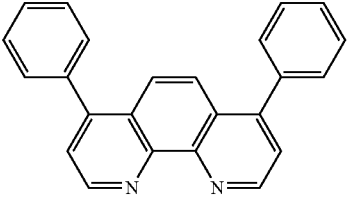 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 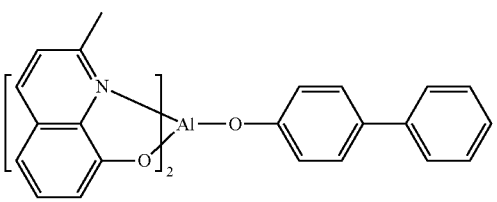 | Appl. Phys. Lett. 81, 162 (2002) |
| 5-member ring electron deficient heterocycles such as triazole, oxadiazole, imidazole, benzoimidazole | 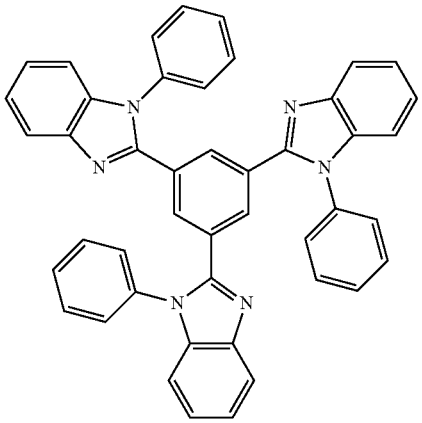 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE A-continued

| MATERIAL | EXAMPLES OF MATERIAL | PUBLICATIONS |
| --- | --- | --- |
| Triphenylene compounds | | US20050025993 |
| Fluorinated aromatic compounds | | Appl Phys Lett 79, 156 (2001) |
| Phenothiazine-S-oxide | | WO2008132085 |
| Silylated five-membered nitrogen, oxygen, sulfur or phosphorus dibenzoheterocycles | | WO2010079051 |

TABLE A-continued
| MATERIAL | EXAMPLES OF MATERIAL | PUBLICATIONS |
|---|---|---|
| Aza-carbazoles | 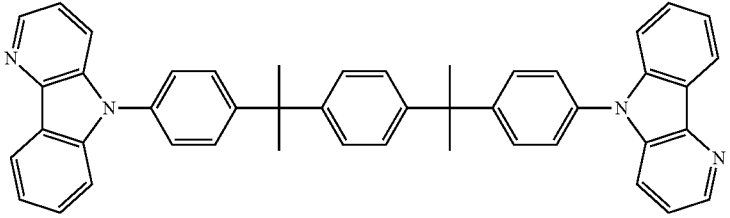 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 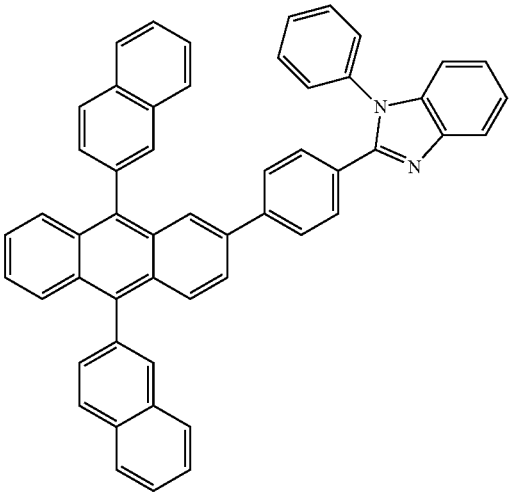 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 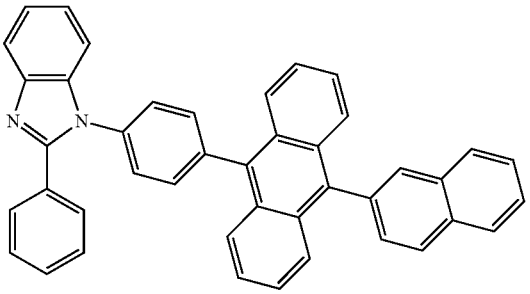 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 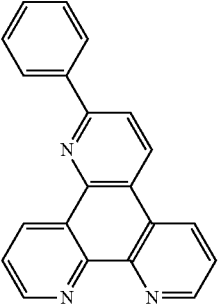 [SMILES: c1ccc(-c2ccc3c4cccnc4c4ncccc4c3n2)cc1] | US20090115316 |
| Anthracene-benzothiazole compounds | 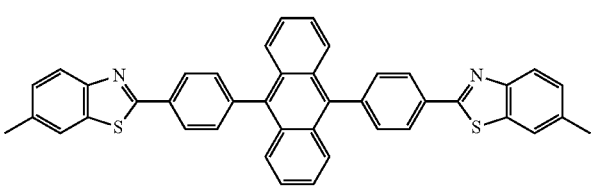 | App. Phys. Lett. 89, 063504 (2006) |

TABLE A-continued

| MATERIAL | EXAMPLES OF MATERIAL | PUBLICATIONS |
| --- | --- | --- |
| Metal 8-hydroxyquinolates (e.g., $Alq_3$, $Zrq_4$) | | Appl. Phys. Lett. 51, 913 (1987) U.S. Pat. No. 7,230,107 |
| Metal hydroxybenzoquinolates | | Chem. Lett. 5, 905 (1993) |
| Bathocuproine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | App. Phys. Lett. 55, 1489 (1989) |

TABLE A-continued
| MATERIAL | EXAMPLES OF MATERIAL | PUBLICATIONS |
|---|---|---|
| | 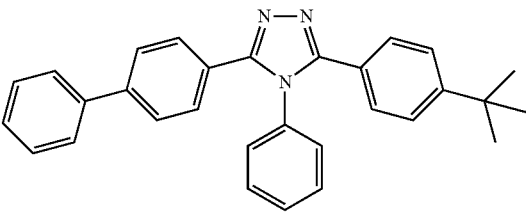 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 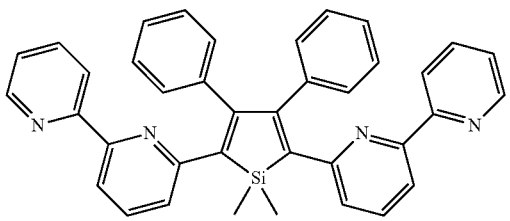 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 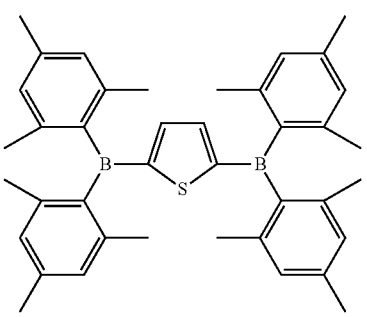 | J. Am. Chem. Soc. 120, 9714 (1998) |
| Fluorinated aromatic compounds | 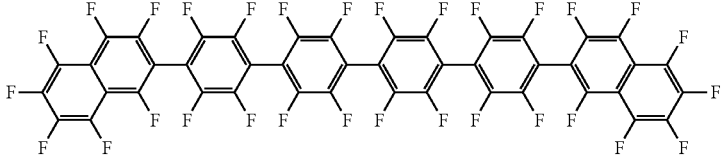 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 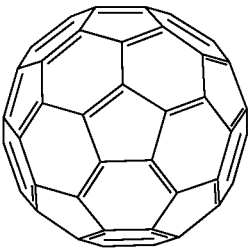 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 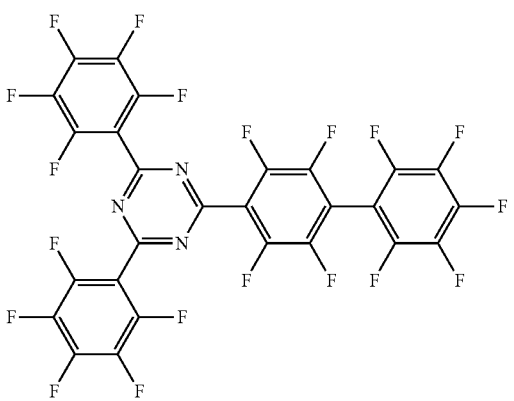 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE A-continued

| MATERIAL | EXAMPLES OF MATERIAL | PUBLICATIONS |
|---|---|---|
| Zn (N^N) complexes | | U.S. Pat. No. 6,528,187 |

Inventors believe that the disclosed phosphorescent dopants having the general structure represented by Formula I described herein have beneficially small electrochemical band gap while maintaining the triplet energy. The inventors have determined that the linkage of a pendant redox-active ligand to a conjugated system would allow the electrochemical gap of the whole molecule to be modulated without altering the optical property. Table 1 shows the calculated HOMO, LUMO, and electrochemical gap for inventive compounds Compound 8 and Compound 1 and the comparative compounds Compound A and Compound B. Compound A and Compound 8 have the same triplet energy, but Compound 8 has a shallower HOMO than Compound A because of the pendant osmocene group on Compound 8. As a result, Compound 8 has a smaller electrochemical gap than Compound A (3.30 eV vs. 3.65 eV). Likewise, Compound 1 has the same triplet energy as Compound B, but Compound 1 has a smaller electrochemical gap than Compound B because of the pendant osmocene group on Compound 1. Phosphorescent dopants, such as the novel compounds represented by compounds 8 and 1 with a smaller electrochemical gap is highly desirable for OLED application.

Smaller electrochemical gap is believed to provide better stability toward charges. In addition, shallower HOMO and deeper LUMO energy levels can provide charge trapping sites and confinement of triplet energy on the emitter, which can result in high device efficiency. For most of the phosphorescent emitters, the electrochemical gap is correlated to the optical bandgap. Emitters having higher optical bandgap usually have larger electrochemical bandgap. This is one of the reasons that blue phosphorescent devices have short device lifetime. The current invention provides a way to maintain the optical bandgap while shrinking the electrochemical gap. As a result, the current invention provides more stable phosphorescent emitters.

TABLE 1

Calculated HOMO/LUMO levels

| | HOMO (eV) | LUMO (eV) | Gap (eV) | T1 |
|---|---|---|---|---|
| 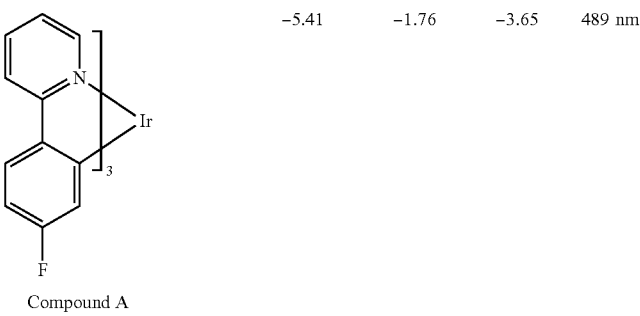 | −5.41 | −1.76 | −3.65 | 489 nm |

Compound A

TABLE 1-continued
| | Calculated HOMO/LUMO levels | | | |
|---|---|---|---|---|
| | HOMO (eV) | LUMO (eV) | Gap (eV) | T1 |
| 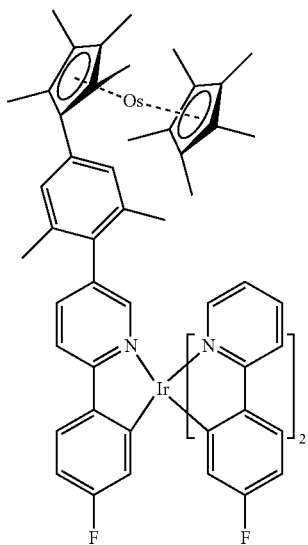Compound 8 | −5.01 | −1.71 | −3.30 | 489 nm |
| 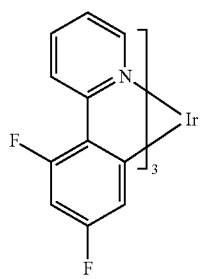Compound B | −5.85 | −2.07 | −3.79 | 472 nm |
| 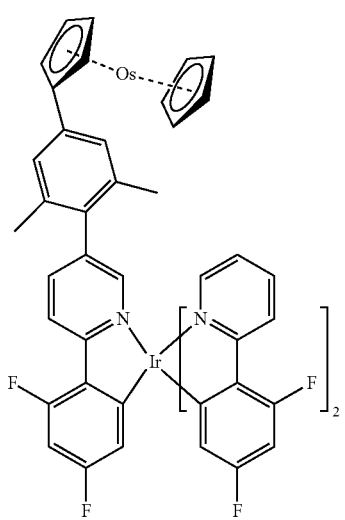Compound 1 | −5.54 | −1.94 | −3.60 | 471 nm |

Synthesis

Synthesis of Compound 1

Synthesis of 2-(4-chloro-2,6-dimethylphenyl)-4,4,5,5-tetramethyl-1,3,2-dioxaborolane

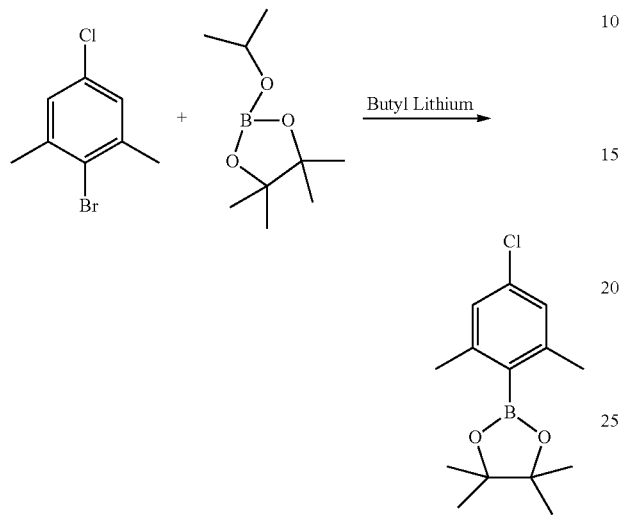

A 500 ml round bottom flask was charged with 1-bromo-4-isopropylbenzene (13.5 g, 67.8 mmol) and 200 mL of THF. N-butyllithium in hexane (2.5M, 32.5 ml, 81 mmol) was added dropwise to the reaction mixture at −78° C. The reaction mixture was then stirred at −78° C. for 45 minutes. 2-isopropoxy-4,4,5,5-tetramethyl-1,3,2-dioxaborolane (20.19 g, 108 mmol) in 20 mL of THF was then added to the reaction mixture dropwise at −78° C. The reaction mixture was stirred and allowed to slowly warm to room temperature (20-25° C.). The reaction mixture was quenched with aqueous ammonium chloride then was extracted 2×300 mL ethyl acetate. These extracts were combined and were washed with aqueous LiCl. The extracts were then combined and passed through a 400 g silica gel column using 20% DCM/heptanes as the eluent and yielded the desired compound, 2-(4-chloro-2,6-dimethylphenyl)-4,4,5,5-tetramethyl-1,3,2-dioxaborolane, (14.3 g, 93%).

Synthesis of
5-bromo-2-(2,4-difluorophenyl)pyridine

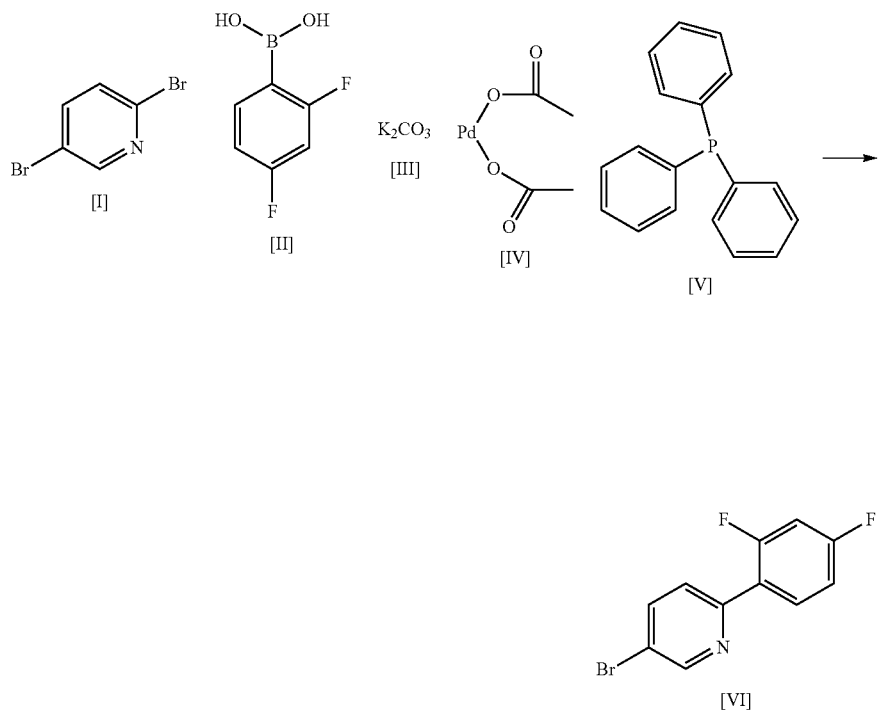

One 1.0 L round bottom flask was charged with 2,5-dibromopyridine (10.45 g, 44.1 mmol); (2,4-difluorophenyl)boronic acid (7.66 g, 48.5 mmol); potassium carbonate (12.19 g, 88 mmole); diacetoxypalladium (0.495 g, 2.206 mmol); triphenylphosphine (1.157 g, 4.41 mmol); and acetonitrile (348 ml) and MeOH (174 ml). The reaction mixture was heated to 40° C. for 40 hours. The reaction mixture was diluted with deionized water and extracted with ethyl acetate. The organic portion was combined and subjected to column chromatography (SiO$_2$ gel, 10% EtOAc in heptane) to yield the desired compound, 5-bromo-2-(2,4-difluorophenyl)pyridine (10 g; 84%).

Synthesis of 5-(4-chloro-2,6-dimethylphenyl)-2-(2,4-difluorophenyl)pyridine

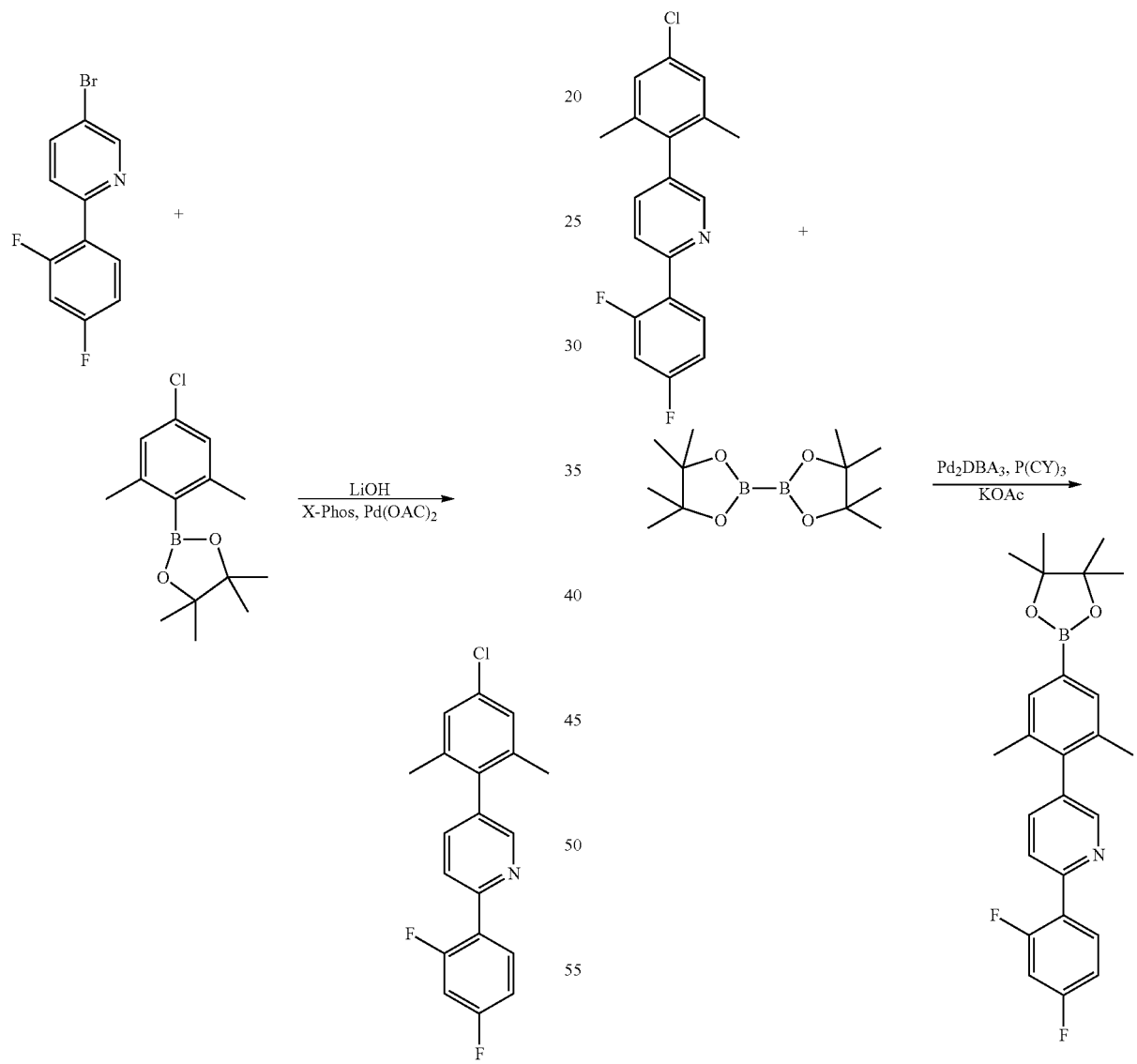

One 100 mL round-bottomed flask was charged with 5-bromo-2-(2,4-difluorophenyl)pyridine (0.5 g, 1.851 mmol), 2-(4-chloro-2,6-dimethylphenyl)-4,4,5,5-tetramethyl-1,3,2-dioxaborolane (0.730 g, 2.74 mmol), dicyclohexyl(2',4',6'-triisopropyl-[1,1'-biphenyl]-3-yl)phosphine (0.021 g, 0.044 mmol), diacetoxypalladium (8.31 mg, 0.037 mmol), and butanol (Volume: 6 ml) to give a yellow suspension. The reaction mixture was then stirred for 15 minutes at room temperature. Lithium hydroxide (0.075 g, 3.15 mmol) was added into reaction mixture and then heated to 80° C. for 1 hour. The reaction mixture was then diluted with deionized water and extracted by ethyl acetate. The organic portion was combined and subjected to column chromatography (SiO$_2$ gel, 5% EtOAc in heptane) to yield the desired compound, 5-(4-chloro-2,6-dimethylphenyl)-2-(2,4-difluorophenyl)pyridine (0.525 g, 86%).

Synthesis of 2-(2,4-difluorophenyl)-5-(2,6-dimethyl-4-(4,4,5,5-tetramethyl-1,3,2-dioxaborolan-2-yl)phenyl)pyridine

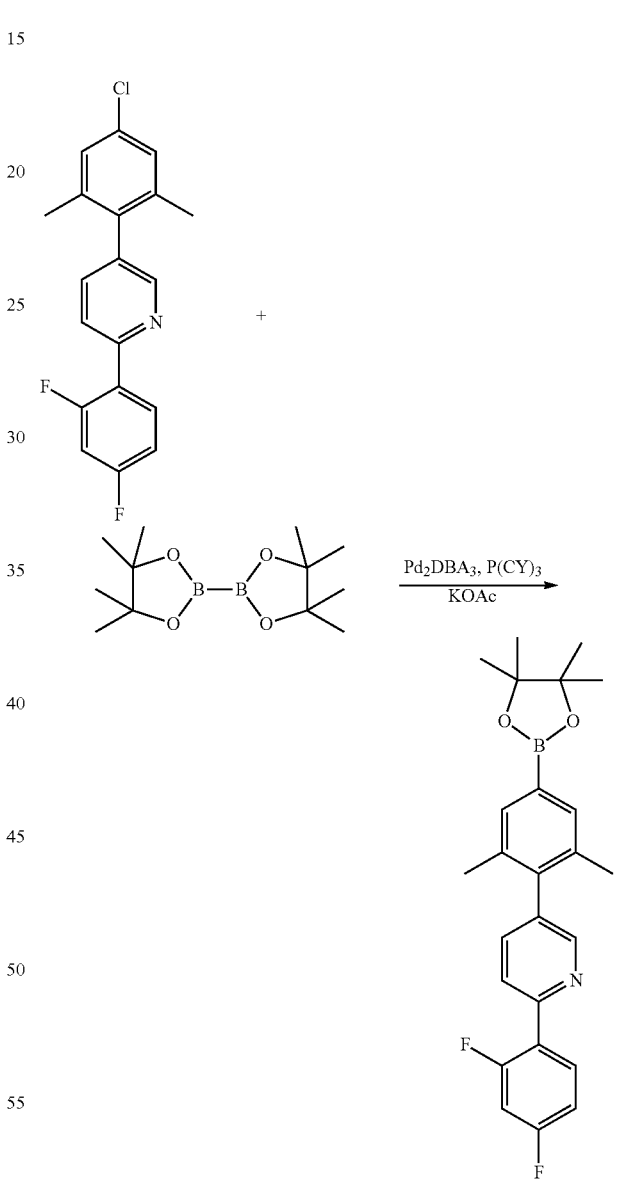

One 250 mL round-bottomed flask was charged with Pd2DBA3 (0.083 mmole, 0.076 g), 5-(4-chloro-2,6-dimethylphenyl)-2-(2,4-difluorophenyl)pyridine (1.362 g, 4.13 mmol), 4,4,4',4',5,5,5',5'-octamethyl-2,2'-bi(1,3,2-dioxaborolane) (1.363 g, 5.37 mmol), potassium acetate (1.257 g, 12.80 mmol), tricyclohexylphosphine (0.093 g, 0.330 mmol), and Dioxane (20 ml) to give a yellow solution. The reaction mixture was refluxed for 12 hours. Then the reaction mixture was diluted with deionized water and extracted by ethyl acetate. The organic portion was combined and subjected to column chromatography (SiO₂ gel, 20% EtOAc in heptane) to yield the desired compound, 2-(2,4-difluorophenyl)-5-(2,6-dimethyl-4-(4,4,5,5-tetramethyl-1,3,2-dioxaborolan-2-yl)phenyl)pyridine (1.5 g, 86%).

Synthesis of the Ligand for Compound B1

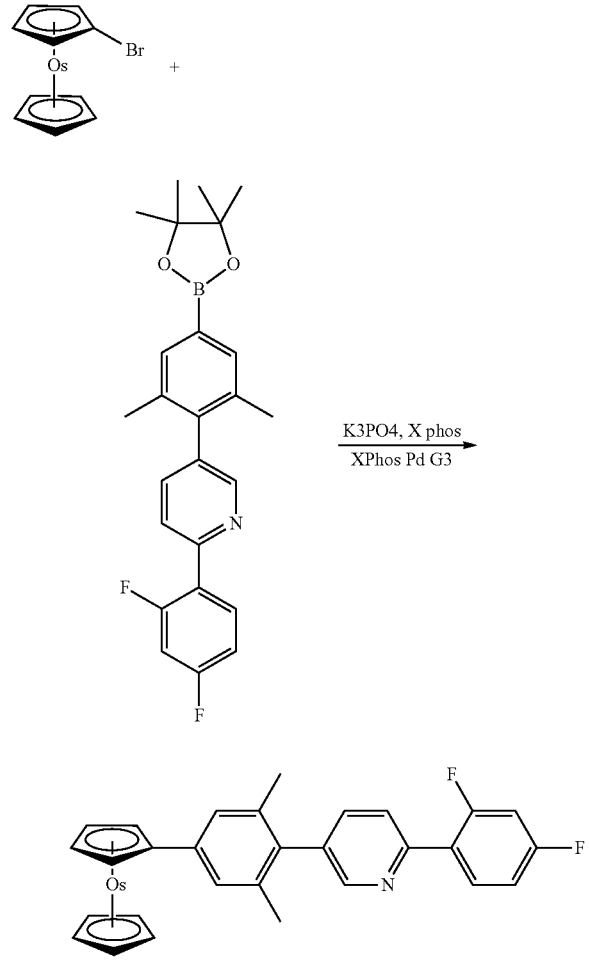

One 100 ml round-bottomed flask was charged with bromoosmocence (3.17 g, 7.94 mmole); 2-(2,4-difluorophenyl)-5-(2,6-dimethyl-4-(4,4,5,5-tetramethyl-1,3,2-dioxaborolan-2-yl)phenyl)pyridine (3.68 g, 8.73 mmol), Xphos Pd G3 (a.k.a. (2-Dicyclohexylphosphino-2',4',6'-triisopropyl-1,1'-biphenyl)[2-(2'-amino-1,1'-biphenyl)]palladium(II) methanesulfonate, XPhos-G3-Palladacycle) (0.53 g, 0.63 mmole), dicyclohexyl(2',4',6'-triisopropyl-[1,1'-biphenyl]-2-yl)phosphine (0.303 g, 0.635 mmol), dioxane (25 ml) and 0.5M of K₃PO₄ aqueous solution (25 ml) to give a yellow suspension. The reaction mixture was heated to 40° C. for 8 hours. The reaction mixture was then diluted with deionized water and extracted by EtOAc. The organic portion was combined and subjected to column chromatography (5% EtOAc in heptane) to yield the desired ligand (1.17 g, 24%).

Synthesis of Iridium dichloro bridge dimer:

Synthesis of Dichloro Bridge Dimer

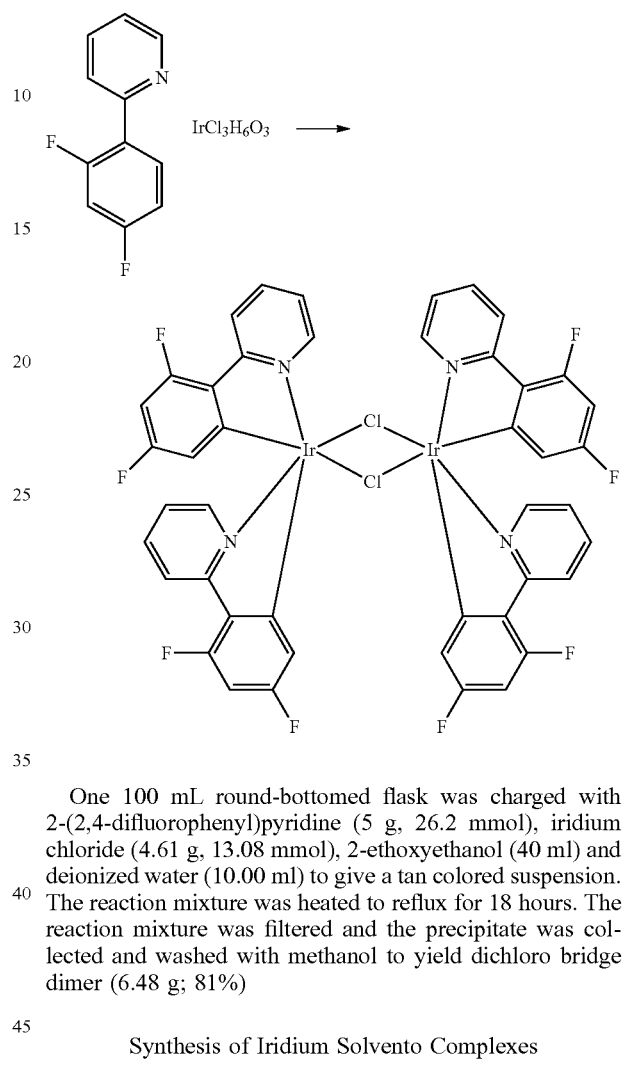

One 100 mL round-bottomed flask was charged with 2-(2,4-difluorophenyl)pyridine (5 g, 26.2 mmol), iridium chloride (4.61 g, 13.08 mmol), 2-ethoxyethanol (40 ml) and deionized water (10.00 ml) to give a tan colored suspension. The reaction mixture was heated to reflux for 18 hours. The reaction mixture was filtered and the precipitate was collected and washed with methanol to yield dichloro bridge dimer (6.48 g; 81%)

Synthesis of Iridium Solvento Complexes

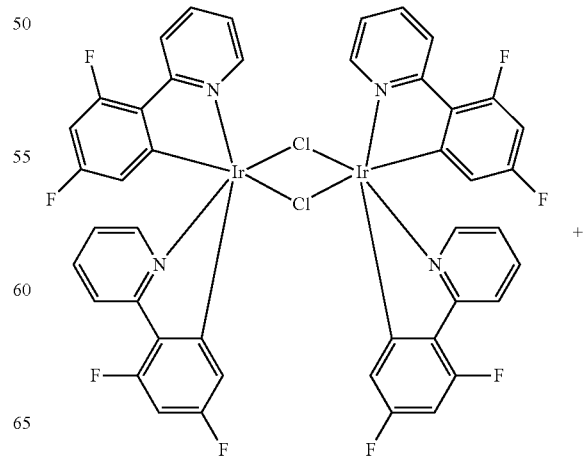

-continued

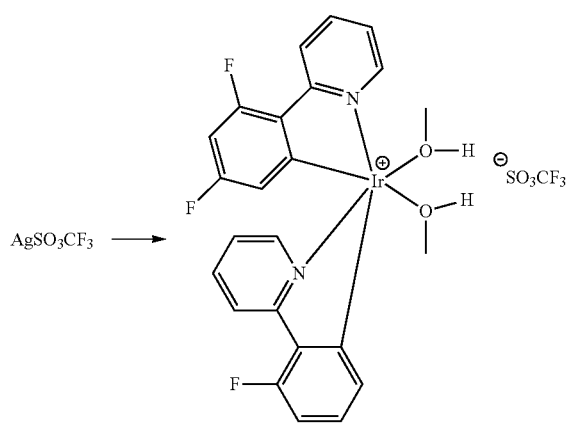

AgSO₃CF₃ ⟶

One 1000 ml round-bottomed flask was charged with the dichloro bridge dimer (6.45 g, 5.31 mmole), silver trifluoromethanesulfonate (2.73 g, 10.62 mmole), dichloromethane (200 ml) and MeOH (200 ml) to give a yellow suspension. The reaction mixture was then stirred at room temperature until the reaction mixture reached room temperature. The reaction mixture was filtered and the filtrate was concentrated to dryness to yield iridium solvento complexes (8.35 g, 100%).

Synthesis of Compound 1

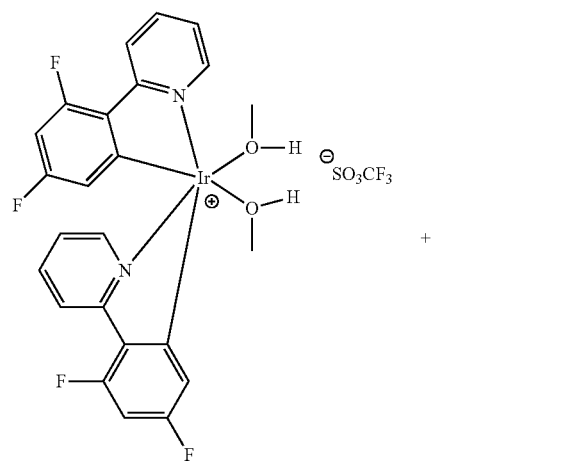

+

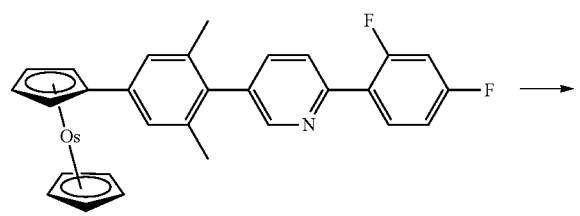

⟶

-continued

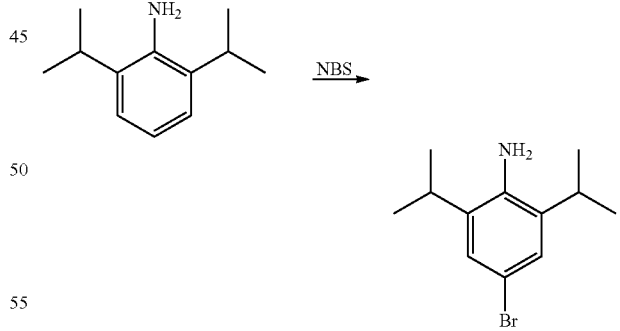

One 100 ml round-bottomed flask was charged with iridium solvento complexes (2.247 g, 2.86 mmole), ligand (1.17 g, 1.906 mmole), 2-ethoxyethanol (50 ml), and DMF (50.0 ml) to give a yellow suspension. The reaction mixture was then heated to 150° C. for 24 hours. The solvent was evaporated to dryness and the residue was subjected to a column chromatography (SiO₂, 40% DCM in heptane) to yield the mer isomer (1.78 g). The Mer isomer (1.78 g) was dissolved in DMSO (450 ml) and acetonitrile (1000 ml) and then subjected to photolysis for 16 hours. After photolysis is completed, the solvent was evaporated to dryness. The residue was subjected to a column chromatography (SiO₂ gel, 40% DCM in heptane) to yield Compound 1. (0.934 g, 41%).

Synthesis of Compound 36

Detailed Synthesis

Synthesis of 4-bromo-2,6-diisopropylaniline

A three neck round bottom flask was charged with 2,6-diisopropylaniline (22.96 g, 130 mmol) and DMF (Volume: 250 ml). A solution of 1-bromopyrrolidine-2,5-dione (23.05 g, 130 mmol) in 100 ml DMF was added into reaction mixture drop wise at 0° C. After addition was over; reaction mixture was stirred for 2 days at room temperature. The reaction mixture was poured into 500 ml deionized water and extracted with 3×150 ml ether. The combined extracts were washed with 150 ml deionized water, 150 ml 10% lithium chloride, dried over MgSO₄ and evaporated to dryness. The residue was purified by vacuum distillation to yield 4-bromo-2,6-diisopropylaniline (32.3 g; 97%).

Synthesis of N-(4-bromo-2,6-diisopropylphenyl)-3-methoxybenzimidamide

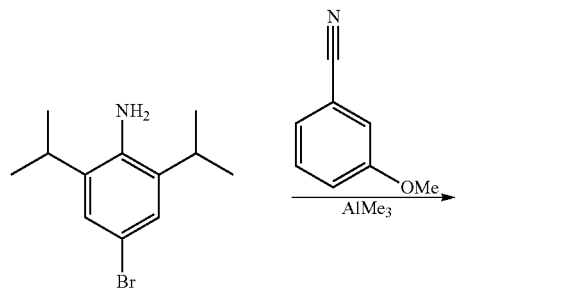

One 2 L 3-neck flask was charged with 4-bromo-2,6-diisopropylaniline (19 g, 74.2 mmol) and toluene (200 ml). Trimethylaluminum (2M solution in toluene, 25 ml) was added dropwise into the reaction mixture at 0° C. After the addition was over, the ice bath was removed and reaction mixture was allowed to stir at room temperature (20-25° C.) for 3 hours. 3-methoxybenzonitrile (9.88 g, 74.2 mmol) in toluene (300 ml) was then added into reaction mixture. The reaction mixture was allowed to heated to 80° C. for 17 hours. The reaction mixture was poured slowly into a slurry of 200 gm of celite in 900 ml of a 2:1 mixture of DCM in methanol. The reaction mixture was then filtered and filtrate was evaporated to dryness, the residue was re-suspend with heptane and filtered to yield N-(4-bromo-2,6-diisopropylphenyl)-3-methoxybenzimidamide (19.73 g, 68%).

Synthesis of 1-(4-bromo-2,6-diisopropylphenyl)-2-(3-methoxyphenyl)-1H-imidazole

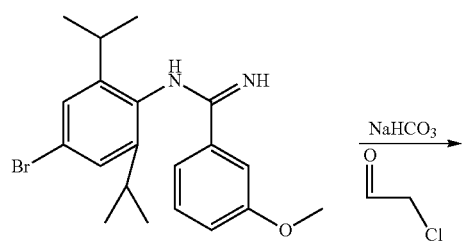

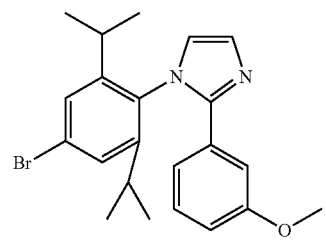

A 500 ml round bottom flask was charged with N-(4-bromo-2,6-diisopropylphenyl)-3-methoxybenzimidamide (19.73 g, 50.7 mmol), 2-chloroacetaldehyde (12.83 ml, 101 mmol), sodium bicarbonate (12.77 g, 152 mmole) and 2-Propanol (300 ml). The reaction was allowed to reflux for 16 hours. The reaction mixture was diluted with deionized water and extracted with ethyl acetate, the organic portion was combined and subjected to a column chromatography (SiO₂ gel; 20% THF in heptane) to yield the desired product (16.47 g, 79%).

Synthesis of 3-(1-(4-bromo-2,6-diisopropylphenyl)-1H-imidazol-2-yl)phenol

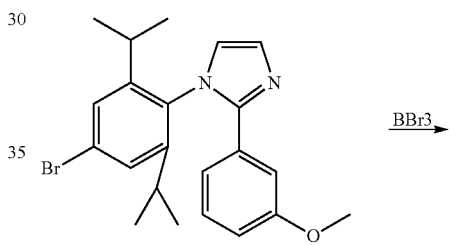

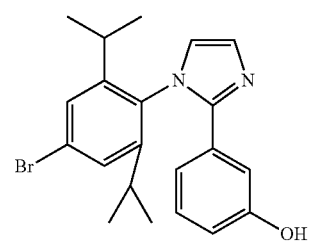

A 250 mL round-bottomed flask was charged with 3-(2,6-diisobutylphenyl)-11-methoxyimidazo[1,2-f]phenanthridine (2.01 g, 4.60 mmol) and CH₂Cl₂ (Volume: 100 ml), tribromoborane (tribromoborane (120 ml of 1M solutiontribromoborane (120 ml, 120 mmol) was added dropwise at −78° C. After the addition was over, the dry-ice bath was removed and reaction mixture was stirred until the reaction mixture reached room temperature (20-25° C.). Reaction mixture was diluted with cold deionized water and neutralized by ammonium hydroxide, extracted by dichloromethane. The organic portion was combined and subjected to a column chromatography (SiO₂ gel, 2% to 5% MeOH in dichloromethane) to yield the desired product, 3-(1-(4-bromo-2,6-diisopropylphenyl)-1H-imidazol-2-yl)phenol (15 g, 94%).

Synthesis of 4'-Bromo-2-nitro-1,1'-biphenyl

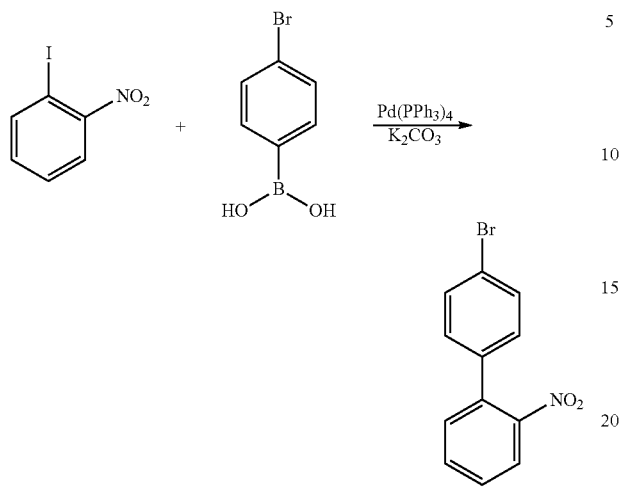

1-Iodo-2-nitrobenzene (28.2 g, 113 mmol), (4-bromophenyl)boronic acid (25 g, 124 mmol), Pd(Ph₃P)₄ (1.3 g, 1.1 mmol), potassium carbonate (46.9 g, 340 mmol), DME (300 mL) and water (200 mL) were added to a flask and degassed with nitrogen for 20 minutes. The reaction mixture was heated to reflux for 16 hours. The reaction mixture was then cooled to room temperature (20-25° C.) and 200 mL of EtOAc and 200 mL of deionized water were added into reaction mixture. After separating the layers, the aqueous layer was washed twice with EtOAc and the combined organics was washed twice with deionized water. The combined organic portion was dried over sodium sulfate, filtered and evaporated to dryness to give 34.3 g of an amber oil. The oil was then subjected to a column chromatography (SiO₂ gel, 9/1 hexane/EtOAc) to yield 23.7 g (75%) of 4'-bromo-2-nitro-1,1'-biphenyl. The product was confirmed by GC/MS and NMR.

Synthesis of 2-Bromo-9H-carbazole

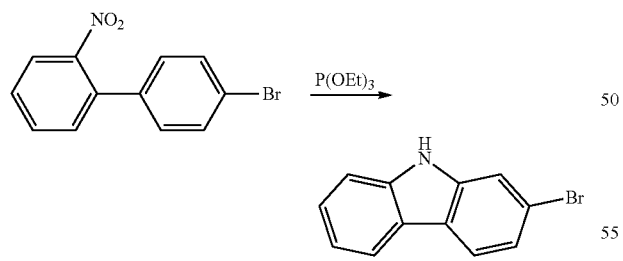

A round bottom flask was charged with 4'-bromo-2-nitro-1,1'-biphenyl (14.5 g, 52.1 mmol), triethyl phosphite (50 g, 301 mmol) and heated to reflux under nitrogen overnight. The reaction mixture was allowed to cool to room temperature (20-25° C.) and 60 mL of 6 N HCl was added dropwise. The reaction mixture was then heated to 80° C. for 3 hours. The reaction mixture was then cooled to 5° C. and neutralized with 50% NaOH, diluted with deionized water and extracted with 3×150 mL EtOAc. The combined extracts were washed with 150 mL deionized water and 150 mL brine, dried over MgSO₄ and evaporated to dryness. The lower boiling impurities were removed by Kugelrohr distillation and the residue was subjected to a column chromatography (SiO₂ gel, 9/1 hexane/EtOAc) to yield 8.4 g (65%) of 2-Bromo-9H-carbazole as an off-white solid. The product was confirmed by GC/MS and NMR.

Synthesis of 2-Bromo-9-(pyridin-2-yl)-9H-carbazole

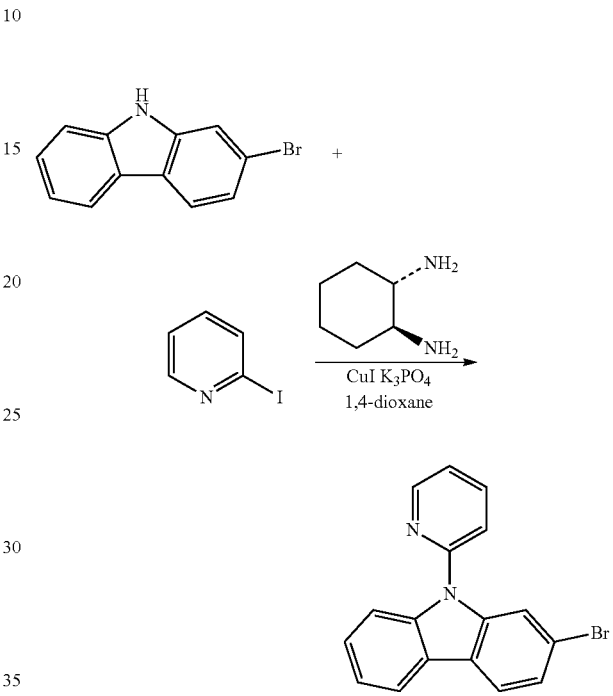

A 100 mL 3-neck flask was charged with copper iodide (0.057 g, 0.301 mmol), 2-bromo-9H-carbazole (7.4 g, 30.1 mmol), 2-iodopyridine (12.3 g, 60.1 mmol), potassium phosphate (12.8 g, 60.1 mmol), (1R,4R)-cyclohexane-1,4-diamine (0.343 g, 3.0 mmol), and dioxane (25 mL) and the reaction mixture was heated at 65° C. for 16 hours. The reaction mixture was then poured into deionized water and extracted with dichloromethane The organic layers were combined and subjected to a column chromatography (neutral Al₂O₃, 99/1 hexane/EtOAc) to yield 4.2 g (43%) of 2-bromo-9-(pyridin-2-yl)-9H-carbazole as a white solid. The product was confirmed by GC/MS and NMR.

Synthesis of 2-iodo-9-(pyridin-2-yl)-9H-carbazole

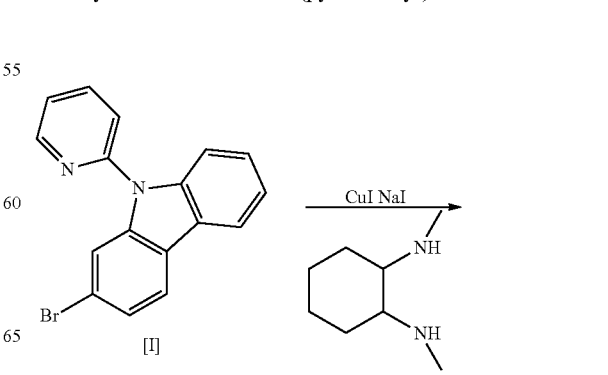

-continued

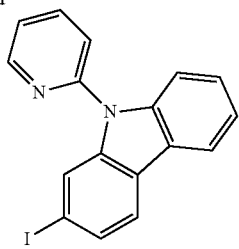

A 100 ml three neck round bottom flask was charged with 2-bromo-9-(pyridin-2-yl)-9H-carbazole (10.15 g, 31.4 mmol), copper(I) iodide (1.196 g, 6.28 mmol), N1,N2-dimethylcyclohexane-1,2-diamine (1.981 ml, 12.56 mmol), sodium iodide (18.83 g, 126 mmol), and Dioxane (60 ml.). The reaction mixture was then heated to reflux for 18 hours. The reaction mixture was diluted with deionized water and extracted with ethyl acetate. The organic portion was combined and subjected to column chromatography (SiO$_2$, 50% DCM in heptane) to yield 2-iodo-9-(pyridin-2-yl)-9H-carbazole (9.66 g, 83%).

Synthesis of 2-(3-(1-(4-bromo-2,6-diisopropylphenyl)-1H-imidazol-2-yl)phenoxy)-9-(pyridin-2-yl)-9H-carbazole

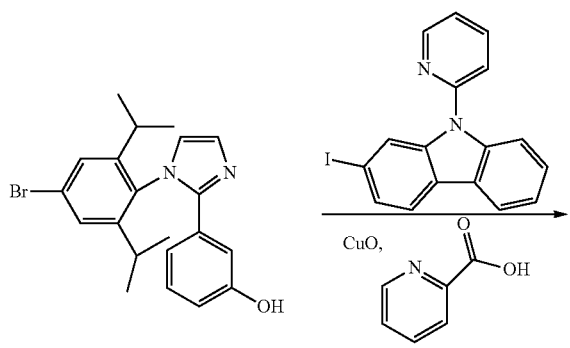

-continued

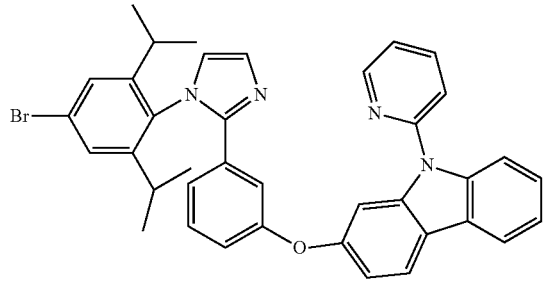

A 500 ml three neck flask was charged with 2-iodo-9-(pyridin-2-yl)-9H-carbazole (6.59 g, 17.80 mmol), copper(I) iodide (0.323 g, 1.695 mmol), picolinic acid (0.417 g, 3.39 mmol), K$_3$PO$_4$ (7.20 g, 33.9 mmol), and DMSO (160 ml). The reaction mixture was heated to 90° C. for 90 hours. The reaction mixture was diluted with 10% LiCl aqueous solution and extracted with ethyl acetate. The organic layer was concentrated and subjected to a column chromatography (SiO$_2$ gel, 30% EtOAc in heptane) to yield the desired product, 2-(3-(1-(4-bromo-2,6-diisopropylphenyl)-1H-imidazol-2-yl)phenoxy)-9-(pyridin-2-yl)-9H-carbazole (7.11 g, 65%).

Synthesis of 2-(3-(1-(2,6-diisopropyl-4-(4,4,5,5-tetramethyl-1,3,2-dioxaborolan-2-yl)phenyl)-1H-imidazol-2-yl)phenoxy)-9-(pyridin-2-yl)-9H-carbazole

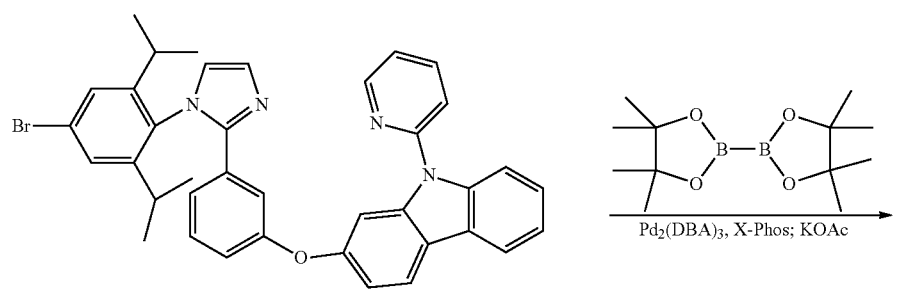

A three neck round bottom flask was charged with 2-(3-(1-(4-bromo-2,6-diisopropylphenyl)-1H-imidazol-2-yl)phenoxy)-9-(pyridin-2-yl)-9H-carbazole (7.11 g, 11.08 mmol), 4,4,4',4',5,5,5',5'-octamethyl-2,2'-bi(1,3,2-dioxaborolane) (8.44 g, 33.2 mmol), Pd$_2$DBA$_3$ (0.203 g, 0.222 mmol), dicyclohexyl(2',4',6'-triisopropyl-[1,1'-biphenyl]-2-yl)phosphine (0.423 g, 0.887 mmol), potassium acetate(3.26 g, 33.2 mmol), and Dioxane (150 ml). The reaction mixture was allowed to reflux for 16 hours. The reaction mixture was diluted with 10% LiCl aqueous solution and extracted by Ethyl acetate. The organic portion was combined and subjected to a column chromatography (SiO$_2$ gel, 30% EtOAc in heptane;) to yield (1)(6.90 g) (90%) of 2-(3-(1-(2,6-diisopropyl-4-(4,4,5,5-tetramethyl-1,3,2-dioxaborolan-2-yl)phenyl)-1H-imidazol-2-yl)phenoxy)-9-(pyridin-2-yl)-9H-carbazole.

Synthesis of Compound 36

Synthesis of Ligand for Compound C1

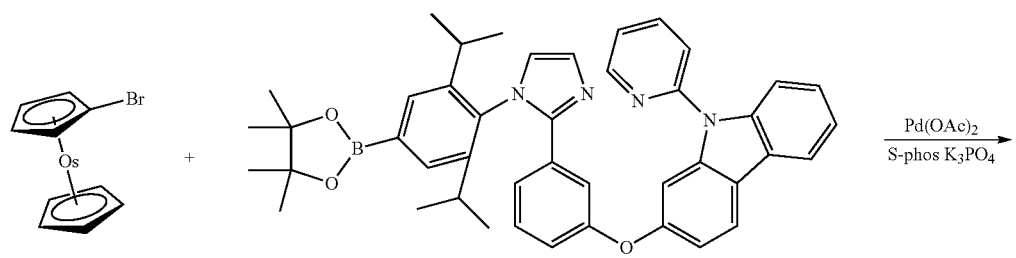

A 5 ml round bottom flask was charged with Bromoosmocence (50 mg, 0.125 mmole), 2-(3-(1-(2,6-diisopropyl-4-(4,4,5,5-tetramethyl-1,3,2-dioxaborolan-2-yl)phenyl)-1H-imidazol-2-yl)phenoxy)-9-(pyridin-2-yl)-9H-carbazole (95 mg, 0.138 mmol), diacetoxypalladium (1.124 mg, 5.01 μmol), dicyclohexyl(2',6'-dimethoxy-[1,1'-biphenyl]-3-yl), phosphine (4.11 mg, 10.02 μmol), K$_3$PO$_4$ (53.2 mg; 0.25 mmole), and DMF (1.5 ml). The reaction mixture was heated to 120° C. for 16 hours. The reaction mixture was diluted with deionized water and extracted by ethyl acetate. The organic portion was combined and subjected to a column chromatography (SiO$_2$ gel; 30% EtOAc in heptane) to yield the Ligand for Compound C1 (78 mg, 70%).

Synthesis of Compound 36

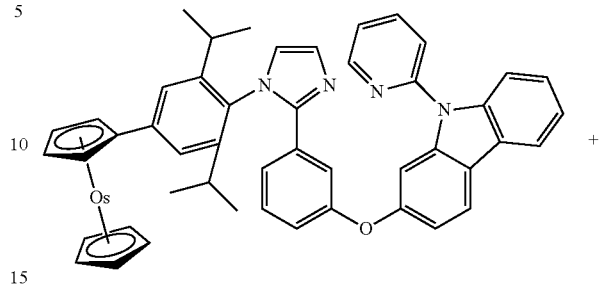

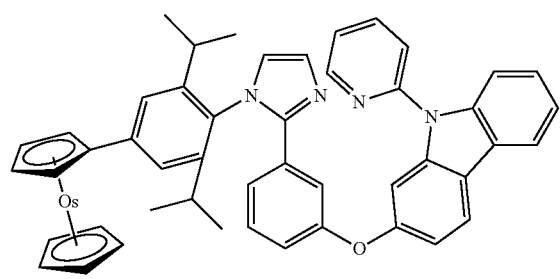

-continued

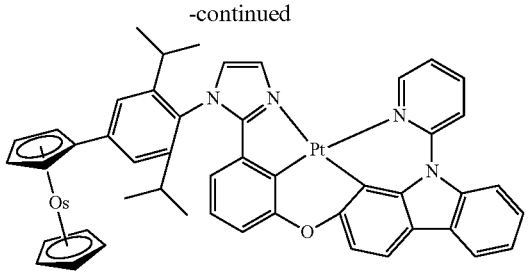

One 10 ml tube was charged with the Ligand for Compound 36 (0.385 g, 0.437 mmol); K$_2$PtCl$_4$ (0.181 g, 0.437 mmol); acetic acid (1.98 ml) and deionized water (0.2 ml). The reaction mixture was subjected to microwave with temperature setting of 160° C. (200 W) for 1 hour and 19 minutes. The suspension was filtered to yield crude product. The crude product was further purified by a column chromatography (SiO₂ gel, 40% dichloromethane in heptane) to yield Compound 36 (0.4 g, 85%).

Table 2 below lists the HOMO/LUMO levels of another novel phosphorescent dopant Compound 36 according to the present disclosure and a comparative compound Compound C that were evaluated by Cyclic Voltammetry. Compound C and 36 have the same triplet energy but Compound 36 has a shallower HOMO than Compound C because of the pendant osmocene group on Compound 36. As a result, Compound 36 has a smaller electrochemical gap than Compound C.

TABLE 2

Comparison of HOMO/LUMO levels evaluated via Cyclic Voltammetry data

| | Oxidation potential | Reduction Potential | Gap (eV) | T1 |
|---|---|---|---|---|
| 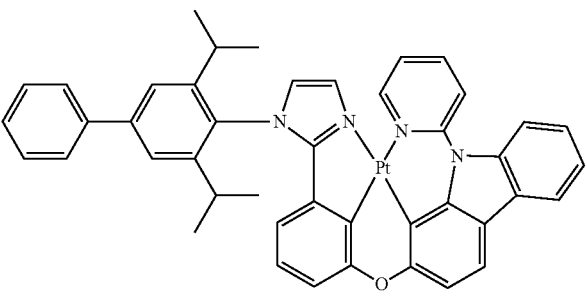 Compound C | 0.46 V | −2.56 V | 3.02 | 470 nm |
| 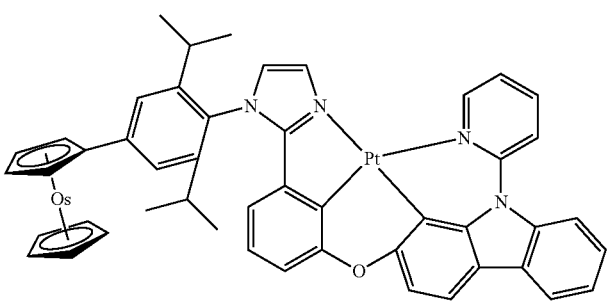 Compound 36 | 0.35 V | −2.45 V | 2.80 | 470 nm |

Condition for electrochemistry: Anhydrous DMF was used as the solvent under an inert atmosphere, and 0.1M tetra(n-butyl)ammonium hexafluorophosphate was used as the supporting electrolyte. A glassy carbon rod was used as the working electrode, a platinum wire was used as the counter electrode, and a silver wire was used as a pseudo-reference electrode. The redox potentials are based on values measured from differential pulsed voltammetry and are reported relative to a ferrocence/ferrocenium (Cp₂Fe/Cp₂Fe⁺) redox couple that was used as an internal reference.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound comprising a first ligand $L^1$ having the Formula:

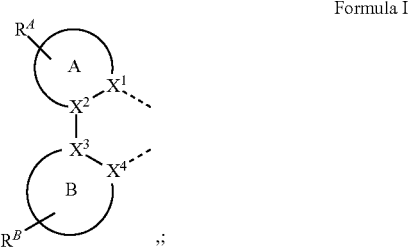

Formula I wherein
(1) ring A is pyridine and ring B is a phenyl, $X^1$ is N, and $X^2$, $X^3$ and $X^4$ are C; or
(2) ring A is an imidazole or its derived carbene, and ring B is a phenyl, wherein $X^1$ and $X^2$ are independently N or C, and $X^3$ and $X^4$ are C;
wherein $R^A$ and $R^B$ each independently represent mono, di, tri, or tetra substitution, or no substitution;

wherein at least one of $R^A$ and $R^B$ is present and has a structure according to the following formula:

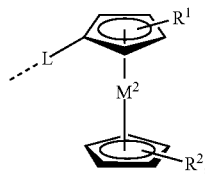

Formula II wherein L is a direct bond or a linker selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein $R^1$ represents mono, di, tri, or tetra substitution, or no substitution;

wherein $R^2$ represents mono, di, tri, tetra, or penta substitution, or no substitution;

wherein $M^2$ is selected from the group consisting of Os, Ru, and Re;

wherein $R^1$ and $R^2$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein when $R^A$ and $R^B$ is not Formula II, $R^A$ and $R^B$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any two adjacent substituents are optionally joined to form a ring, which can be further substituted;

wherein the ligand $L^1$ is coordinated to Pt or Ir;

wherein Pt and Ir can be coordinated to other ligands; and wherein the ligand $L^1$ is optionally linked with other ligands to comprise a tridentate, tetradentate, pentadentate or hexadentate ligand.

2. The compound of claim 1, wherein at least one of $R^A$ and $R^B$ has a structure according to the following formula:

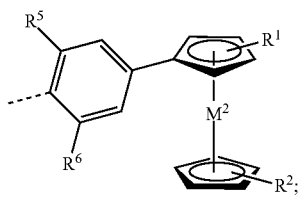

Formula III and wherein $R^5$ and $R^6$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

3. The compound of claim 1, wherein when (1) is true the ligand $L^1$ is

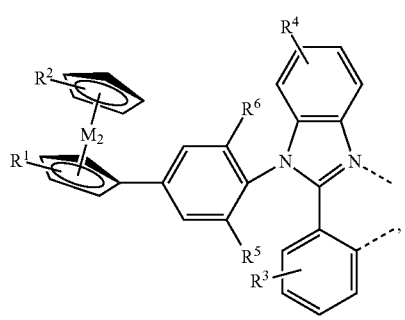

and when (2) is true the ligand $L^1$ is selected from the group consisting of:

-continued

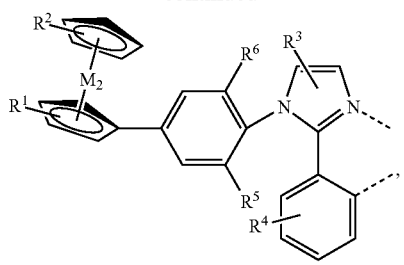

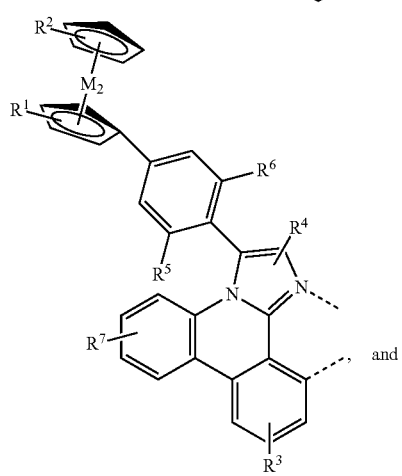

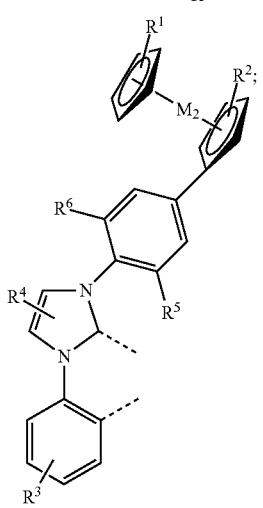

and wherein R³ and R⁴ each independently represent mono, di, tri, or tetra substitution, or no substitution;

wherein R⁷ represents mono, di or tri substitution, or no substitution; and wherein R³, R⁴, R⁵, R⁶, and R⁷ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

4. The compound of claim 1, wherein the compound is homoleptic.

5. The compound of claim 1, wherein the compound is heteroleptic.

6. The compound of claim 1, wherein the compound is neutral.

7. The compound of claim 1, wherein when (1) is true the ligand L¹ is selected from the group consisting of:

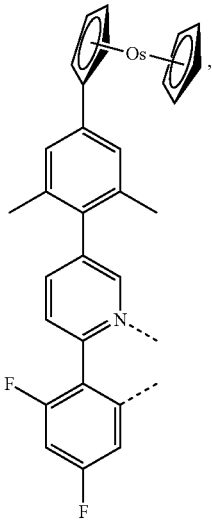

L¹-1

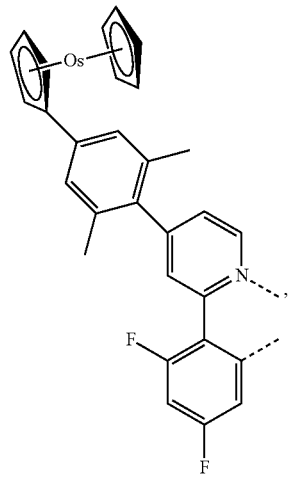

L¹-2

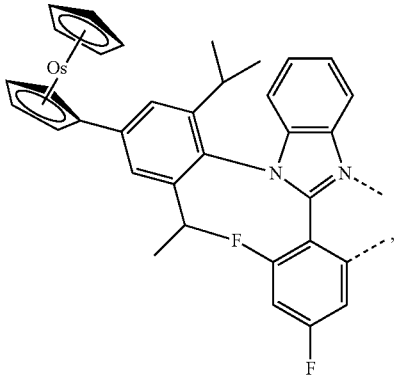

L¹-3

-continued
L¹-6
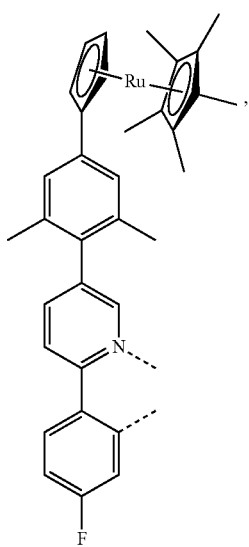
L¹-7
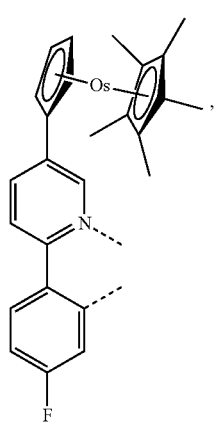
L¹-8
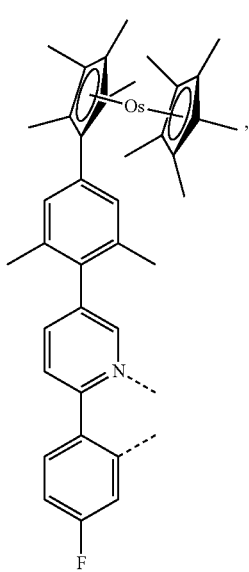
-continued
L¹-9
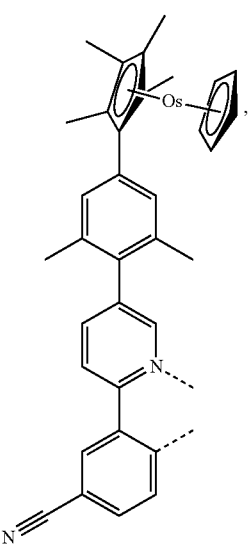
L¹-10
L¹-11
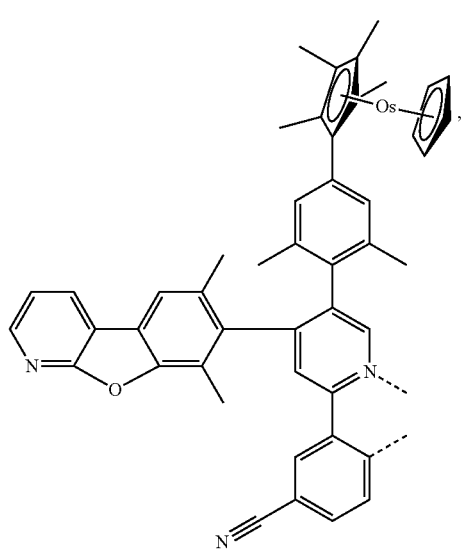

L¹-12 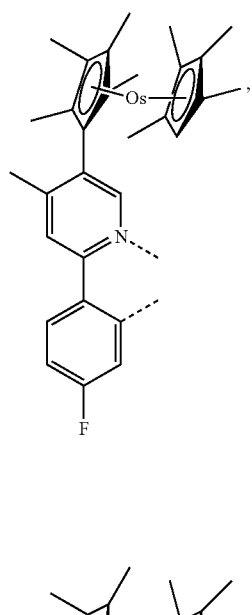
L¹-13 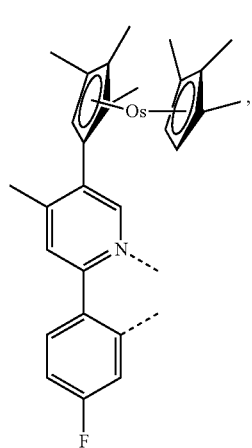
L¹-17 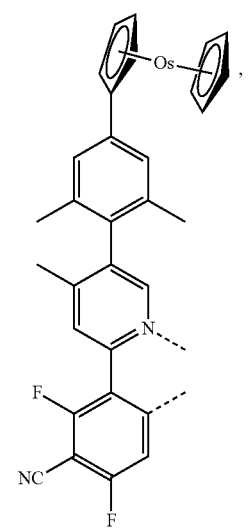
L¹-18 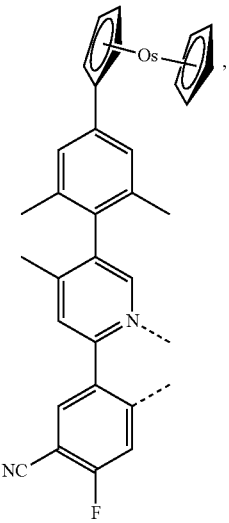
L¹-19 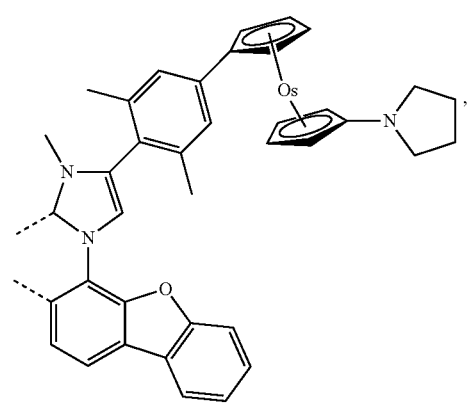
L¹-20 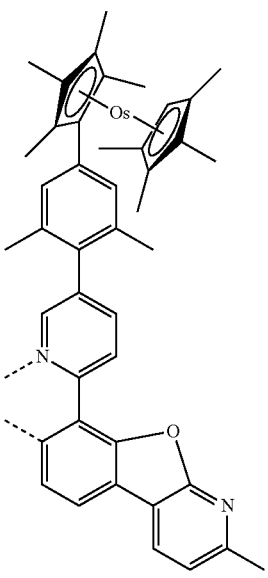

-continued
L¹-21
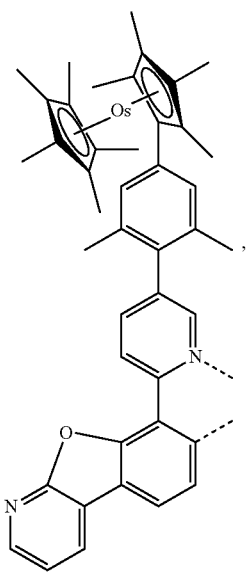
L¹-22
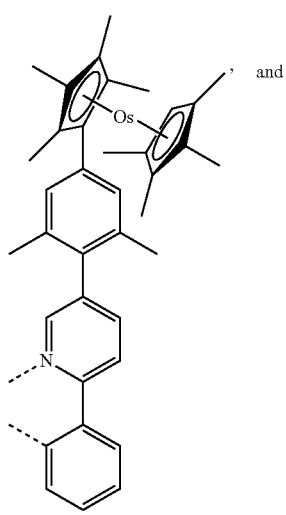, and
L¹-33
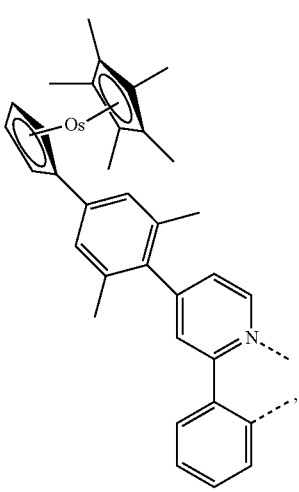
-continued
L¹-34
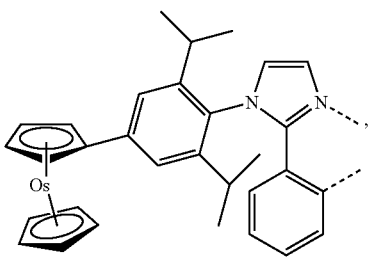
and
when (2) is true the ligand L¹ is selected from the group consisting of:
L¹-3
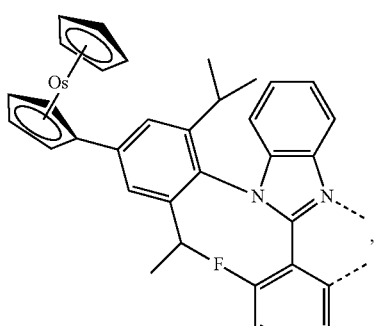
L¹-4
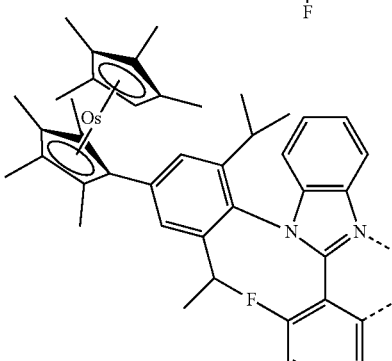
L¹-5
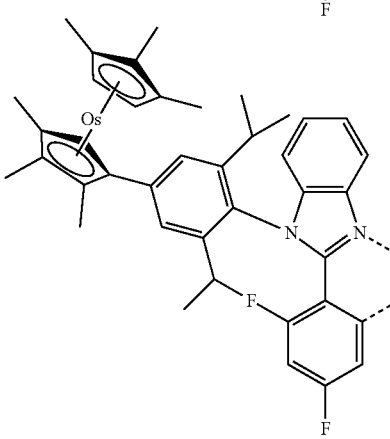

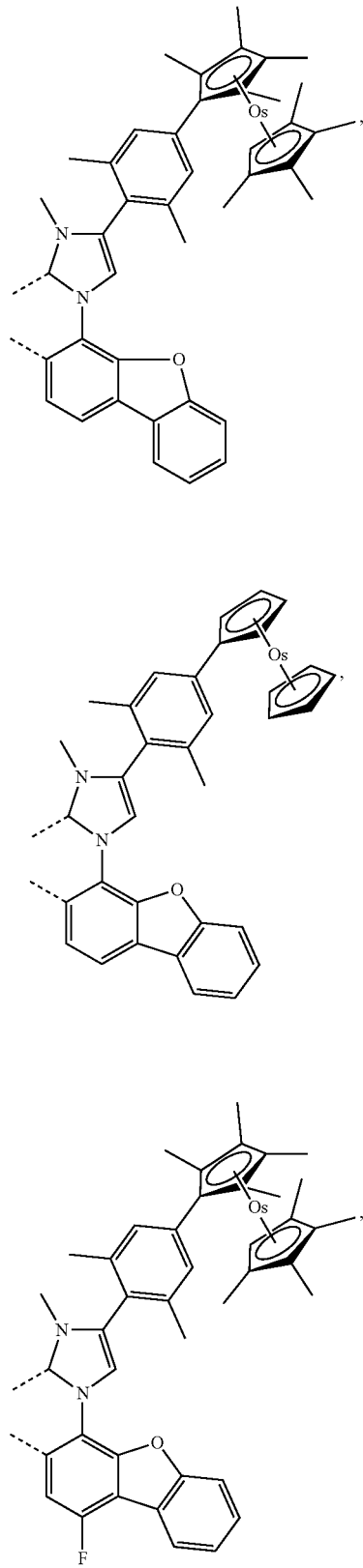
L¹-14
L¹-15
L¹-16
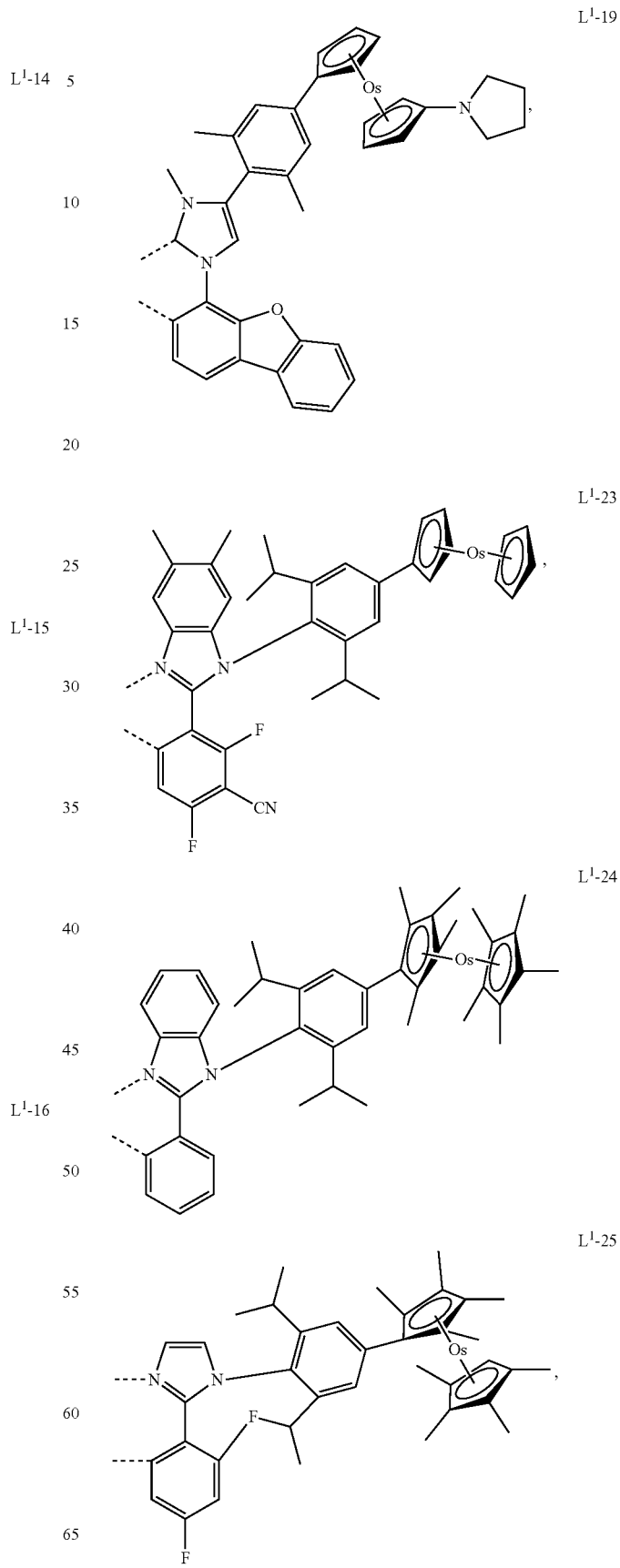
L¹-19
L¹-23
L¹-24
L¹-25

L¹-26
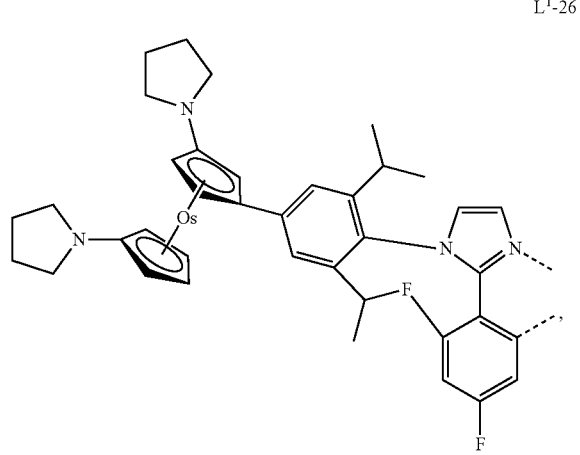
L¹-27
L¹-28
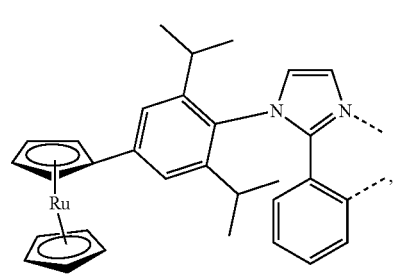
L¹-29
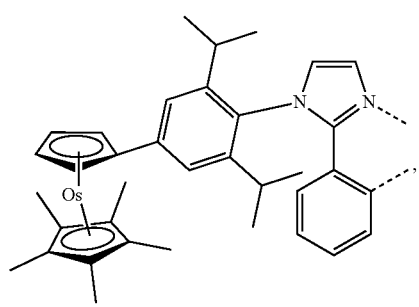
L¹-30
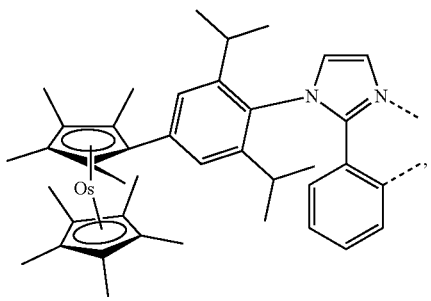
L¹-34
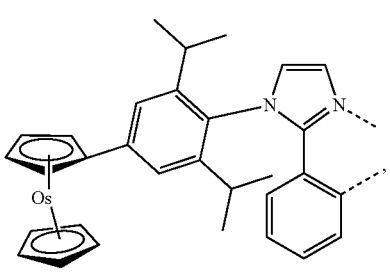
L¹-35
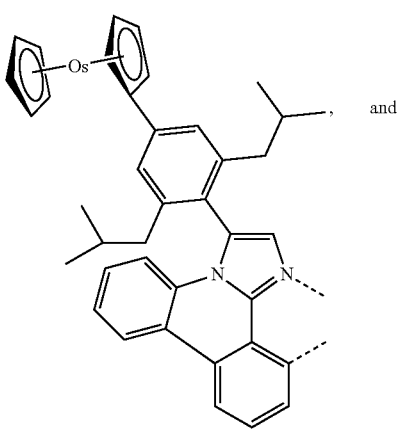
and
L¹-36
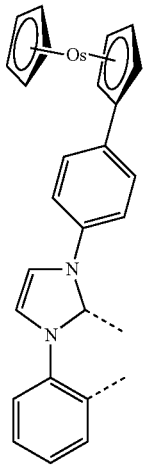
8. The compound of claim 1, wherein the compound has the formula of Pt(L¹)₂ or Pt(L¹)(L²) wherein L² is a second ligand selected from the group consisting of:

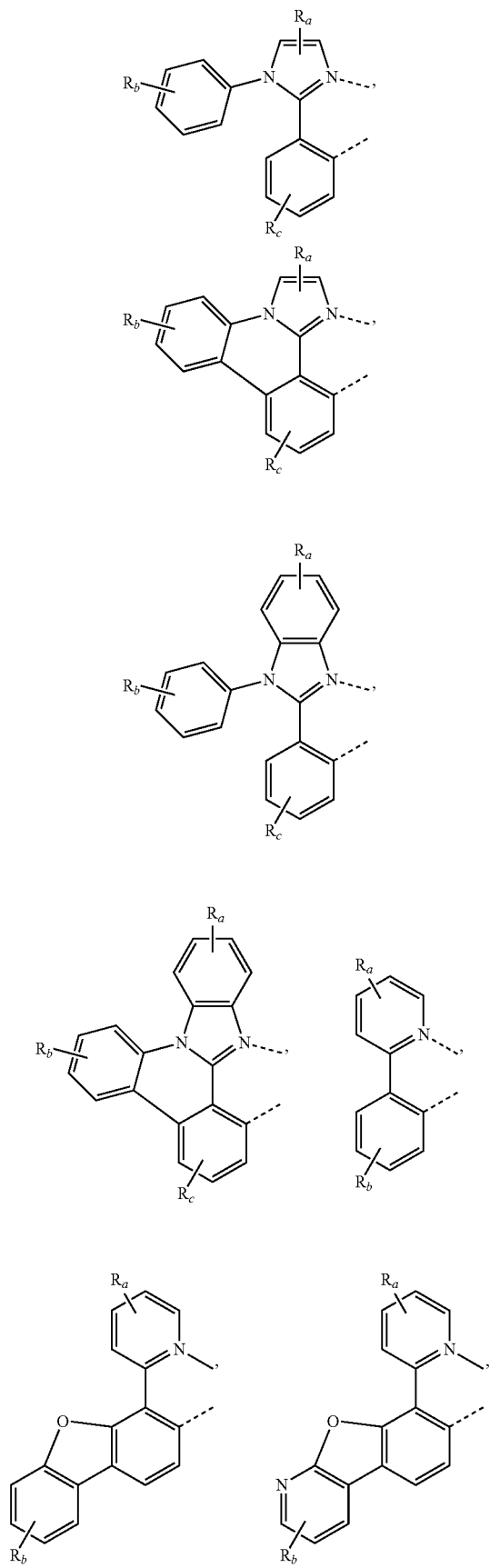
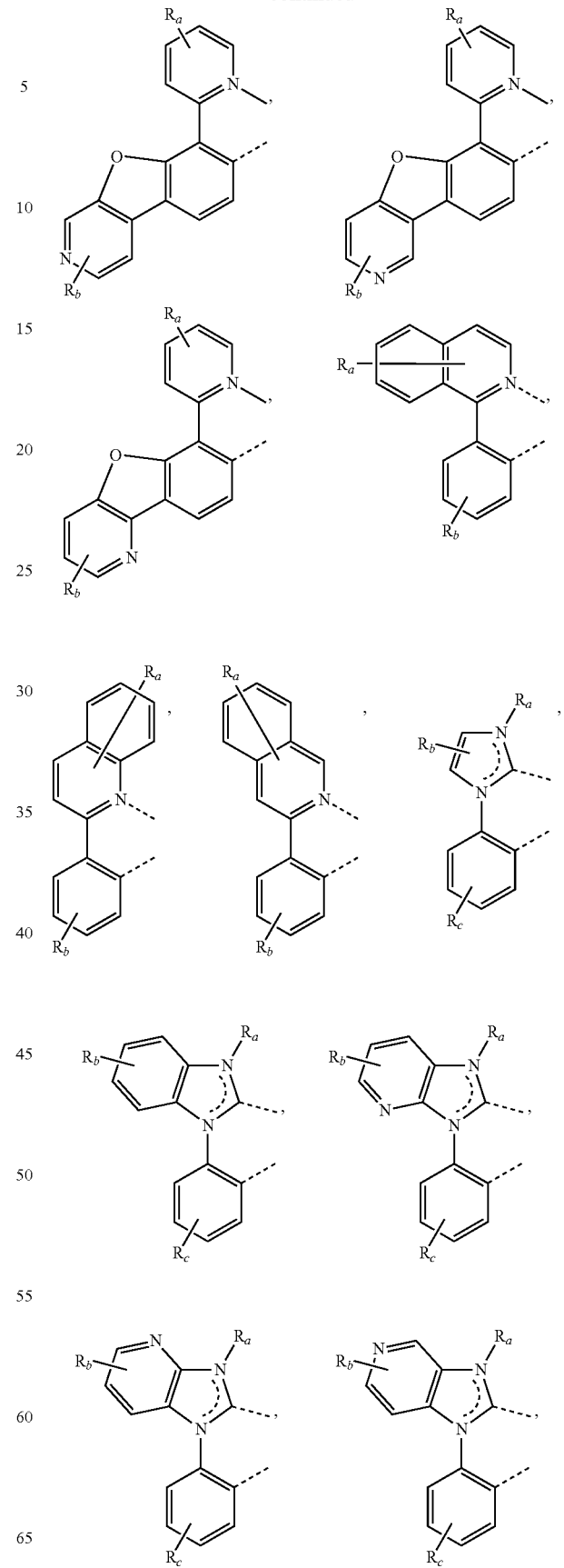

-continued

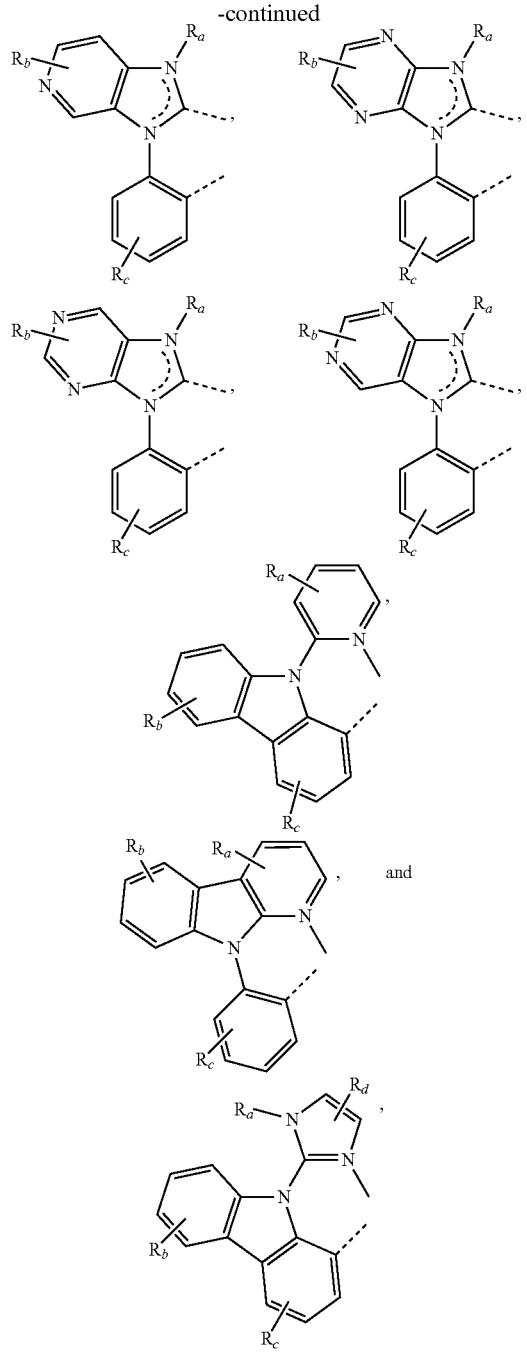

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

9. The compound of claim 8, wherein $L^1$ is connected to $L^2$ to form a tetradentate ligand.

10. The compound of claim 1, wherein when (1) is true the compound is selected from the group consisting of:

Compound 30

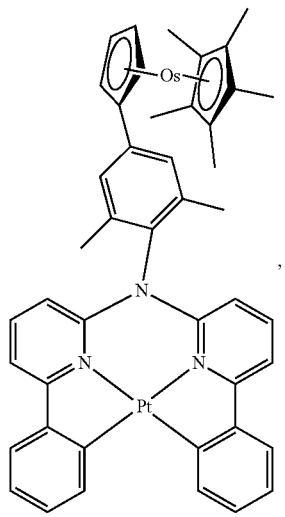

,

Compound 33

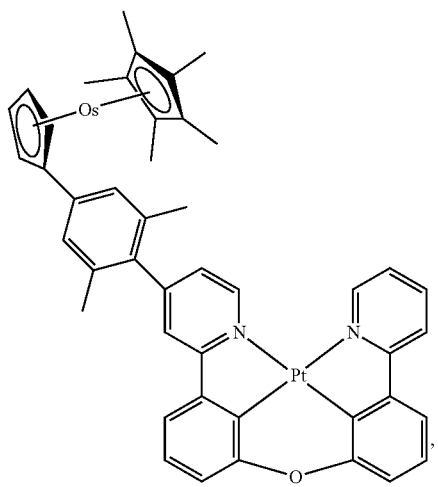

, and

Compound 34

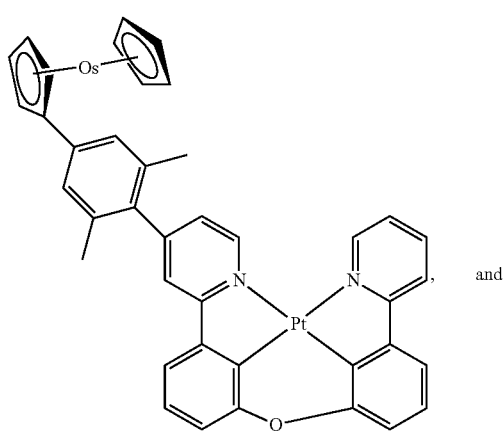

, and

-continued
Compound 1
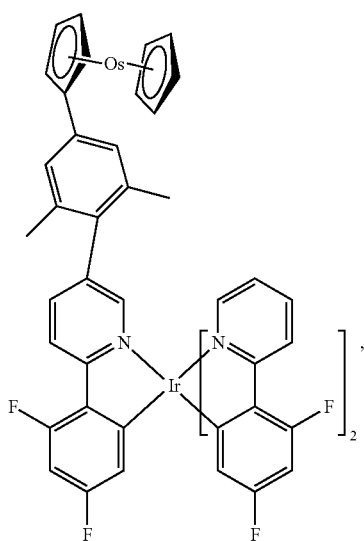
Compound 2
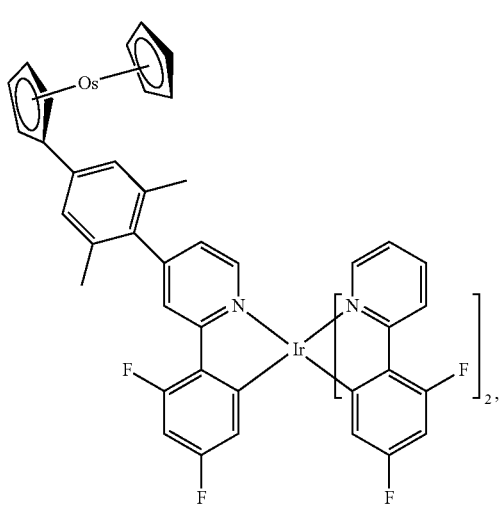
Compound 6
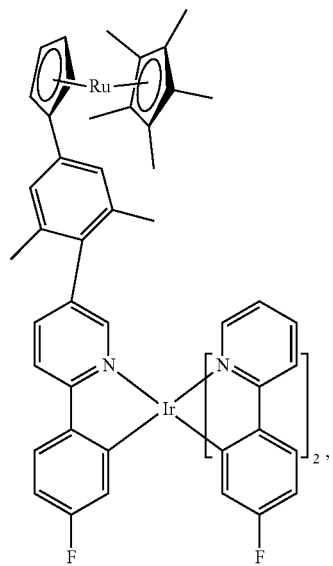
-continued
Compound 7
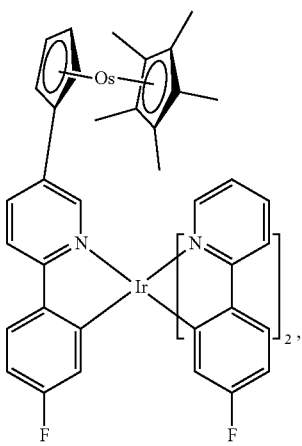
Compound 8
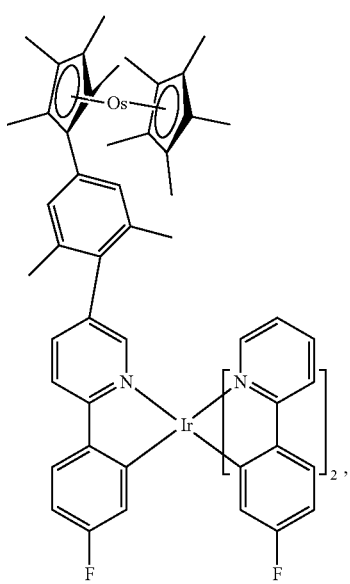
Compound 9
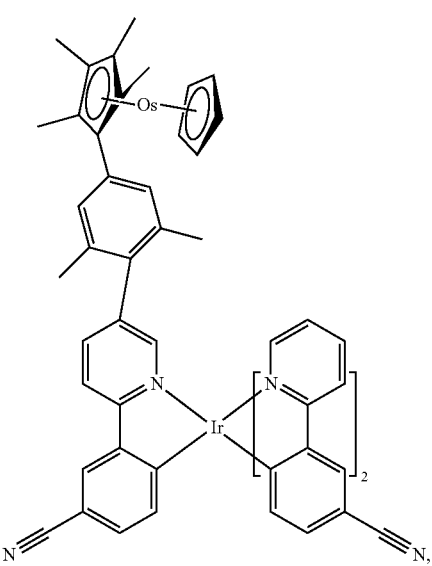

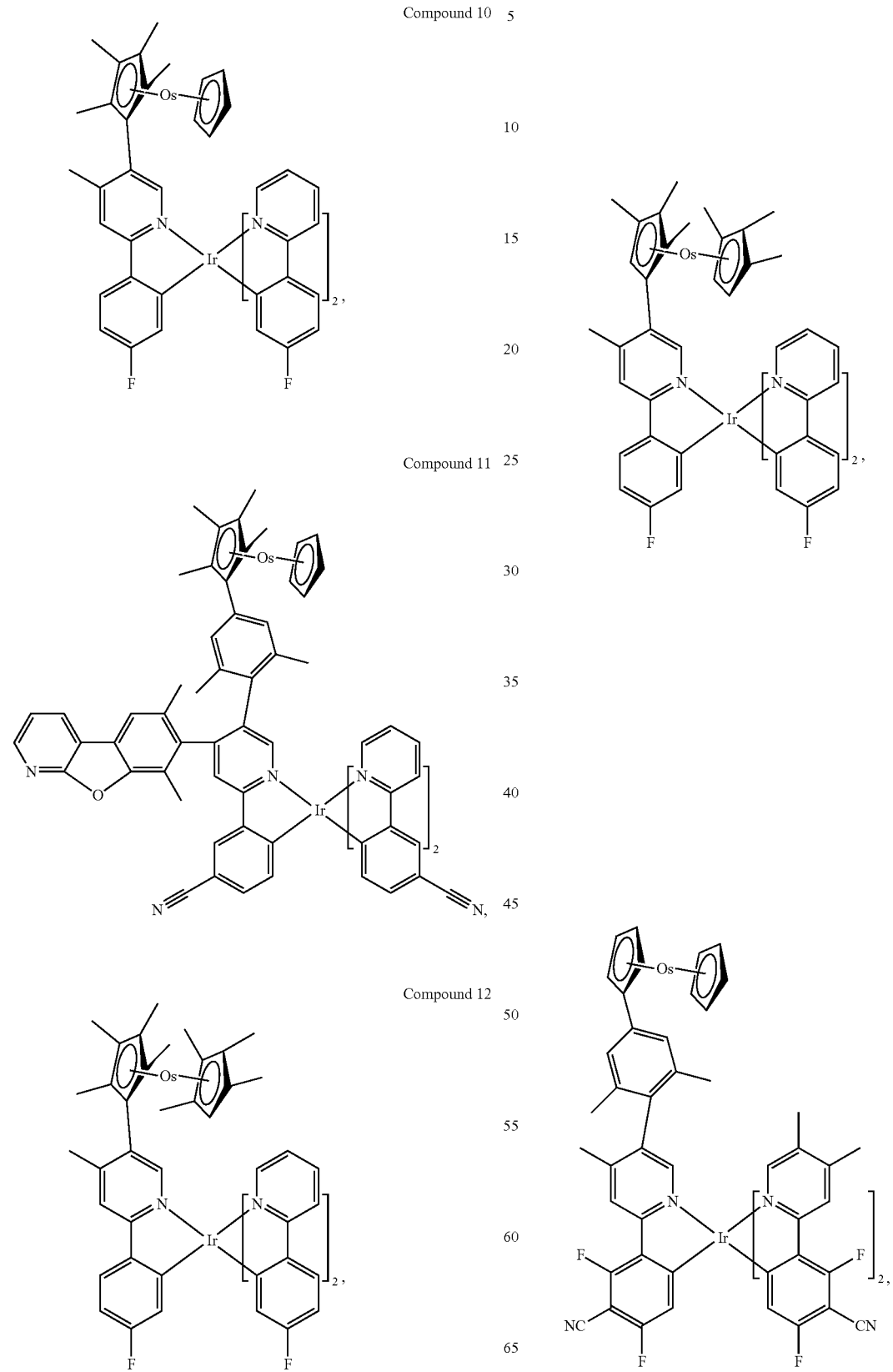

Compound 18
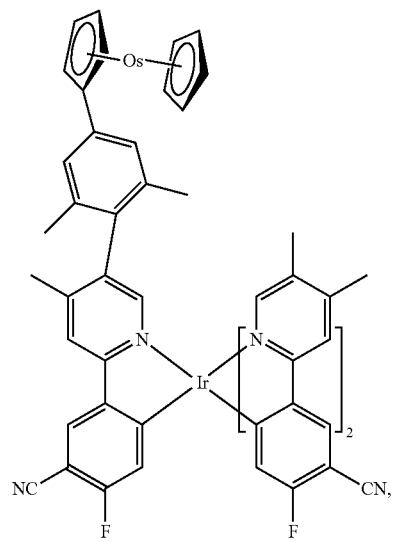
Compound 20
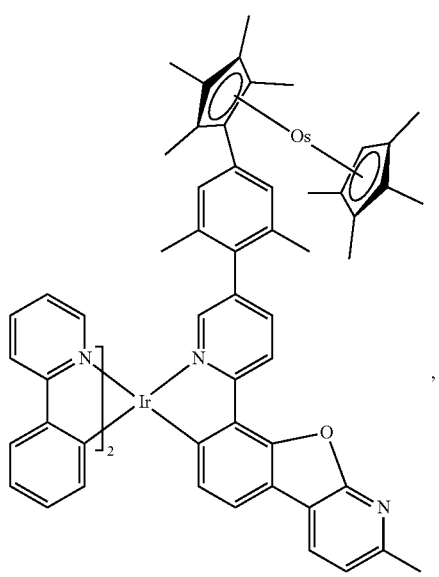
Compound 21
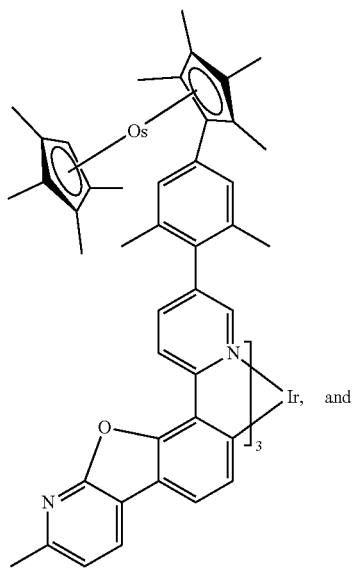
Ir, and
Compound 22
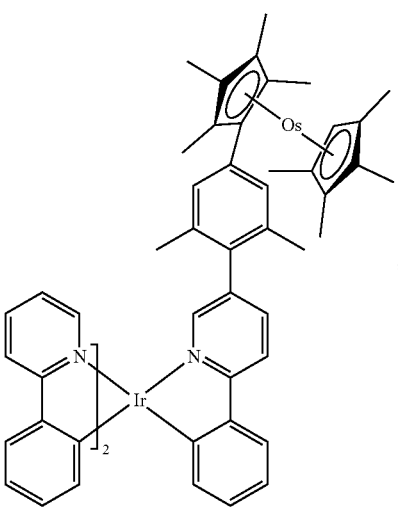
; and
when (2) is true the ligand $L^1$ is selected from the group consisting of:
Compound 3
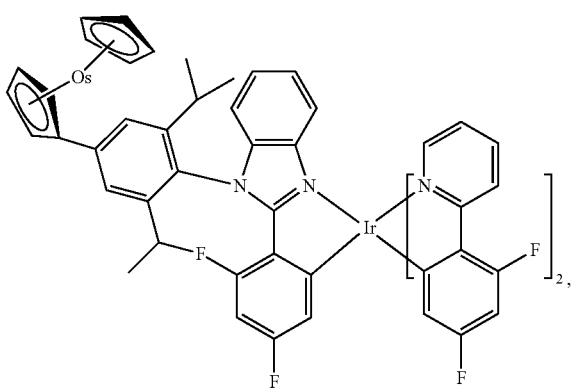

-continued
Compound 14
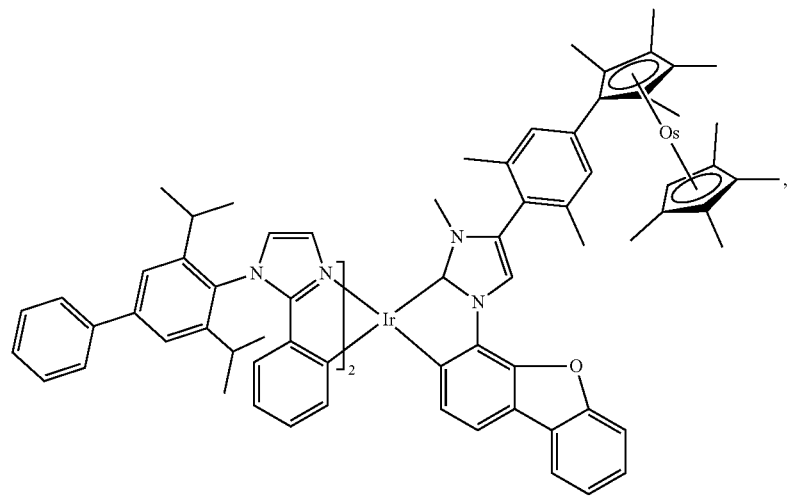
Compound 15
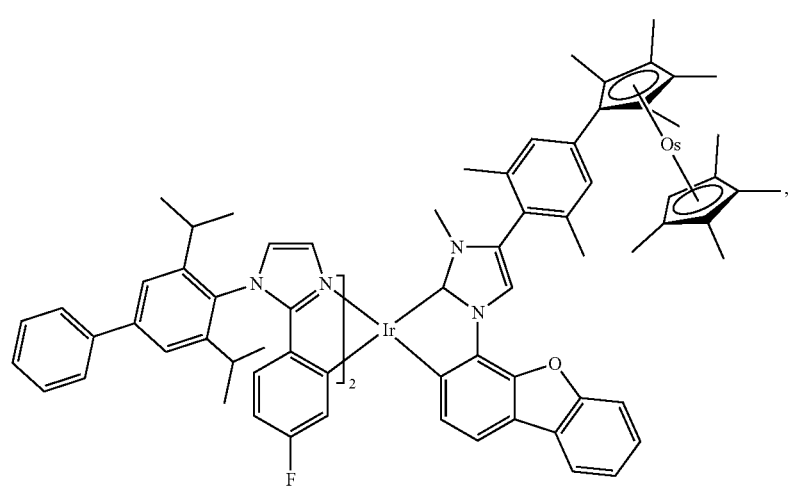
Compound 16
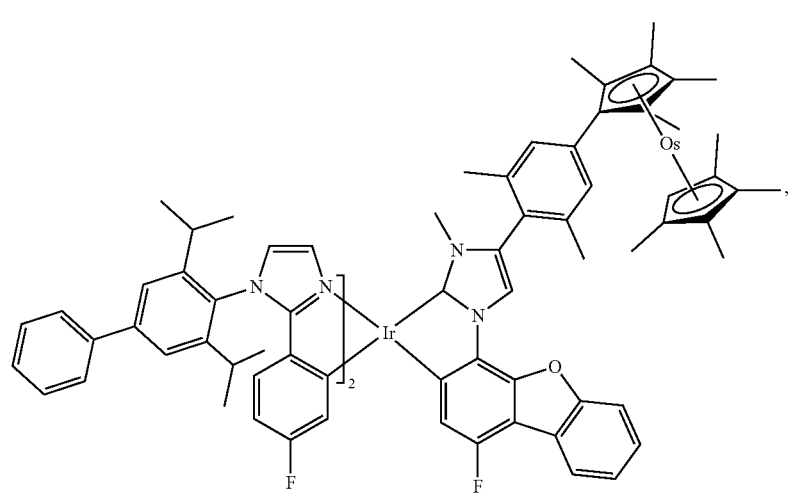

-continued
Compound 19
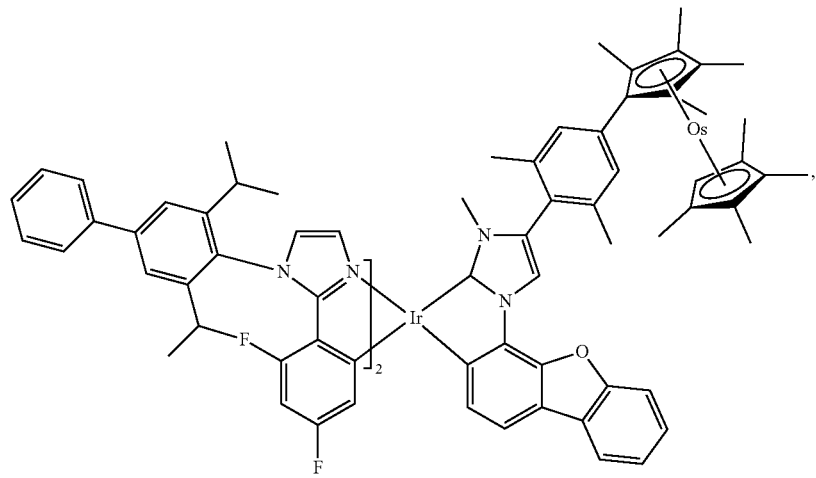
Compound 23
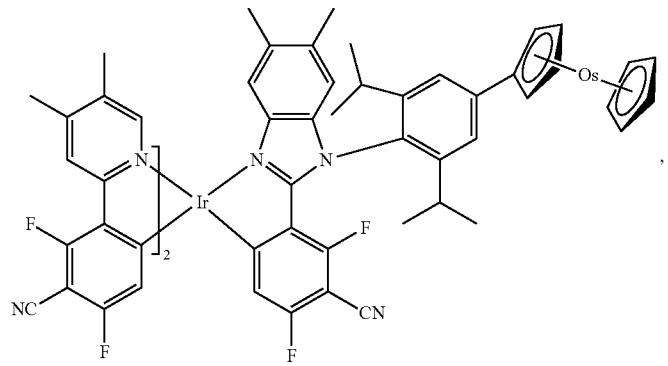
Compound 24
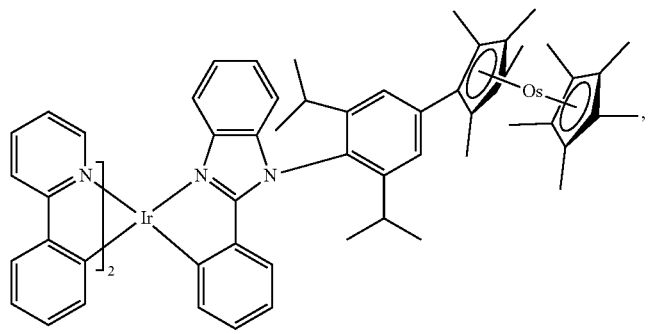
Compound 25
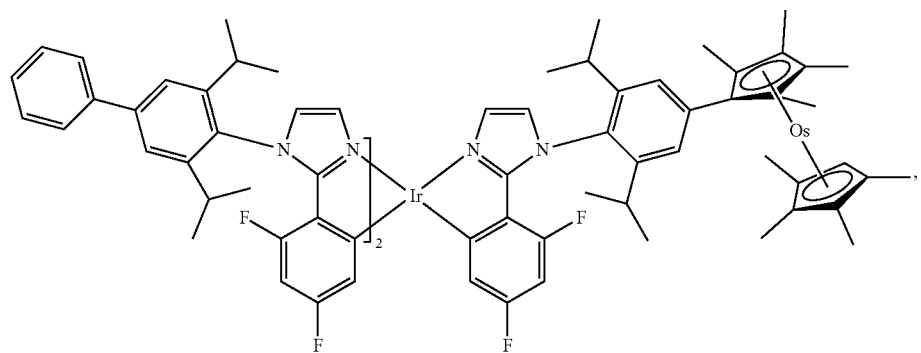

-continued
Compound 26
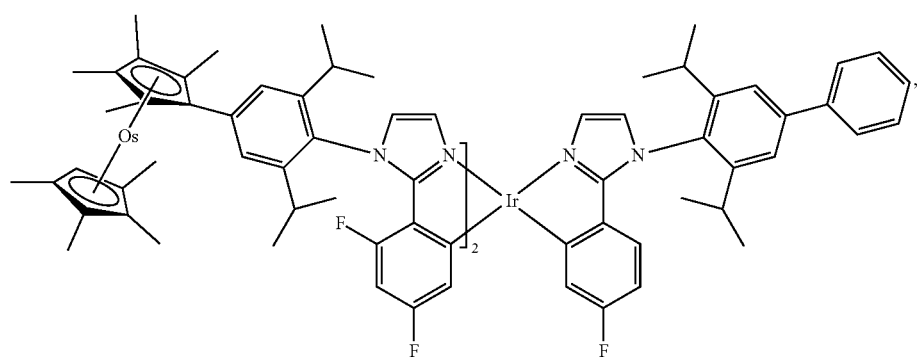
Compound 27
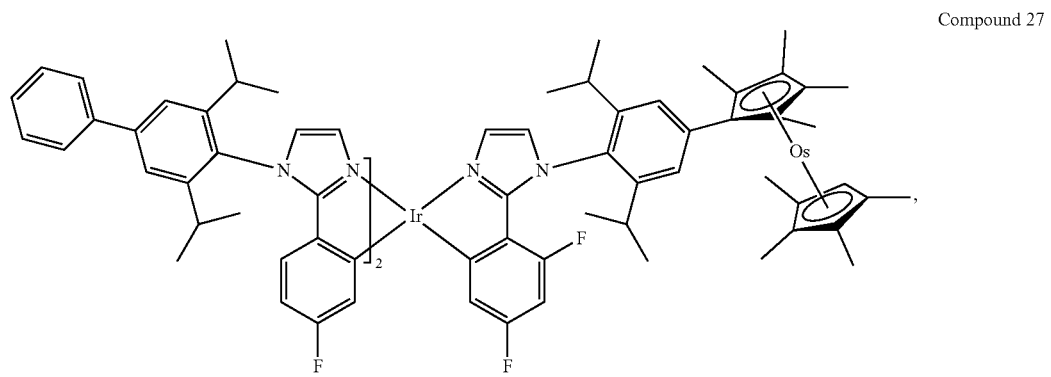
Compound 28
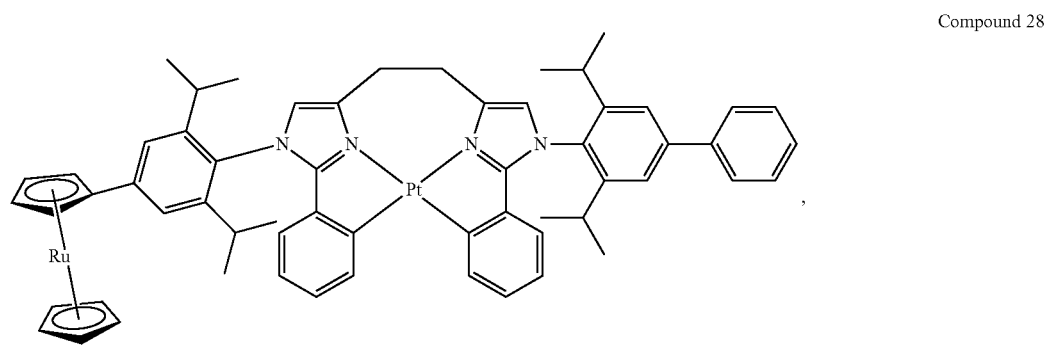
Compound 29
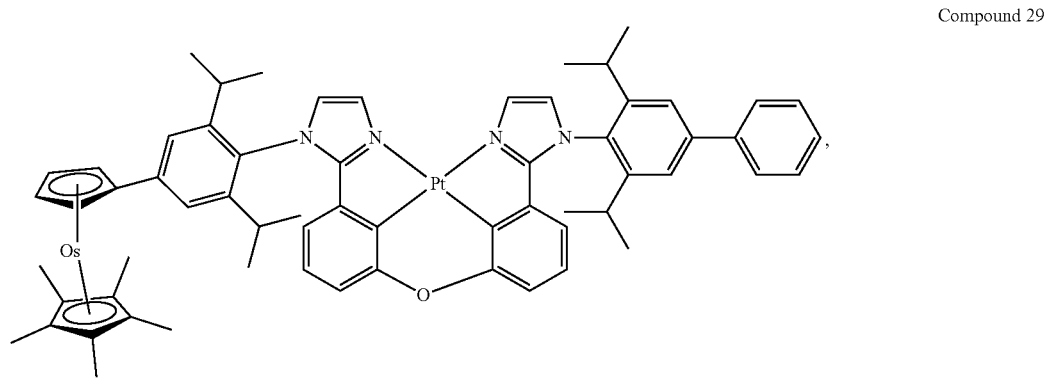

Compound 35
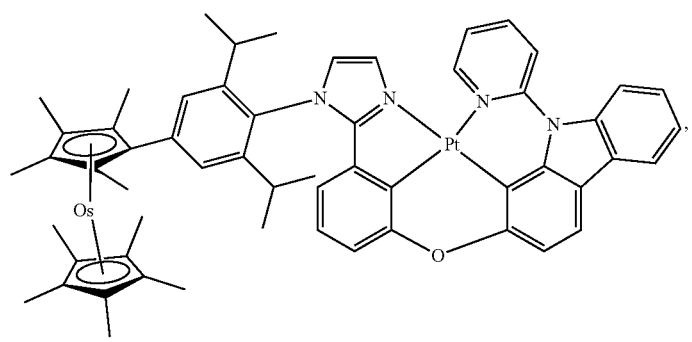
Compound 36
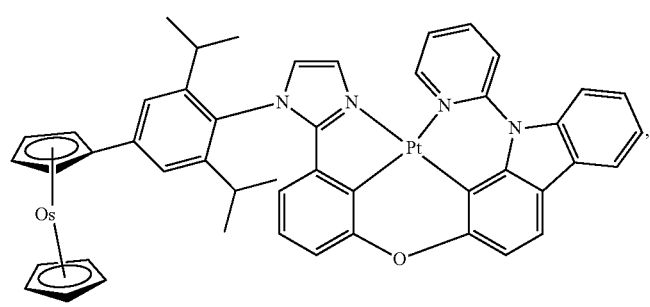
Compound 37
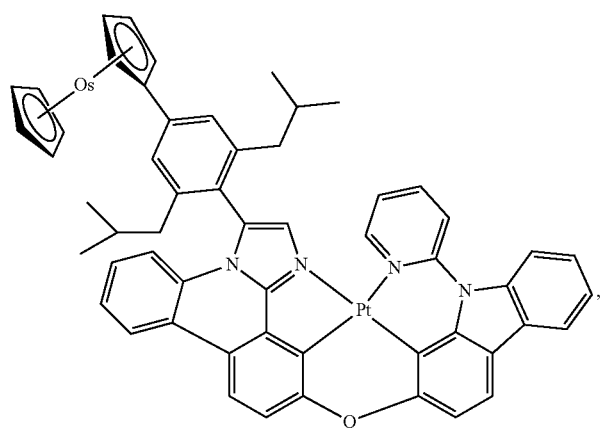
Compound 38
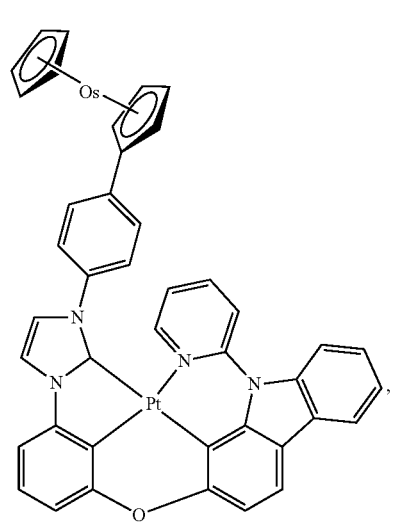
and Compound 39

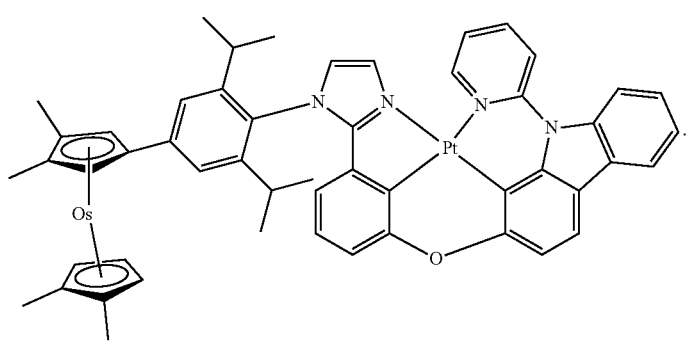

11. A device comprising one or more organic light emitting devices, at least one of the one or more organic light emitting devices comprising:
an anode;
a cathode; and
an organic layer, disposed between the anode and the cathode, the organic layer comprising a compound comprising a first ligand $L^1$ having the Formula:

Formula I

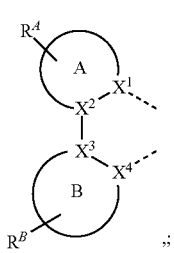

wherein
(1) ring A is a pyridine and ring B is a phenyl, $X^1$ is N, and $X^2$, $X^3$ and $X^4$ are C; or
(2) ring A is an imidazole or its derived carbene, and ring B is a phenyl, wherein $X^1$ and $X^2$ are independently N or C, and $X^3$ and $X^4$ are C;
wherein $R^A$ and $R^B$ each independently represent mono, di, tri, or tetra substitution, or no substitution;
wherein at least one of $R^A$ and $R^B$ is present and has a structure according to the following formula:

Formula II

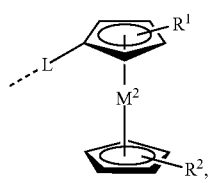

wherein L is a direct bond or a linker selected from the group consisting of alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein $R^1$ represents mono, di, tri, or tetra substitution, or no substitution;
wherein $R^2$ represents mono, di, tri, tetra, or penta substitution, or no substitution;
wherein $M^2$ is selected from the group consisting of Os, Ru, and Re;
wherein $R^1$ and $R^2$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;
wherein when $R^A$ and $R^B$ is not Formula II, $R^A$ and $R^B$ are each independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;
wherein any two adjacent substituents are optionally joined to form a ring, which can be further substituted;
wherein the ligand $L^1$ is coordinated to Pt or Ir;
wherein Pt and Ir can be coordinated to other ligands; and
wherein the ligand $L^1$ is optionally linked with other ligands to comprise a tridentate, tetradentate, pentadentate or hexadentate ligand.

12. The device of claim 11, wherein the device is selected from the group consisting of a consumer product, an electronic component module, an organic light-emitting device, and a lighting panel.

13. The device of claim 11, wherein the organic layer is an emissive layer and the compound is an emissive dopant or a non-emissive dopant.

14. The device of claim 11, wherein the organic layer further comprises a host comprising at least one chemical group selected from the group consisting of carbazole, triphenylene, aza-triphenylene, dibenzothiphene, dibenzofuran, dibenzoselenophene, azacarbazole, aza-dibenzothiophene, aza-dibenzofuran, and aza-dibenzoselenophene.

15. The device of claim 11, wherein the organic layer further comprises a host selected from the group consisting of:

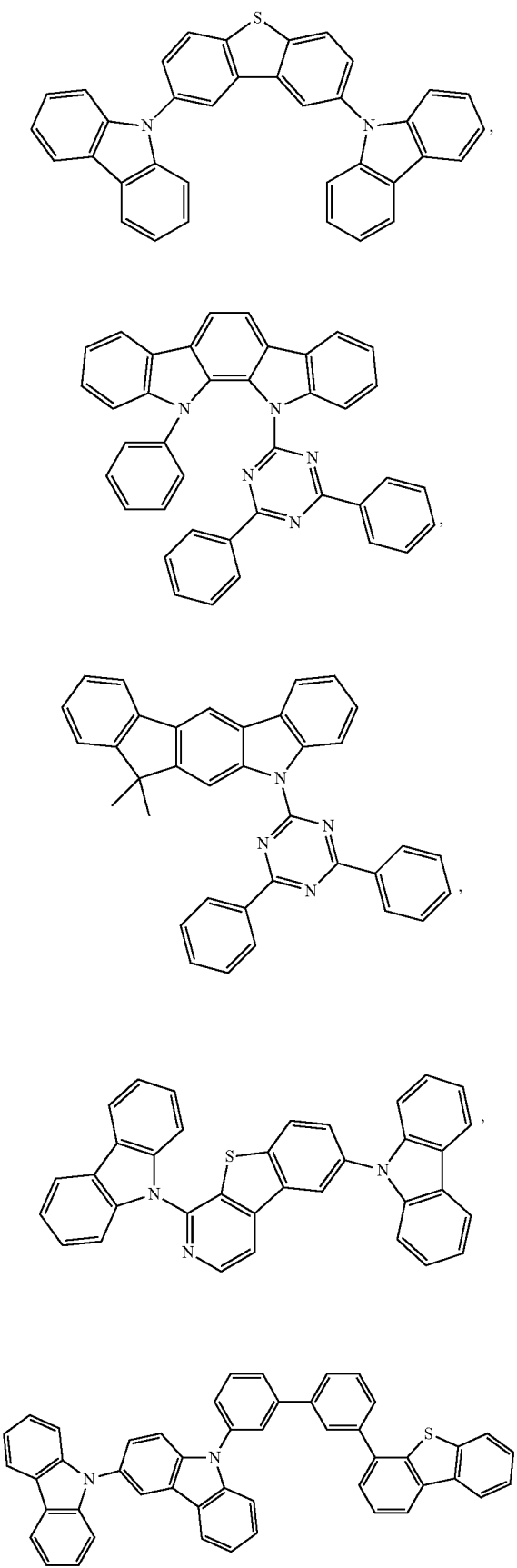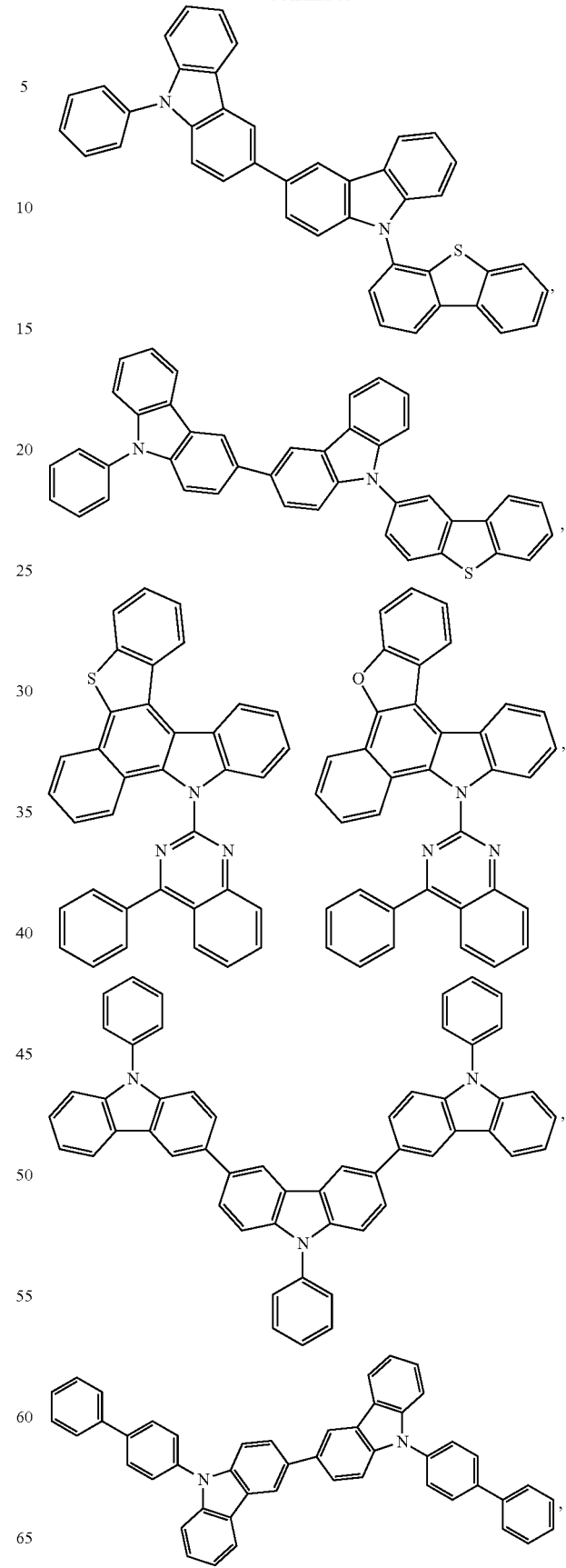

-continued
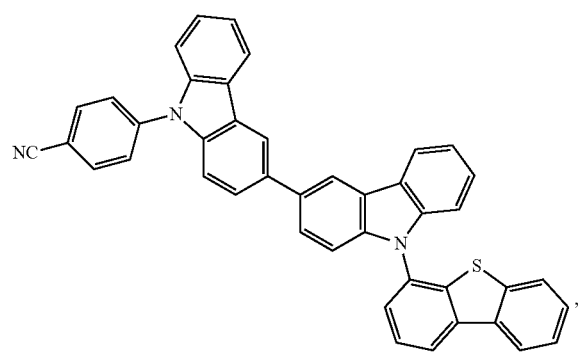
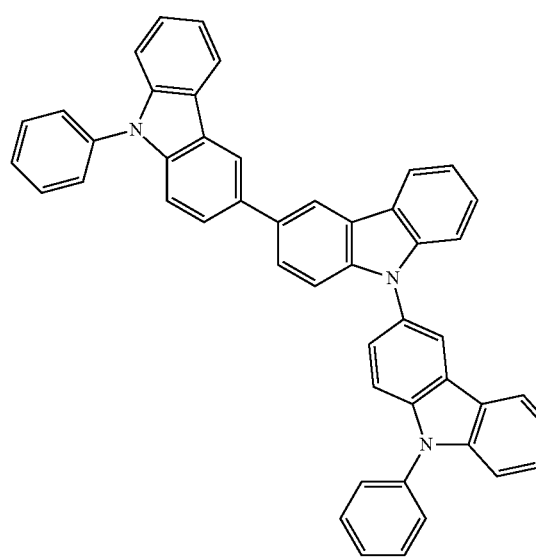
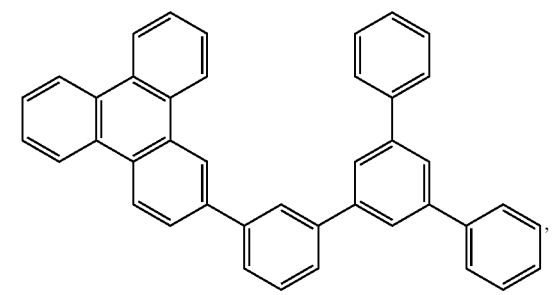
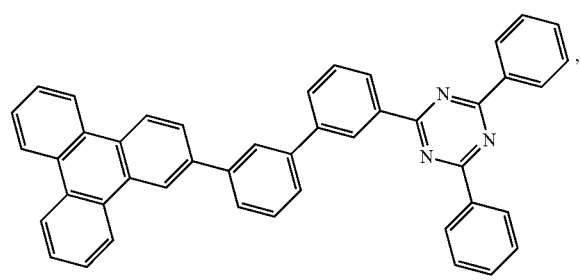
-continued
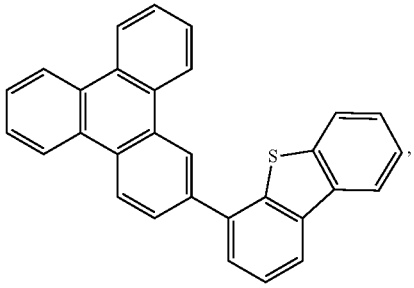
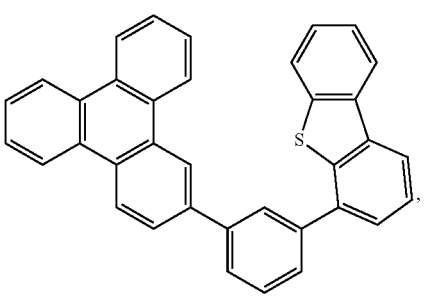
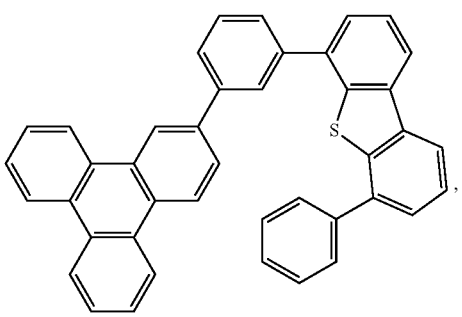
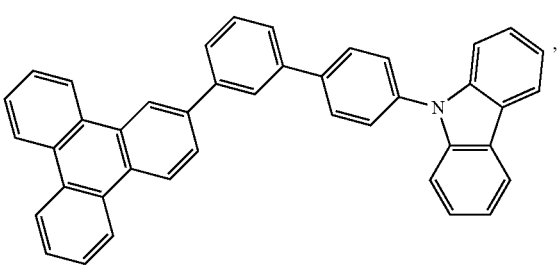
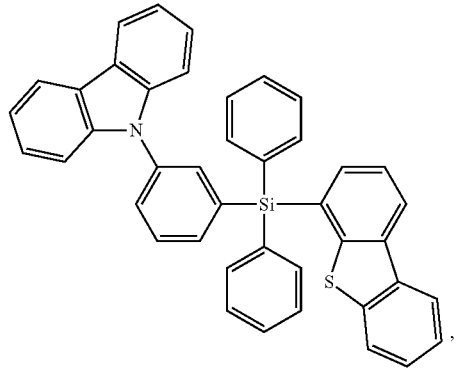

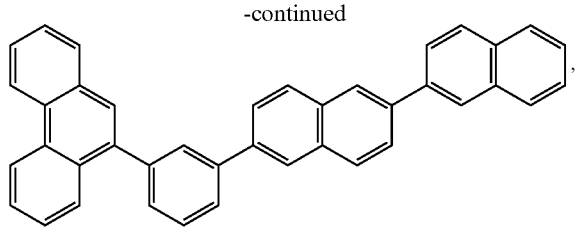

and combinations thereof.

16. A formulation comprising the compound of claim 1.

17. The compound of claim 1, wherein the compound has the formula of $Ir(L^1)_x(L^2)_y(L^3)_z$;

wherein $L^2$ is a second ligand, and $L^3$ is a third ligand, and $L^2$ and $L^3$ can be the same or different;

wherein x is 1, 2, or 3;

wherein y is 0, 1, or 2;

wherein z is 0, 1, or 2;

wherein x+y+z is the oxidation state of the metal M;

wherein the second ligand $L^2$ and the third ligand $L^3$ are independently selected from the group consisting of:

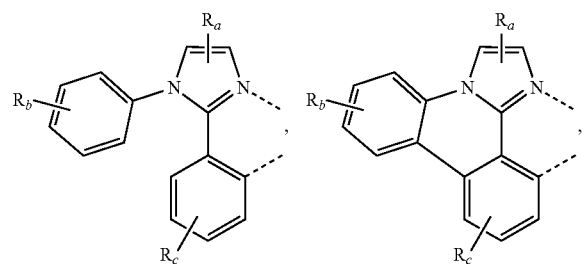

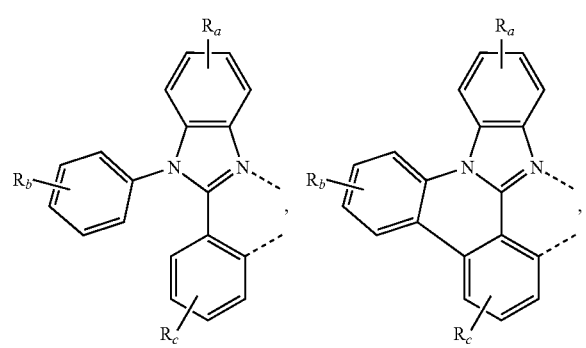

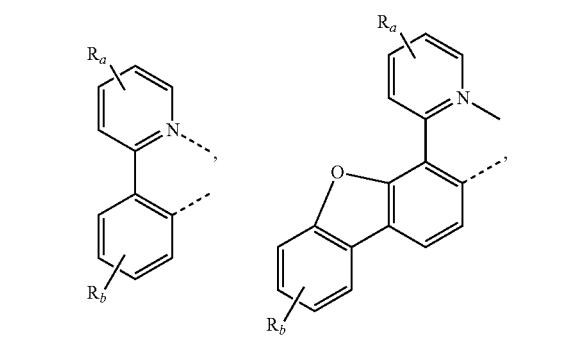

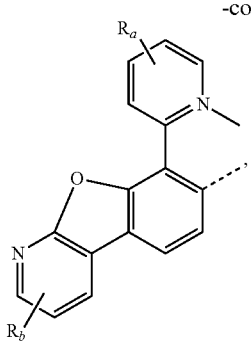
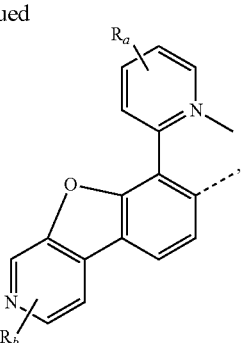

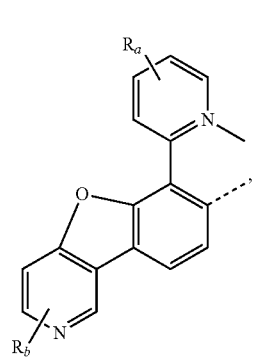
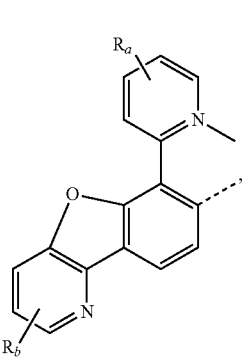

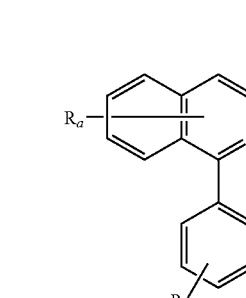
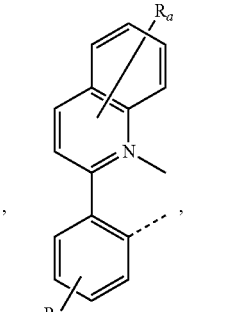

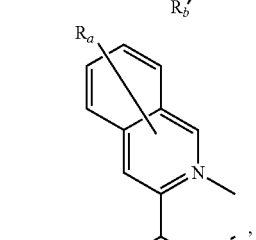
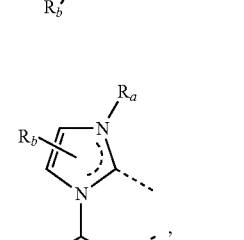

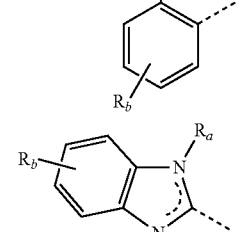
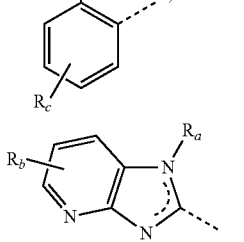

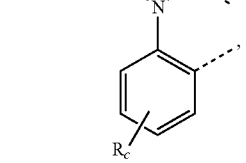
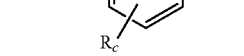

-continued

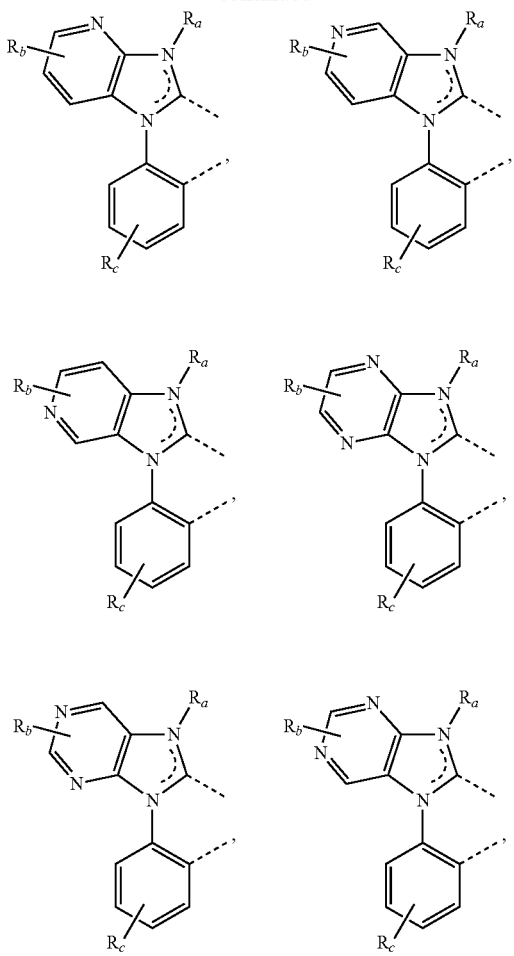

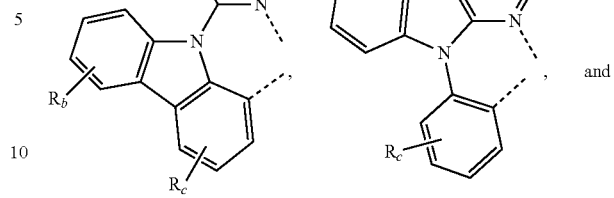

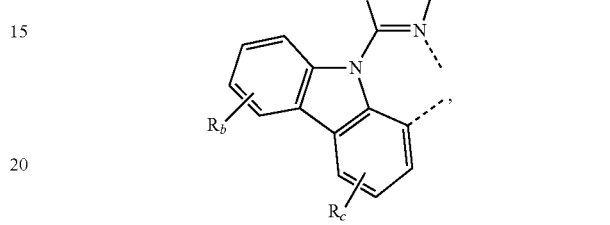

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

18. The compound of claim 17, wherein the compound has the formula of $Ir(L^1)(L^2)_2$.

* * * * *

UNITED STATES PATENT AND TRADEMARK OFFICE
CERTIFICATE OF CORRECTION

PATENT NO. : 10,000,517 B2
APPLICATION NO. : 15/590218
DATED : June 19, 2018
INVENTOR(S) : Jui-Yi Tsai and Chuanjun Xia Page 1 of 6

It is certified that error appears in the above-identified patent and that said Letters Patent is hereby corrected as shown below:

In the Specification

Column 25, Lines 3-14, please delete the compound

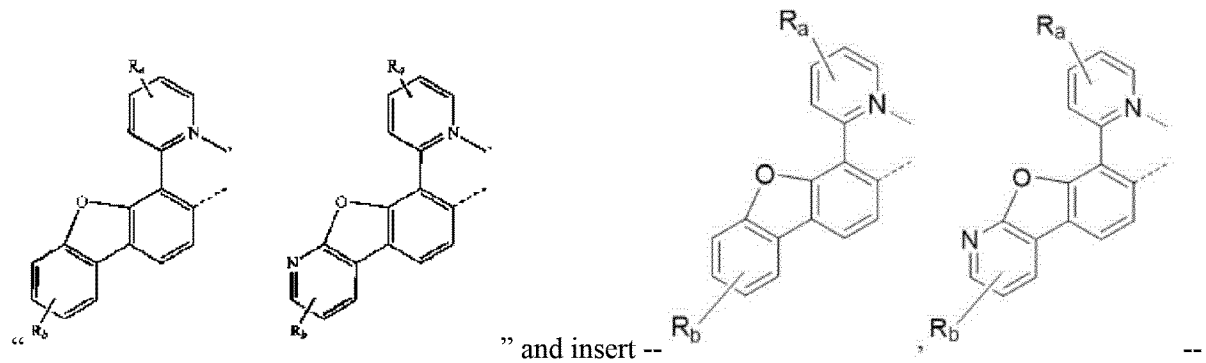

" and insert --   --

Column 25, Lines 15-26, please delete the compound

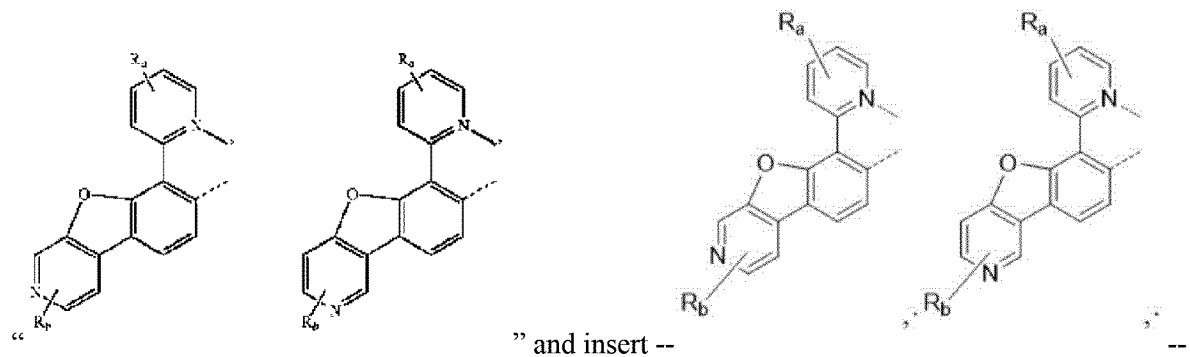

" and insert --   --

Signed and Sealed this
Thirtieth Day of April, 2019

Andrei Iancu
*Director of the United States Patent and Trademark Office*

CERTIFICATE OF CORRECTION (continued)
U.S. Pat. No. 10,000,517 B2

Column 25, Lines 27-40, please delete the compound

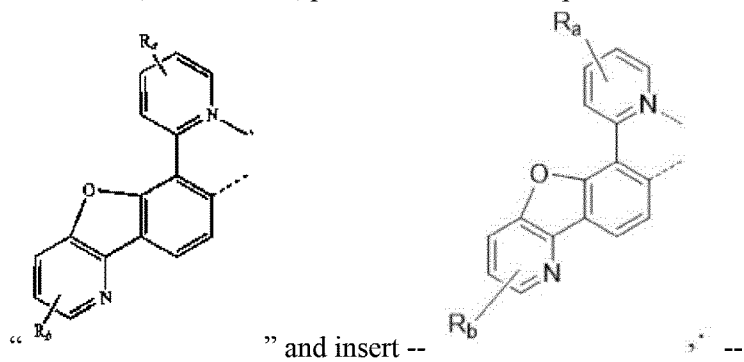

" and insert -- , --

Column 26, Lines 33-43, please delete the compound

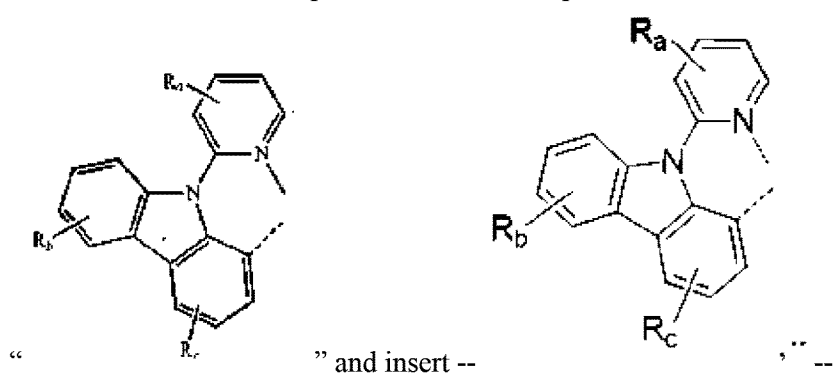

" and insert -- , --

Column 26, Lines 44-50, please delete the compound

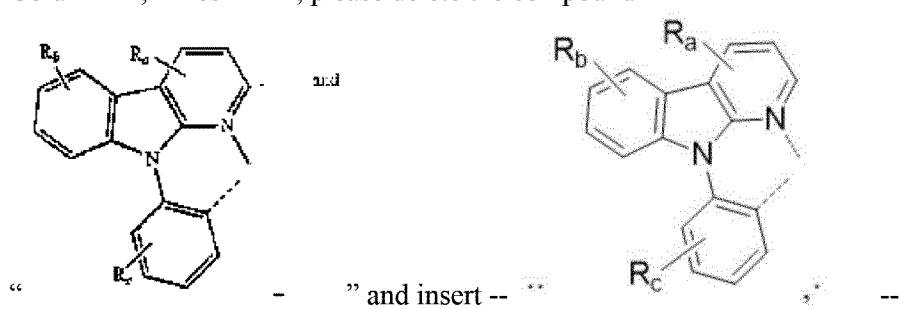

" and insert -- , --

Column 26, Lines 51-67, please delete the compound

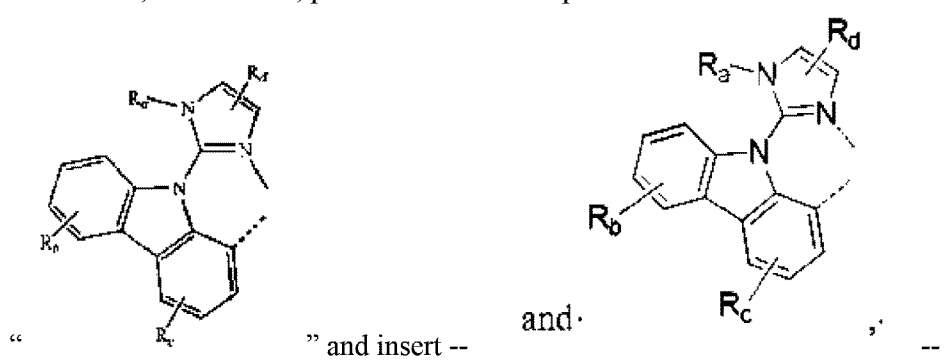

" and insert -- , --

In the Claims
Column 150, Lines 50-67, please delete the compound
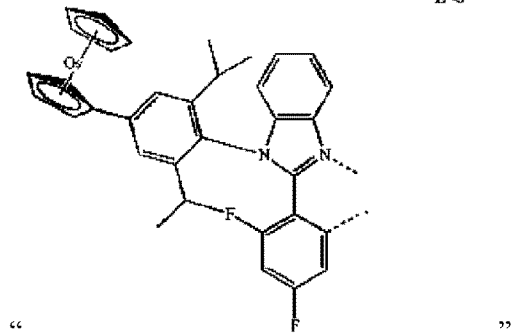
" "
Column 154, Lines 25-40, please delete the compound
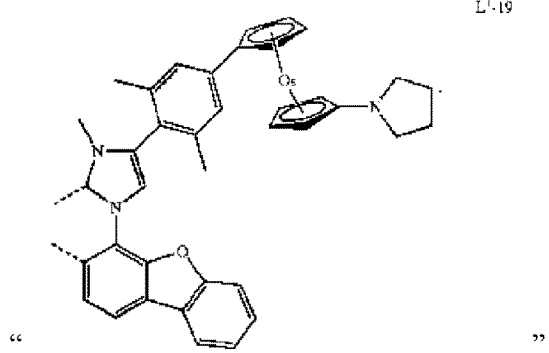
" "
Column 156, Lines 3-12, please delete the compound
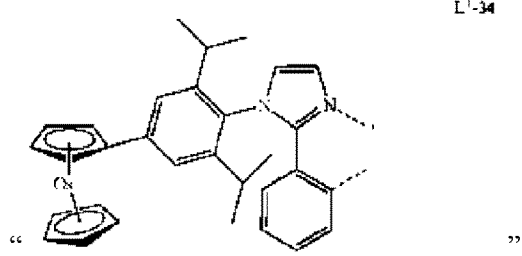
" "
Column 158, Lines 55-67, please delete the compound
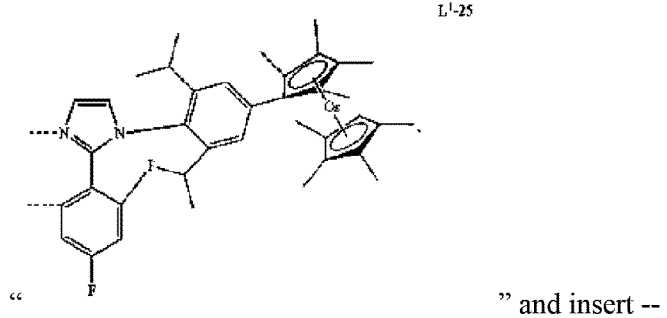 " and insert -- 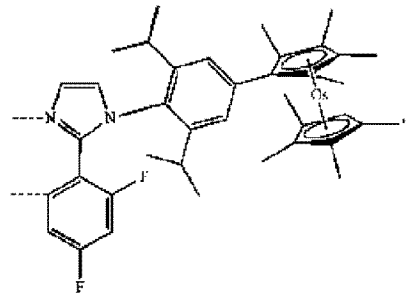 --

CERTIFICATE OF CORRECTION (continued)
U.S. Pat. No. 10,000,517 B2

Column 159, Lines 3-22, please delete the compound

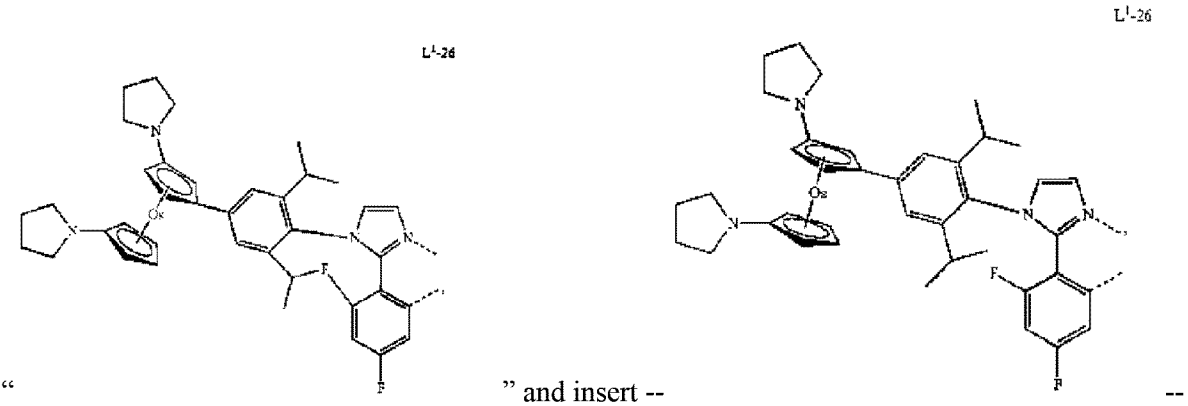

" and insert --   --

Column 159, Lines 23-40, please delete the compound

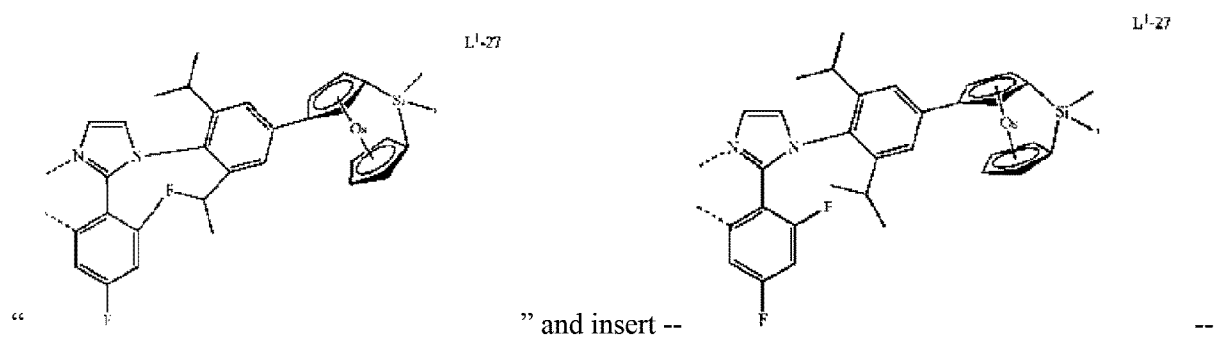

" and insert --   --

Column 163, Lines 22-32, please delete the compound

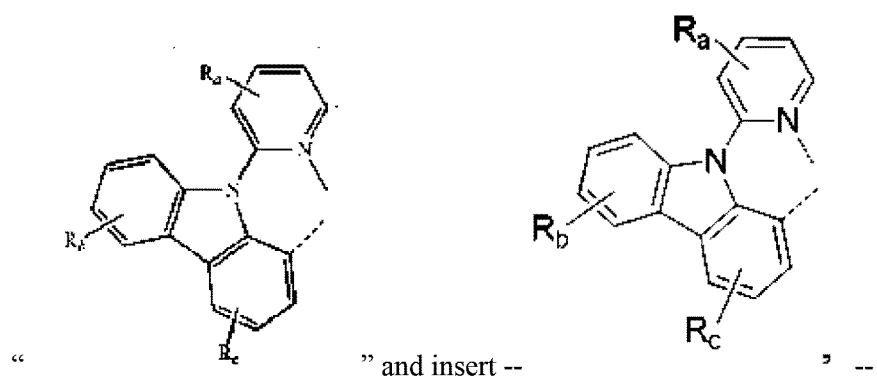

" and insert --   --

Column 163, Lines 33-41, please delete the compound
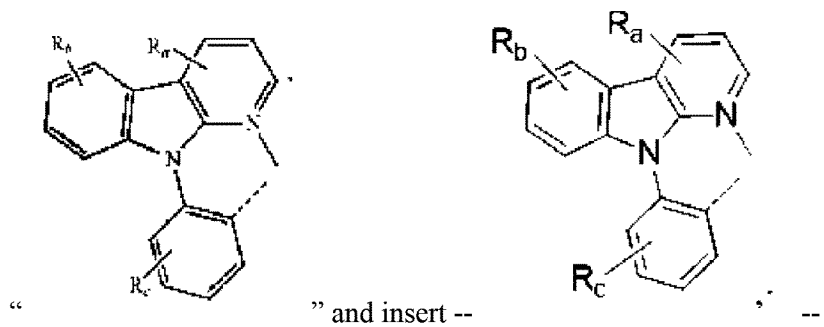
" and insert -- ,--
Column 163, Lines 42-52, please delete the compound
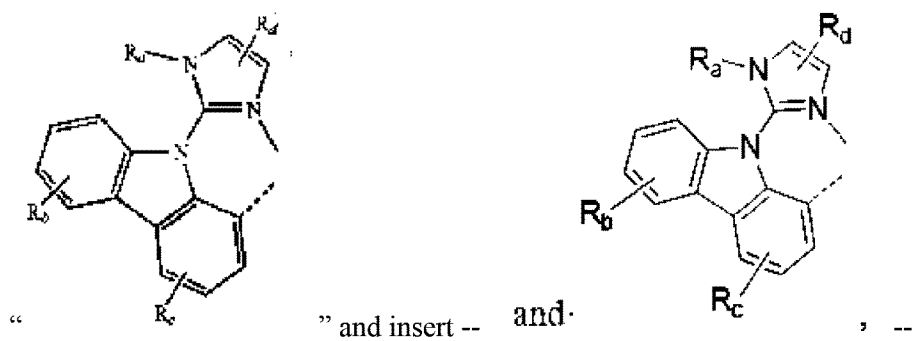
" and insert -- ,--
Column 185, Lines 54-67, please delete the compound
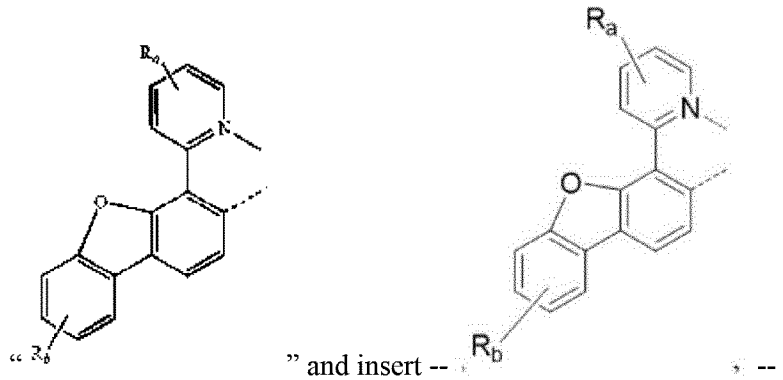
" and insert -- ,--
Column 186, Lines 3-15, please delete the compound
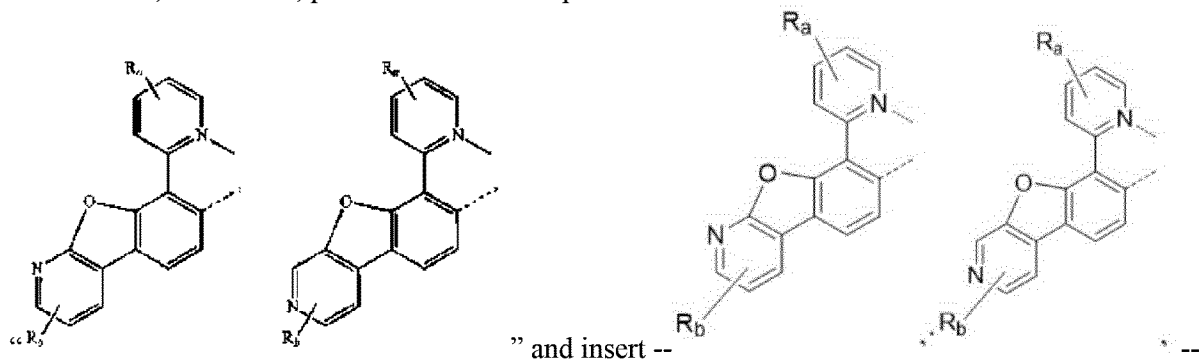
" and insert -- ,--

CERTIFICATE OF CORRECTION (continued)
U.S. Pat. No. 10,000,517 B2

Column 186, Lines 16-29, please delete the compound

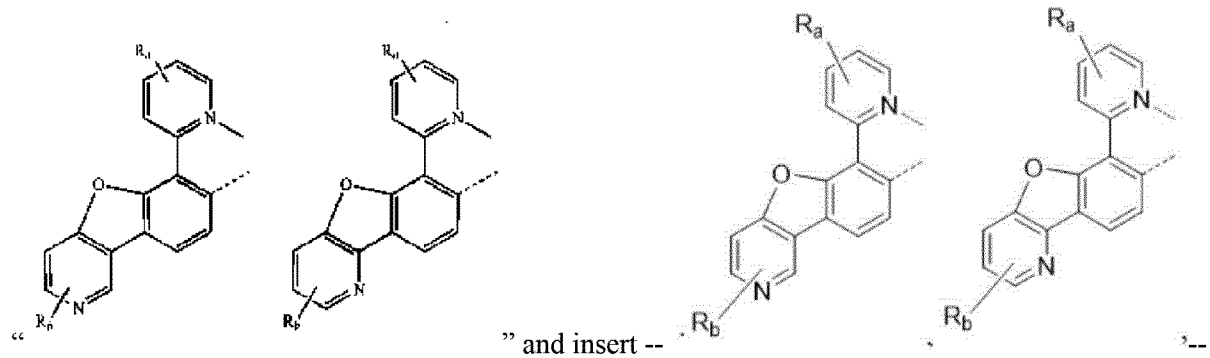

" and insert -- ... --

Column 186, Lines 30-41, please delete the compound

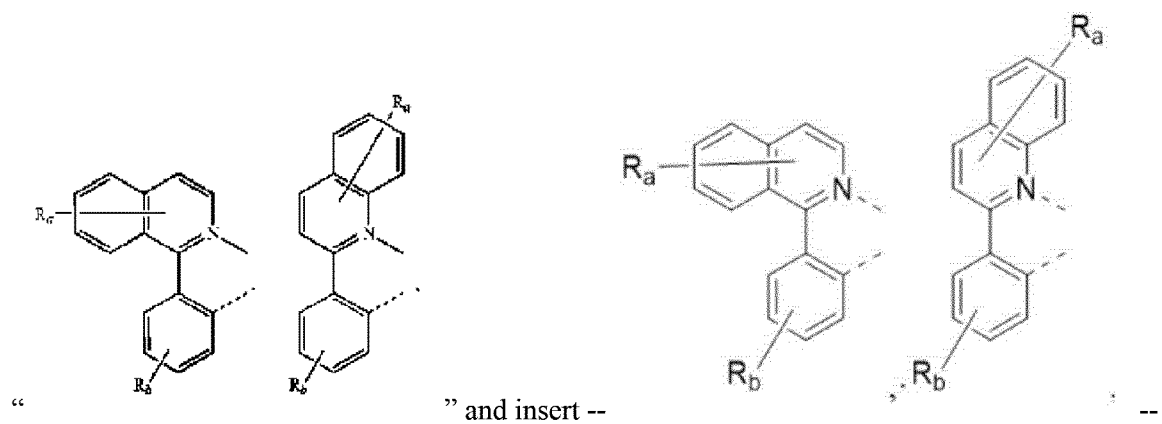

" and insert -- ... --

Column 186, Lines 42-55, please delete the compound

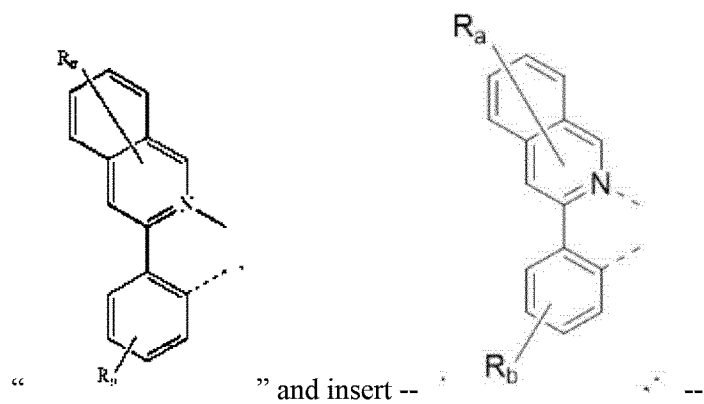

" and insert -- ... --